(12) United States Patent
Luthringer et al.

(10) Patent No.: US 11,766,430 B2
(45) Date of Patent: Sep. 26, 2023

(54) METHODS OF USING A PHENOXYPROPYLAMINE COMPOUND TO TREAT PAIN

(71) Applicant: Minerva Neurosciences, Inc., Waltham, MA (US)

(72) Inventors: Remy Luthringer, Geneva (CH); Nadine Noel, Gildwiller (FR); Jay Saoud, Waltham, MA (US)

(73) Assignee: Minerva Neurosciences, Inc., Burlington, MA (US)

( * ) Notice: Subject to any disclaimer, the term of this patent is extended or adjusted under 35 U.S.C. 154(b) by 0 days.

(21) Appl. No.: 16/559,687

(22) Filed: Sep. 4, 2019

(65) Prior Publication Data

US 2020/0069672 A1    Mar. 5, 2020

Related U.S. Application Data

(60) Provisional application No. 62/726,800, filed on Sep. 4, 2018.

(51) Int. Cl.
| | | |
|---|---|---|
| *A61K 31/454* | (2006.01) | |
| *A61P 29/00* | (2006.01) | |
| *A61P 25/02* | (2006.01) | |

(52) U.S. Cl.
CPC ............ *A61K 31/454* (2013.01); *A61P 25/02* (2018.01); *A61P 29/00* (2018.01)

(58) Field of Classification Search
None
See application file for complete search history.

(56) References Cited

U.S. PATENT DOCUMENTS

| | | | |
|---|---|---|---|
| 4,207,343 A | 6/1980 | Lavagnino et al. | |
| 4,522,811 A | 6/1985 | Eppstein et al. | |
| 6,720,320 B2* | 4/2004 | Nishiyama | A61P 1/00 514/233.5 |
| 8,084,447 B2* | 12/2011 | Salvati | A61K 31/16 514/183 |
| 8,716,231 B2 | 5/2014 | Smith-Swintosky et al. | |
| 2002/0111358 A1 | 8/2002 | Nishiyama et al. | |
| 2002/0165263 A1 | 11/2002 | Dinan et al. | |
| 2004/0147581 A1 | 7/2004 | Taylor et al. | |
| 2014/0206722 A1 | 7/2014 | Pellegrini et al. | |
| 2019/0183874 A1 | 6/2019 | Luthringer et al. | |
| 2020/0223838 A1 | 7/2020 | Pellegrini et al. | |

FOREIGN PATENT DOCUMENTS

| | | |
|---|---|---|
| CN | 101809000 A | 8/2010 |
| RU | 2424799 C1 | 7/2011 |
| WO | WO 01/46179 A1 | 6/2001 |
| WO | WO-2010120719 A1 | 10/2010 |

OTHER PUBLICATIONS

Wang et al., Pain 106 (2003) 135-142. (Year: 2003).*
Zhang et al., Pain 98 (2002) 287-295. (Year: 2002).*
Scripture, Curr Neuropharmacol. Apr. 2006; 4(2): 165-172 (Year: 2006).*
Zuxiao, Bao (ed.), "Learnings from Diagnosis and Treatment of Anxiety Disorders," People's Military Medical Publishing House, Apr. 2015, pp. 3-4 (with English translation).
Arakawa et al., "Determination of optimal dose of psychotropic drug using PET," Isotope News, Jul. 1, 2006, No. 627, pp. 2-5 and English translation.
Argyropoulos et al., "Sleep disturbances in depression and the effects of antidepressants," International Review of Psychiatry, Aug. 2005; 17(4): 237-245.
Bennett, G. J. and Xie, Y.-K., "A peripheral mononeuropathy in rat that produces disorders of pain sensation like those seen in man," Pain, 1988 (33):87-107.
Berge et al., "Pharmaceutical Salts," Journal of Pharmaceutical Sciences, Jan. 1977, vol. 66, No. 1, pp. 1-19.
Chaplan, S. R. et al., "Qualitative Assessment of Tactile Allodynia in the Rat Paw," Journal of Neuroscience Methods, 53 (1994), 55-63.
Dunner D. et al. "Optimal Dose Regimen for Paroxetine," J. Clin. Psychiatry (Feb. 1992 (suppl), vol. 53, No. 2, pp. 21-26.
El Mansari, M. et al., "In vivo electrophysiological assessment of the putative antidepressant Wf-516 in the rat raphe dorsalis, locus coeruleus and hippocampus," Naunyn-Schmiedeberg's Arch Pharmacol, (2008), vol. 376, pp. 351-361.

(Continued)

*Primary Examiner* — Jean P Cornet
(74) *Attorney, Agent, or Firm* — COOLEY LLP

(57) ABSTRACT

The present disclosure relates to methods of treating pain, fibromyalgia, neuropathy, chemotherapy-induced pain, promoting an antihyperalgesic effect, and reducing sensitivity to pain, in a subject in need of such treatment comprising the administration of a therapeutically effective amount of Compound I, or a pharmaceutically acceptable salt, solvate, or prodrug thereof.

Compound I

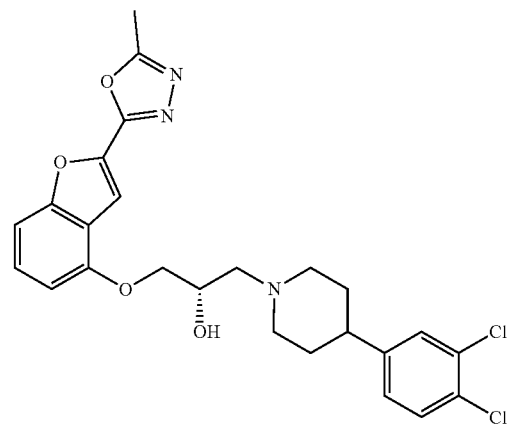

18 Claims, 8 Drawing Sheets

(56) References Cited

OTHER PUBLICATIONS

Ferguson, M. "SSRI Antidepressant Medications: Adverse Effects and Tolerability," Primary Care Companion J. Clin. Psychiatry, (Feb. 2001), vol. 3, No. 1, pp. 22-27.
Haefeli, H. et al., "Pain assessment," Eur Spine J (2006) 15:S17-S24.
Hicks, J.A. et al., "Randomized controlled study of sleep after nefazodone or paroxetine treatment in out-patients with depression," British Journal of Psychiatry, (2002), vol. 180, pp. 528-535.
Maeda, J. et al. "Wf-516, a novel antidepressant with dual serotonergic activity: II. Pharmacological profiles ex vivo and in vivo to monoamine transporters in comparison with standard antidepressant," Affective disorders and antidepressants—Antidepressants (basic), Eur Neuropsychopharmacol, 2006, pp. S333-S334.
Maeda, J. et al. "Wf-516, a novel antidepressant with dual serotonergic activity: I. Receptor and pharmacological profiles in comparison with reference antidepressants," Affective disorders and antidepressants—Antidepressants (basic), Eur Neuropsychopharmacol, 2006, pp. S333.
Nutt et al., "Sleep disorders as core symptoms of depression," Dialogues in Clinical Neuroscience 2008, 10:(3), pp. 329-336.
Papazacharias and Nardini "The relationship between depression and cognitive deficits," Psychiatria Danub. 2012, vol. 24, Suppl 1, pp. S179-S182.
Randall, L. O. and Selitto, J. J., "A method for measurement of analgesic activity on inflamed tissue," Arch Int Pharmacodyn, 1957, vol. 111, No. 4, pp. 409-419.
Reagan-Shaw, S., et al., "Dose translation from animal to human studies revisited," The FASEB Journal, (2007) 22:659-661.
Saijo T. et al. "Utility of small-animal positron emission tomographic imaging of rats for preclinical development of drugs acting on the serotonin transporter," International Journal of Neuropsychopharmacology, (2009), vol. 12, pp. 1021-1032.
Saijo, T. et al., "Presynaptic Selectivity of a Ligand for Serotonin 1A Receptors Revealed by In Vivo PET Assays of Rat Brain," PLoS ONE (Aug. 2012), vol. 7, Issue 8, e42589, 13 pages.
Sansone et al., "Pain, Pain, Go Away: Antidepressants and Pain Management," Psychiatry (Edgemont) 2008;5(12):16-19.
Schmitt J. A. J. et al. "Serotonin and human cognitive performance," Current Pharmaceutical Design 2006, vol. 12, No. 20, 2006, pp. 2473-2486.
Scholl, L. et al. "Drug and Opioid-Involved Overdose Deaths—United States, 2013-2017," MMWR Morb Mortal Wkly Rep. 2019 67(5152):1419-1427.
Stewart, J., "The Challenges of Cancer Pain Assessment," Ulster Med J 2014;83(1):44-46.
Thayer, "Contained Chemistry, Synthesizing highly potent compounds is a lucrative and growing niche for custom chemical manufacturers," Chemical and Engineering News, 2008, 86:(24), 17 pages.
U.S. Department of Health and Human Services et al., "Guidance for Industry: Estimating the Maximum Safe Starting Dose in Initial Clinical Trials for Therapeutics in Adult Healthy Volunteers," Jul. 2005, 30 pages.
Yauzina, N. A. et al. "Current experimental models of depression," Biomedicine, 2013, No. 1, pp. 61-71 (with English abstract on p. 71).
Bourgoin et al., "Yin and Yang in Serotonin: Its Janus Roles in Pain Control Mechanisms," Douleur Analg. (2017), 30:35-56 (with English abstract).
International Search Report and Written Opinion of the International Searching Authority for International Application No. PCT/US2019/049492, dated Jun. 2, 2020, 10 pages.
Papp et al., "Antidepressant-like activity of Wf-516, an antagonist of 5-HT1A receptors and inhibitor of 5-HT reuptake, in a chronic mild stress model of depression in rat," European Neuropsychopharmacology, 2006, vol. 16, Abstract P.2.b.008, pp. S305-S306.
Griebel et al., "The effects of compounds varying in selectivity as 5-HT$_{1A}$ receptor antagonists in three rat models of anxiety," Neuropharmacology (2000) 39: 1848-1857.
Gorman, J.M., "Comorbid Depression and Anxiety Spectrum Disorders," Depression and Anxiety (1996/1997) 4: 160-168.
Hamilton Anxiety Rating Scale (HAM-A), pp. 81-82, reference: Hamilton M. The assessment of anxiety states by rating. Br J Med Psychol 1959; 32:50-55.
Dunner, D. et al., "Duloxetine in treatment of anxiety symptoms associated with depression," Depression and Anxiety, 18:53-61, 2003.
Inoue, T., Pharmacotherapy of Anxiety Disorders, Psychiat. Neurol. Journal, 2012, vol. 114, No. 9, pp. 1085-1092 (with English abstract).
Matsumoto and Yoshioka, Possible involvement of serotonin receptors in anxiety disorders, Folia Pharmacol. Jpn (Nippon Yakurigaku Zasshi), 2000, 115, pp. 39-44 (with English abstract).
Sisignano et al., "Mechanism-based treatment for chemotherapy-induced peripheral neuropathic pain," Nat. Rev. Neurol. (2014) 10, 694-707.
Cassano et al., "Psychopharmacology of anxiety disorders," Dialogues in Clinical Neuroscience, (2002) 4:3, 271-285.
Dimsdale et al., "The Effect of Opioids on Sleep Architecture," J Clin Sleep Med 2007;3(1):33-36.
Thase, M., "Antidepressant Treatment of the Depressed Patient With Insomnia," J Clin Psychiatry 1999; 60(Suppl 17): 28-31.
Thase, M., "Treatment Issues Related to Sleep and Depression," J Clin Psychiatry 2000; 61(Suppl 11): 46-50.
[Author Unknown] "Khimicheskiy entsiklopedicheskiy slovar" (Chemical Encyclopedic Dictionary), Moscow: «Sovetskaya Entsiklopediya» (1983); pp. 130-131; 7 pages with English translation of relevant portion.
Belikov, V. G., "Pharmaceutical Chemistry. Chapter 2.6 Relationship between the chemical structure, properties of substances and their effect on the body", MEDpress-inform (2007); pp. 27-29; 14 pages with English translation.
Belikov, V.G., "Pharmaceutical Chemistry", High School (1993); vol. 1: pp. 43-47; 14 pages with English Translation.
Dyson, G. M., et al., "May's Chemistry of Synthetic Drugs", Longmans, Fifth Edition, Moscow, MIR (1964); pp. 12-19; 20 pages with English translation of Russian Office Action for Russian Application No. 20200120236(034452).
Mashkovskiy, M.D., "Drugs", Moscow: "Medicine" (1993) Part 1, pp. 8; 3 pages with English Summary.
Smirnova, et al., "Optical Isomerism and Biological Activity of Medicines", Moscow University Gazette, Series 2, Chemistry (2012); 53(3): 147-156; 20 pages with English translation of Russian Office Action for Russian Application No. 20200120236(034452).
Mickle, A. D., et al., "T1755 Pro-Nociceptive Effect of 5-HT1A on Visceral Pain", Gastroenterology (2010); 5(138): 8571-8572.
Millan, M. J., "Serotonin and pain: evidence that activation of 5-HT$_{1A}$ receptors does not elicit antinociception against noxious thermal, mechanical and chemical stimuli in mice", Pain (1994); 58(1): 45-61.
Salat, K., et al., "Antinociceptive, antiallodynic and antihyperalgesic effects of the 5-HT$_{1A}$ receptor selective agonist, NLX-112 in mouse models of pain", Neuropharmacology (2017); 125: 181-188.
Wang, Y., et al., "Auraptenol attenuates vincristine-induced mechanical hyperalgesia through serotonin 5-HT$_{1A}$ receptors", Scientific Reports (2013); 3:3377. doi: 10.1038/srep03377 (4 pages).
Ward, S. J., et al., "Cannabidiol inhibits paclitaxel-induced neuropathic pain through 5-HT$_{1A}$ receptors without diminishing nervous system function or chemotherapy efficacy", British Journal of Pharmacology (2014); 171 (3): 636-645.

* cited by examiner

METHODS OF USING A PHENOXYPROPYLAMINE COMPOUND TO TREAT PAIN

RELATED APPLICATIONS

This application claims priority to, and the benefit of, U.S. Provisional Application No. 62/726,800, filed on Sep. 4, 2018, the contents of which are incorporated herein by reference in its entirety.

FIELD OF THE DISCLOSURE

The present disclosure relates to methods of treating pain, for example, acute pain, chronic pain, toxic pain, neuropathic pain, nociceptive pain, inflammatory pain, post-operative pain, visceral pain, chemotherapy-induced pain, or a combination thereof.

BACKGROUND OF THE DISCLOSURE

Therapeutic options for the treatment of pain are often ineffective due to adverse reactions, tolerance, dependence, and reductions in the quality of life. For example, in the U.S., dependence on opioids has emerged as a public health emergency. In 2016, for example, there were 63,632 overdose deaths in the US alone (Scholl, L. et al. "Drug and Opioid-Involved Overdose Deaths—United States, 2013-2017" MMWR Morb Mortal Wkly Rep. 2019 67(5152): 1419-1427. Thus, the development of additional, non-opioid therapeutic options for the treatment of pain is needed.

SUMMARY OF THE DISCLOSURE

In one aspect, this application pertains to a method of treating or preventing pain in a subject in need of treatment comprising administering to the subject a therapeutically effective amount of Compound I,

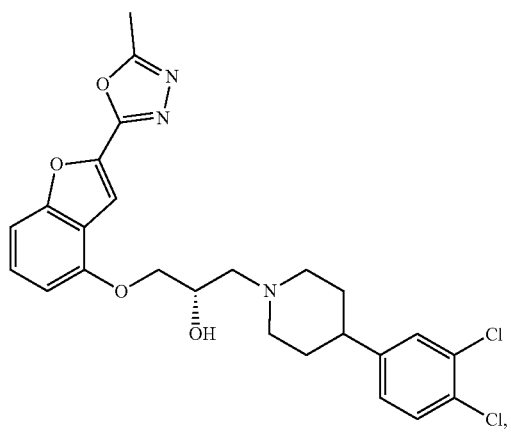 [SMILES: Cc1nnc(-c2cc3c(OC[C@@H](O)CN4CCC(c5ccc(Cl)c(Cl)c5)CC4)cccc3o2)o1]

or a pharmaceutically acceptable salt, solvate, or prodrug thereof.

In one aspect, this application pertains to a method of treating pain in a subject in need of treatment comprising administering to the subject a therapeutically effective amount of Compound I,

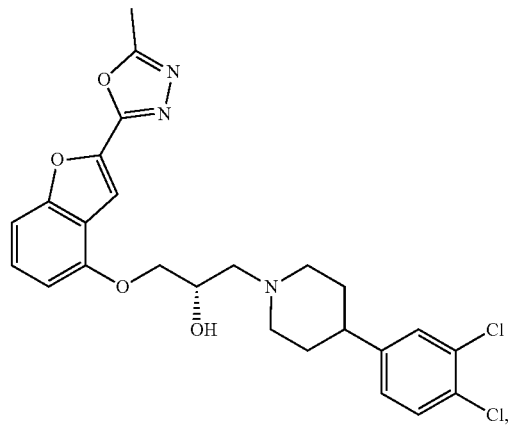 [SMILES: Cc1nnc(-c2cc3c(OC[C@@H](O)CN4CCC(c5ccc(Cl)c(Cl)c5)CC4)cccc3o2)o1]

or a pharmaceutically acceptable salt, solvate, or prodrug thereof.

In one aspect, this application pertains to a method of preventing pain in a subject in need of treatment comprising administering to the subject a therapeutically effective amount of Compound I,

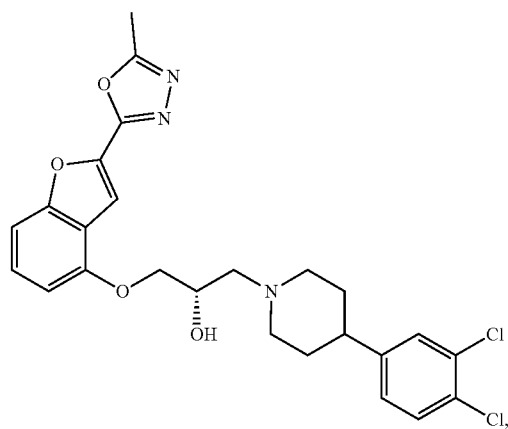 [SMILES: Cc1nnc(-c2cc3c(OC[C@@H](O)CN4CCC(c5ccc(Cl)c(Cl)c5)CC4)cccc3o2)o1]

or a pharmaceutically acceptable salt, solvate, or prodrug thereof.

In one embodiment, the pain is acute pain, chronic pain, toxic pain, neuropathic pain, nociceptive pain, inflammatory pain, post-operative pain, visceral pain, chemotherapy-induced pain, or a combination thereof.

In one embodiment, the pain is peripheral neuropathy.

In one embodiment, the pain is peripheral neuropathy that is peripheral mononeuropathy.

In one embodiment, the pain is peripheral neuropathy that is peripheral polyneuropathy.

In one embodiment, the pain is chemotherapy-induced peripheral neuropathy.

In one embodiment, the pain is chemotherapy-induced peripheral neuropathy, wherein the chemotherapy is paclitaxel.

In one aspect, this application pertains to a method of treating or preventing fibromyalgia in a subject in need of treatment comprising administering to the subject a therapeutically effective amount of Compound I,

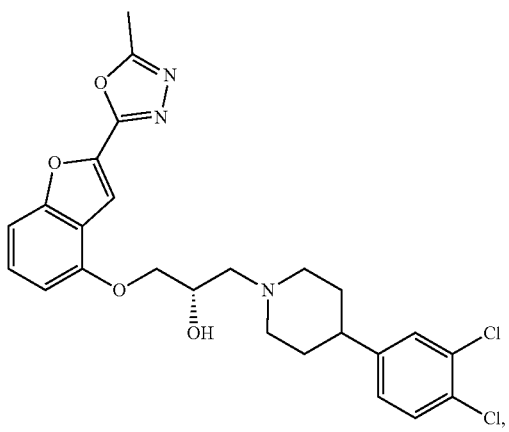 [SMILES: Cc1nnc(-c2cc3c(OC[C@@H](O)CN4CCC(c5ccc(Cl)c(Cl)c5)CC4)cccc3o2)o1]

or a pharmaceutically acceptable salt, solvate, or prodrug thereof.

In one aspect, this application pertains to a method of treating or preventing neuropathy in a subject in need of treatment comprising administering to the subject a therapeutically effective amount of Compound I,

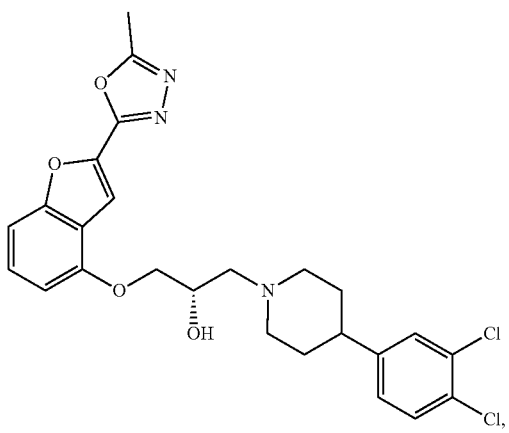 [SMILES: Cc1nnc(-c2cc3c(OC[C@@H](O)CN4CCC(c5ccc(Cl)c(Cl)c5)CC4)cccc3o2)o1]

or a pharmaceutically acceptable salt, solvate, or prodrug thereof.

In one embodiment, the neuropathy is peripheral neuropathy.

In one embodiment, the neuropathy is peripheral mononeuropathy.

In one embodiment, the neuropathy is peripheral polyneuropathy.

In one embodiment, the neuropathy is induced by chemotherapy.

In one aspect, this application pertains to a method of treating or preventing chemotherapy-induced pain in a subject in need of treatment comprising administering to the subject a therapeutically effective amount of Compound I,

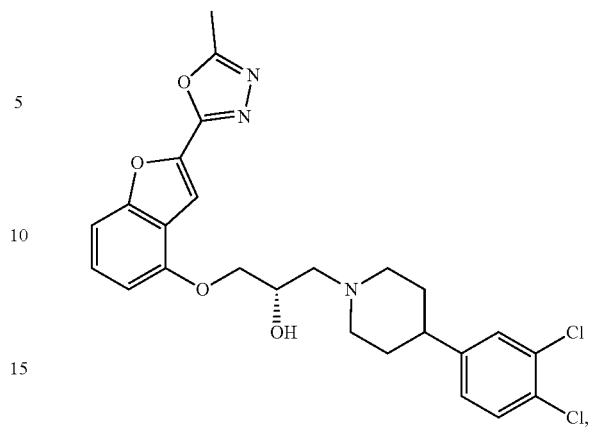

or a pharmaceutically acceptable salt, solvate, or prodrug thereof.

In one embodiment, the chemotherapy-induced pain is peripheral neuropathic pain.

In one embodiment, the chemotherapy is paclitaxel.

In one aspect, this application pertains to a method of promoting an antihyperalgesic effect in a subject suffering from hyperalgesia comprising administering to the subject a therapeutically effective amount of Compound I,

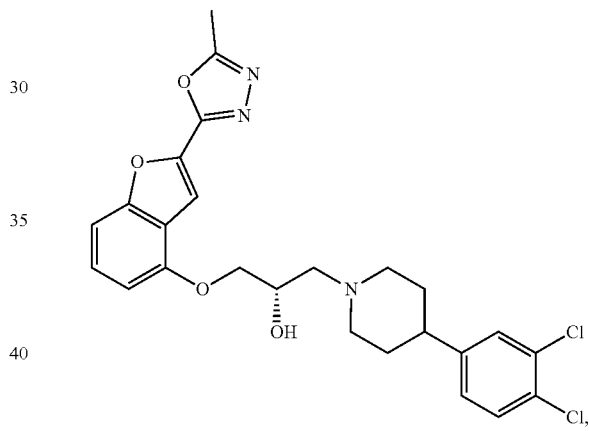

or a pharmaceutically acceptable salt, solvate, or prodrug thereof.

In one aspect, this application pertains to a method of reducing sensitivity to pain in a subject, comprising administering to the subject a therapeutically effective amount of Compound I,

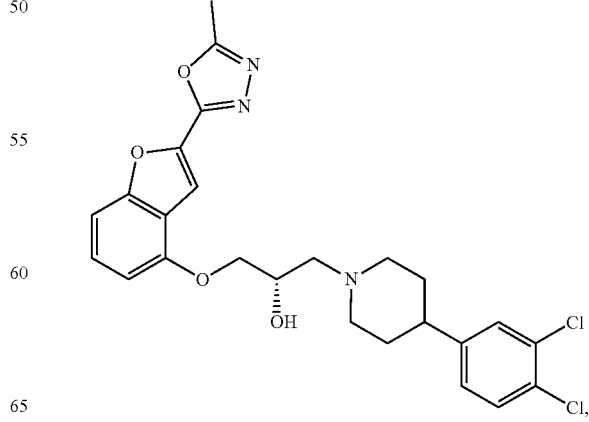

or a pharmaceutically acceptable salt, solvate, or prodrug thereof.

In one embodiment, for any of the methods of the application disclosed herein, the therapeutically effective amount of Compound I is 0.1 mg/kg to 100 mg/kg.

In one embodiment, for any of the methods of the application disclosed herein, the therapeutically effective amount of Compound I is about 10 mg/kg.

In one embodiment, for any of the methods of the application disclosed herein, the therapeutically effective amount of Compound I is 1 mg to 1,000 mg.

In one embodiment, for any of the methods of the application disclosed herein, the therapeutically effective amount of Compound I is administered to the subject once a day, twice a day, three times a day, four times a day, once every two days, once every three days, once every four days, once every five days, once every six days, once a week, once every two weeks, once every three weeks, or once a month.

In one embodiment, for any of the methods of the application disclosed herein, Compound I is formulated as a pharmaceutical composition comprising one or more pharmaceutically acceptable excipients. In one embodiment, the pharmaceutical composition further comprises an additional therapeutic agent for the treatment of pain.

In one embodiment, for any of the methods of the application disclosed herein, Compound I, or a pharmaceutically acceptable salt, solvate, or prodrug thereof, or the pharmaceutical composition comprising Compound I, or a pharmaceutically acceptable salt, solvate, or prodrug thereof, is administered orally, parenterally, intravenously, intramuscularly, intrathecally, subcutaneously, topically, systemically, cutaneously, sublingually, buccally, rectally, vaginally, ocularly, otically, nasally, by inhalation, by nebulization, or transdermally.

In one embodiment, for any of the methods of the application disclosed herein, Compound I, or a pharmaceutically acceptable salt, solvate, or prodrug thereof, or the pharmaceutical composition comprising Compound I, or a pharmaceutically acceptable salt, solvate, or prodrug thereof, is administered to the subject orally and is formulated as a tablet, capsule, chew, gel, paste, multi-particulate, nanoparticulate, lozenge, pastille, granule, powder, solution, spray, emulsion, suspension, syrup, mouthwash, or drop.

In one embodiment, for any of the methods of the application disclosed herein, Compound I, or a pharmaceutically acceptable salt, solvate, or prodrug thereof, or a pharmaceutical composition comprising Compound I, or a pharmaceutically acceptable salt, solvate, or prodrug thereof, is administered to the subject topically and is formulated as a cream, paste, lotion, gel, patch, or spray.

In one embodiment, for any of the methods of the application disclosed herein, the method further comprises administering an additional therapeutic agent for the treatment of pain. In one embodiment, the additional therapeutic agent and Compound I, or a pharmaceutical composition comprising Compound I, are administered in temporal proximity.

In one embodiment, for any of the methods of the application disclosed herein, the subject is a human.

In one embodiment, for any of the methods of the application disclosed herein, upon improvement in the subject's pain, fibromyalgia, neuropathy, or chemotherapy-induced pain, upon promotion of an antihyperalgesic effect in the subject, or upon a reduction in the subject's sensitivity to pain, the subject is then administered a maintenance dose of Compound I and/or an additional therapeutic agent for the treatment of pain. In one embodiment, the maintenance dose of Compound I and/or the additional therapeutic agent is lower than the induction dose, administered less frequently than the induction dose, or lower than the induction dose and administered less frequently than the induction dose.

In one embodiment, for any of the methods of the application disclosed herein, Compound I is a hydrochloride salt.

In one aspect, this application pertains to a pharmaceutical composition comprising Compound I,

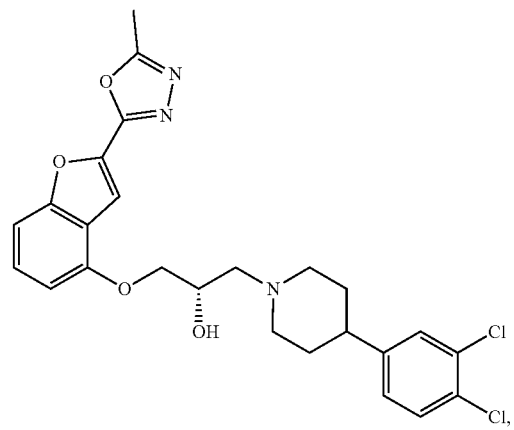 [SMILES: Cc1nnc(-c2cc3c(OC[C@@H](O)CN4CCC(c5ccc(Cl)c(Cl)c5)CC4)cccc3o2)o1]

or a pharmaceutically acceptable salt, solvate, or prodrug thereof, for use in treating or preventing pain in a subject in need of treatment.

In one aspect, this application pertains to a pharmaceutical composition comprising Compound I,

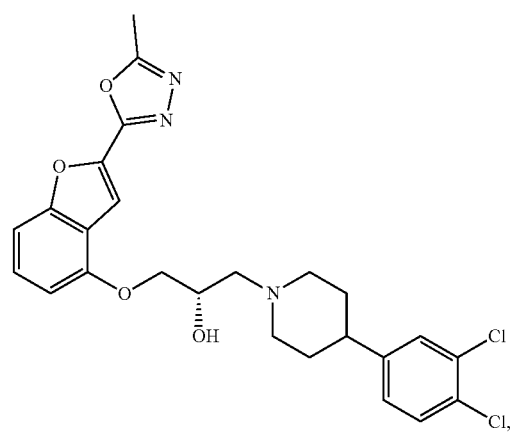 [SMILES: Cc1nnc(-c2cc3c(OC[C@@H](O)CN4CCC(c5ccc(Cl)c(Cl)c5)CC4)cccc3o2)o1]

or a pharmaceutically acceptable salt, solvate, or prodrug thereof, for use in treating pain in a subject in need of treatment.

In one aspect, this application pertains to a pharmaceutical composition comprising Compound I,

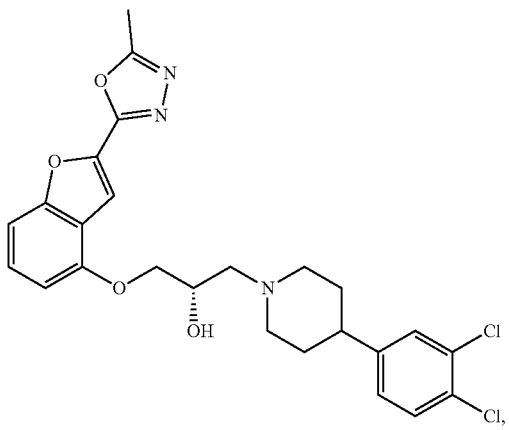 [SMILES: Cc1nnc(-c2cc3c(OC[C@@H](O)CN4CCC(c5ccc(Cl)c(Cl)c5)CC4)cccc3o2)o1]

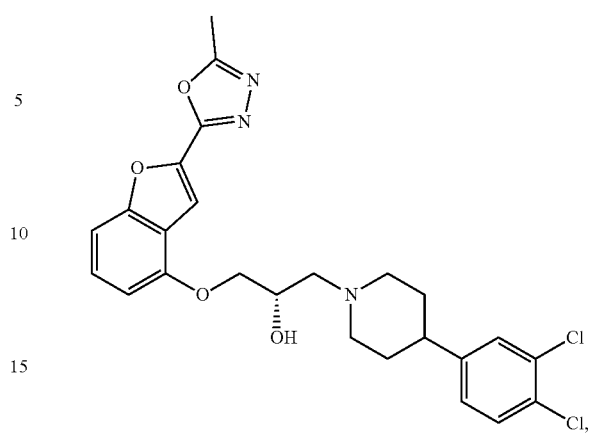

or a pharmaceutically acceptable salt, solvate, or prodrug thereof, for use in preventing pain in a subject in need of treatment.

In one embodiment, the pain is acute pain, chronic pain, toxic pain, neuropathic pain, nociceptive pain, inflammatory pain, post-operative pain, visceral pain, chemotherapy-induced pain, or a combination thereof.

In one embodiment, the pain is peripheral neuropathy.

In one embodiment, the pain is peripheral neuropathy that is peripheral mononeuropathy.

In one embodiment, the pain is peripheral neuropathy that is peripheral polyneuropathy.

In one embodiment, the pain is chemotherapy-induced peripheral neuropathy.

In one embodiment, the pain is chemotherapy-induced peripheral neuropathy, wherein the chemotherapy is paclitaxel.

In one aspect, this application pertains to a pharmaceutical composition comprising Compound I, or a pharmaceutically acceptable salt, solvate, or prodrug thereof, for use in treating or preventing neuropathy in a subject in need of treatment.

In one embodiment, the neuropathy is peripheral neuropathy.

In one embodiment, the neuropathy is peripheral mononeuropathy.

In one embodiment, the neuropathy is peripheral polyneuropathy.

In one embodiment, the neuropathy is induced by chemotherapy.

In one aspect, this application pertains to a pharmaceutical composition comprising Compound I,

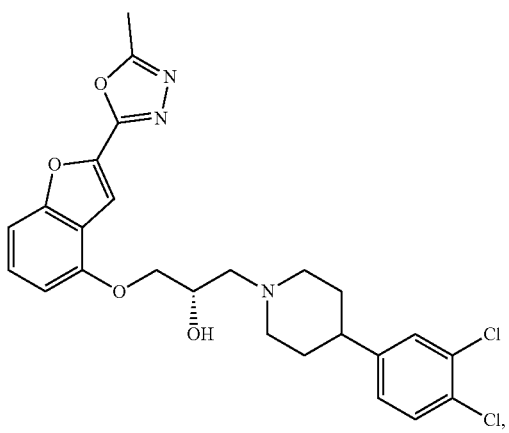 [SMILES: Cc1nnc(-c2cc3c(OC[C@@H](O)CN4CCC(c5ccc(Cl)c(Cl)c5)CC4)cccc3o2)o1]

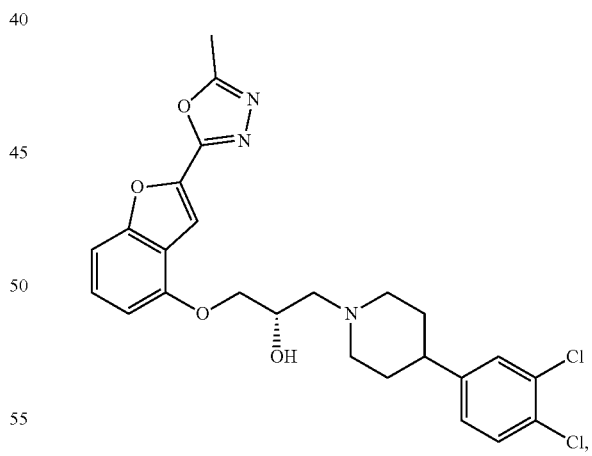

or a pharmaceutically acceptable salt, solvate, or prodrug thereof, for use in treating or preventing fibromyalgia in a subject in need of treatment.

In one aspect, this application pertains to a pharmaceutical composition comprising Compound I, or a pharmaceutically acceptable salt, solvate, or prodrug thereof, for use in treating or preventing chemotherapy-induced pain in a subject in need of treatment.

In one embodiment, the chemotherapy-induced pain is peripheral neuropathic pain.

In one embodiment, the chemotherapy is paclitaxel.

In one aspect, this application pertains to a pharmaceutical composition comprising Compound I,

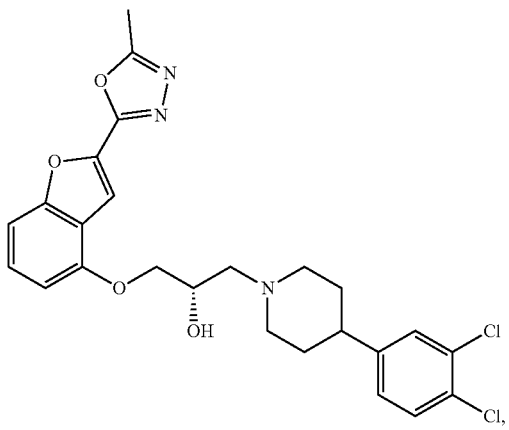 [SMILES: Cc1nnc(-c2cc3c(OC[C@@H](O)CN4CCC(c5ccc(Cl)c(Cl)c5)CC4)cccc3o2)o1]

or a pharmaceutically acceptable salt, solvate, or prodrug thereof, for use in promoting an antihyperalgesic effect in a subject suffering from hyperalgesia.

In one aspect, this application pertains to a pharmaceutical composition comprising Compound I,

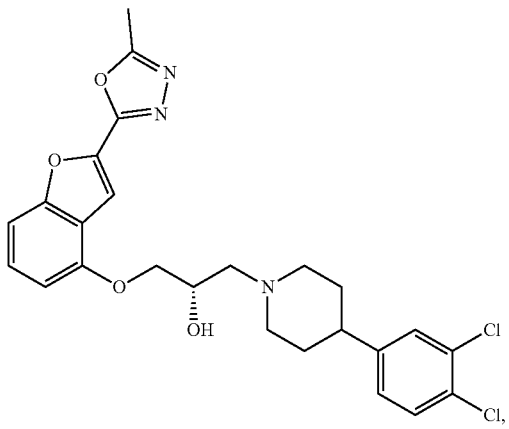 [SMILES: Cc1nnc(-c2cc3c(OC[C@@H](O)CN4CCC(c5ccc(Cl)c(Cl)c5)CC4)cccc3o2)o1]

or a pharmaceutically acceptable salt, solvate, or prodrug thereof, for use in reducing sensitivity to pain in a subject.

In one embodiment, for any of the uses of the application disclosed herein, the therapeutically effective amount of the pharmaceutical composition comprising Compound I is 0.1 mg/kg to 100 mg/kg.

In one embodiment, for any of the uses of the application disclosed herein, the therapeutically effective amount of the pharmaceutical composition comprising Compound I is about 10 mg/kg.

In one embodiment, for any of the uses of the application disclosed herein, the therapeutically effective amount of the pharmaceutical composition comprising Compound I is 1 mg to 1,000 mg.

In one embodiment, for any of the uses of the application disclosed herein, the therapeutically effective amount of the pharmaceutical composition comprising Compound I is administered to the subject once a day, twice a day, three times a day, four times a day, once every two days, once every three days, once every four days, once every five days, once every six days, once a week, once every two weeks, once every three weeks, or once a month.

In one embodiment, for any of the uses of the application disclosed herein, the pharmaceutical composition comprising Compound I is formulated with one or more pharmaceutically acceptable excipients. In one embodiment, the pharmaceutical composition further comprises an additional therapeutic agent for the treatment of pain.

In one embodiment, for any of the uses of the application disclosed herein, the pharmaceutical composition comprising Compound I, or a pharmaceutically acceptable salt, solvate, or prodrug thereof, is formulated for oral, parenteral, intravenous, intramuscular, intrathecal, subcutaneous, topical, systemic, cutaneous, sublingual, buccal, rectal, vaginal, ocular, otic, nasal, or transdermal administration, or for inhalation or nebulization.

In one embodiment, for any of the uses of the application disclosed herein, the pharmaceutical composition comprising Compound I, or a pharmaceutically acceptable salt, solvate, or prodrug thereof, is formulated for oral administration as a tablet, capsule, chew, gel, paste, multi-particulate, nanoparticulate, lozenge, pastille, granule, powder, solution, spray, emulsion, suspension, syrup, mouthwash, or drop.

In one embodiment, for any of the uses of the application disclosed herein, the pharmaceutical composition comprising Compound I, or a pharmaceutically acceptable salt, solvate, or prodrug thereof, is formulated for topical administration as a cream, paste, lotion, gel, patch, or spray.

In one embodiment, for any of the uses of the application disclosed herein, the use further comprises an additional therapeutic agent for the treatment of pain. In one embodiment, the additional therapeutic agent and the pharmaceutical composition comprising Compound I are administered in temporal proximity.

In one embodiment, for any of the uses of the application disclosed herein, the subject is a human.

In one embodiment, for any of the uses of the application disclosed herein, upon improvement in the subject's pain, fibromyalgia, neuropathy, or chemotherapy-induced pain, upon promotion of an antihyperalgesic effect in the subject, or upon a reduction in the subject's sensitivity to pain, the subject is then administered a maintenance dose of the pharmaceutical composition comprising Compound I and/or an additional therapeutic agent for the treatment of pain. In one embodiment, the maintenance dose of the pharmaceutical composition comprising Compound I and/or the additional therapeutic agent is lower than the induction dose, administered less frequently than the induction dose, or lower than the induction dose and administered less frequently than the induction dose.

In one embodiment, for any of the uses of the application disclosed herein, Compound I is a hydrochloride salt.

In one aspect, this application pertains to Compound I,

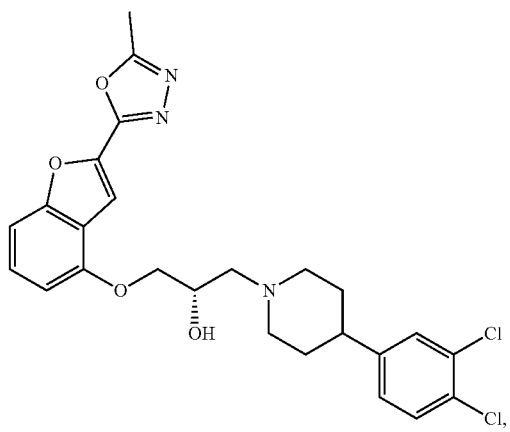 [SMILES: Cc1nnc(-c2cc3c(OC[C@@H](O)CN4CCC(c5ccc(Cl)c(Cl)c5)CC4)cccc3o2)o1]

or a pharmaceutically acceptable salt, solvate, or prodrug thereof, for use in treating or preventing pain in a subject in need of treatment.

In one aspect, this application pertains to Compound I,

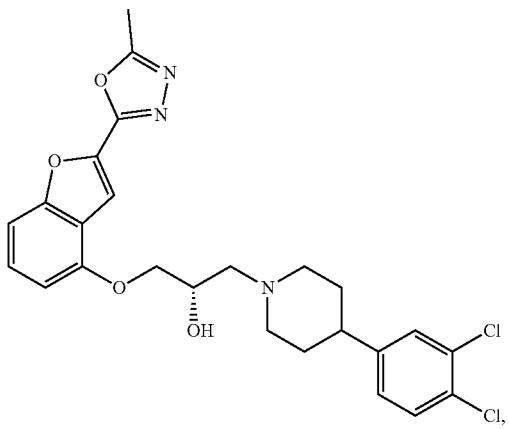 [SMILES: Cc1nnc(-c2cc3c(OC[C@@H](O)CN4CCC(c5ccc(Cl)c(Cl)c5)CC4)cccc3o2)o1]

or a pharmaceutically acceptable salt, solvate, or prodrug thereof, for use in treating pain in a subject in need of treatment.

In one aspect, this application pertains to Compound I,

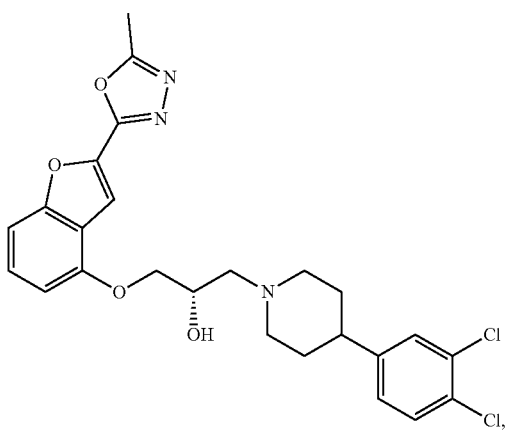 [SMILES: Cc1nnc(-c2cc3c(OC[C@@H](O)CN4CCC(c5ccc(Cl)c(Cl)c5)CC4)cccc3o2)o1]

or a pharmaceutically acceptable salt, solvate, or prodrug thereof, for use in preventing pain in a subject in need of treatment.

In one embodiment, the pain is acute pain, chronic pain, toxic pain, neuropathic pain, nociceptive pain, inflammatory pain, post-operative pain, visceral pain, chemotherapy-induced pain, or a combination thereof.

In one embodiment, the pain is peripheral neuropathy.

In one embodiment, the pain is peripheral neuropathy that is peripheral mononeuropathy.

In one embodiment, the pain is peripheral neuropathy that is peripheral polyneuropathy.

In one embodiment, the pain is chemotherapy-induced peripheral neuropathy.

In one embodiment, the pain is chemotherapy-induced peripheral neuropathy, wherein the chemotherapy is paclitaxel.

In one aspect, this application pertains to Compound I,

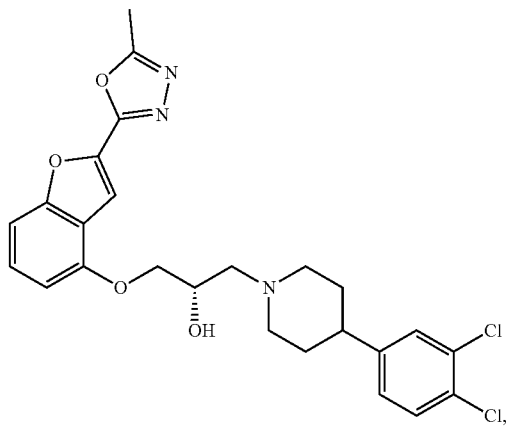 [SMILES: Cc1nnc(-c2cc3c(OC[C@@H](O)CN4CCC(c5ccc(Cl)c(Cl)c5)CC4)cccc3o2)o1]

or a pharmaceutically acceptable salt, solvate, or prodrug thereof, for use in treating or preventing fibromyalgia in a subject in need of treatment.

In one aspect, this application pertains to Compound I,

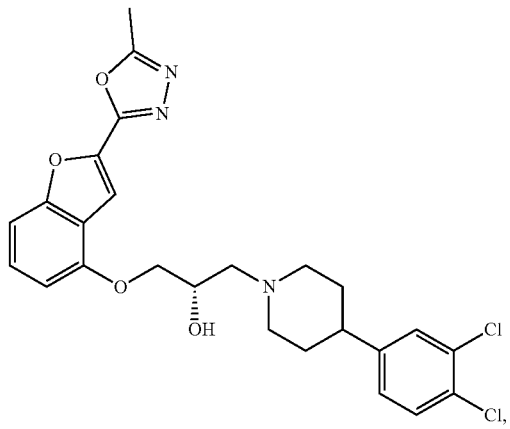 [SMILES: Cc1nnc(-c2cc3c(OC[C@@H](O)CN4CCC(c5ccc(Cl)c(Cl)c5)CC4)cccc3o2)o1]

or a pharmaceutically acceptable salt, solvate, or prodrug thereof, for use in treating or preventing neuropathy in a subject in need of treatment.

In one embodiment, the neuropathy is peripheral neuropathy.

In one embodiment, the neuropathy is peripheral mononeuropathy.

In one embodiment, the neuropathy is peripheral polyneuropathy.

In one embodiment, the neuropathy is induced by chemotherapy.

In one aspect, this application pertains to Compound I,

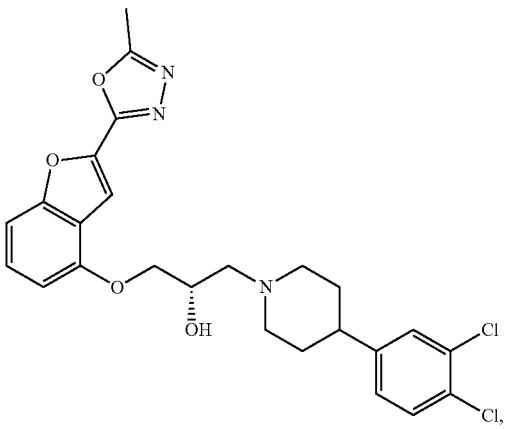 [SMILES: Cc1nnc(-c2cc3c(OC[C@@H](O)CN4CCC(c5ccc(Cl)c(Cl)c5)CC4)cccc3o2)o1]

or a pharmaceutically acceptable salt, solvate, or prodrug thereof, for use in treating or preventing chemotherapy-induced pain in a subject in need of treatment.

In one embodiment, the chemotherapy-induced pain is peripheral neuropathic pain.

In one embodiment, the chemotherapy is paclitaxel.

In one aspect, this application pertains to Compound I,

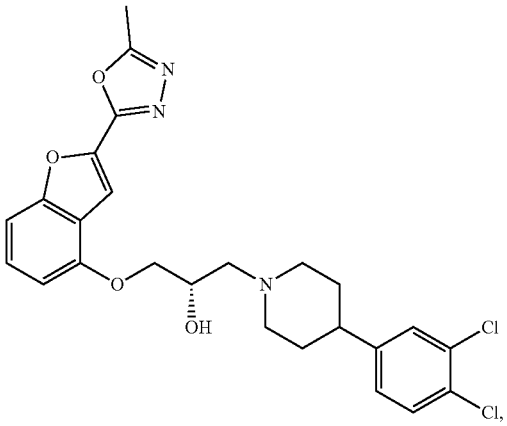 [SMILES: Cc1nnc(-c2cc3c(OC[C@@H](O)CN4CCC(c5ccc(Cl)c(Cl)c5)CC4)cccc3o2)o1]

or a pharmaceutically acceptable salt, solvate, or prodrug thereof, for use in promoting an antihyperalgesic effect in a subject suffering from hyperalgesia.

In one aspect, this application pertains to Compound I,

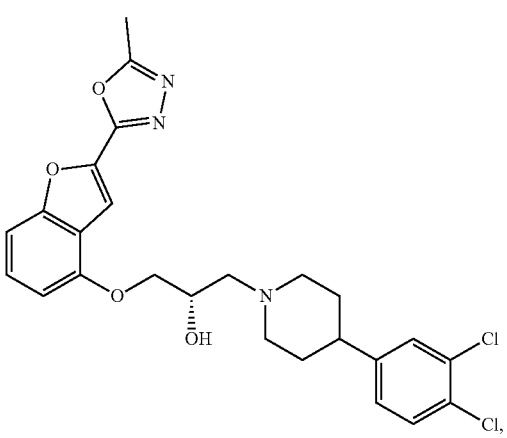 [SMILES: Cc1nnc(-c2cc3c(OC[C@@H](O)CN4CCC(c5ccc(Cl)c(Cl)c5)CC4)cccc3o2)o1]

or a pharmaceutically acceptable salt, solvate, or prodrug thereof, for use in reducing sensitivity to pain in a subject.

In one embodiment, for any of the uses of the application disclosed herein, the therapeutically effective amount of Compound I is 0.1 mg/kg to 100 mg/kg.

In one embodiment, for any of the uses of the application disclosed herein, the therapeutically effective amount of Compound I is about 10 mg/kg.

In one embodiment, for any of the uses of the application disclosed herein, the therapeutically effective amount of Compound I is 1 mg to 1,000 mg.

In one embodiment, for any of the uses of the application disclosed herein, the therapeutically effective amount of Compound I is administered to the subject once a day, twice a day, three times a day, four times a day, once every two days, once every three days, once every four days, once every five days, once every six days, once a week, once every two weeks, once every three weeks, or once a month.

In one embodiment, for any of the uses of the application disclosed herein, Compound I is formulated with one or more pharmaceutically acceptable excipients. In one embodiment, Compound I is formulated with one or more pharmaceutically acceptable excipients and an additional therapeutic agent for the treatment of pain.

In one embodiment, for any of the uses of the application disclosed herein, Compound I, or a pharmaceutically acceptable salt, solvate, or prodrug thereof, is formulated for oral, parenteral, intravenous, intramuscular, intrathecal, subcutaneous, topical, systemic, cutaneous, sublingual, buccal, rectal, vaginal, ocular, otic, nasal, or transdermal administration, or for inhalation or nebulization.

In one embodiment, for any of the uses of the application disclosed herein, Compound I, or a pharmaceutically acceptable salt, solvate, or prodrug thereof, is formulated for oral administration as a tablet, capsule, chew, gel, paste, multiparticulate, nanoparticulate, lozenge, pastille, granule, powder, solution, spray, emulsion, suspension, syrup, mouthwash, or drop.

In one embodiment, for any of the uses of the application disclosed herein, Compound I, or a pharmaceutically acceptable salt, solvate, or prodrug thereof, is formulated for topical administration as a cream, paste, lotion, gel, patch, or spray.

In one embodiment, for any of the uses of the application disclosed herein, the use further comprises an additional therapeutic agent for the treatment of pain. In one embodiment, the additional therapeutic agent and Compound I are administered in temporal proximity.

In one embodiment, for any of the uses of the application disclosed herein, the subject is a human.

In one embodiment, for any of the uses of the application disclosed herein, upon improvement in the subject's pain, fibromyalgia, neuropathy, or chemotherapy-induced pain, upon promotion of an antihyperalgesic effect in the subject, or upon a reduction in the subject's sensitivity to pain, the subject is then administered a maintenance dose of Compound I and/or an additional therapeutic agent for the treatment of pain. In one embodiment, the maintenance dose of Compound I and/or the additional therapeutic agent is lower than the induction dose, administered less frequently than the induction dose, or lower than the induction dose and administered less frequently than the induction dose.

In one embodiment, for any of the uses of the application disclosed herein, Compound I is a hydrochloride salt.

In one aspect, this application pertains to Compound I,

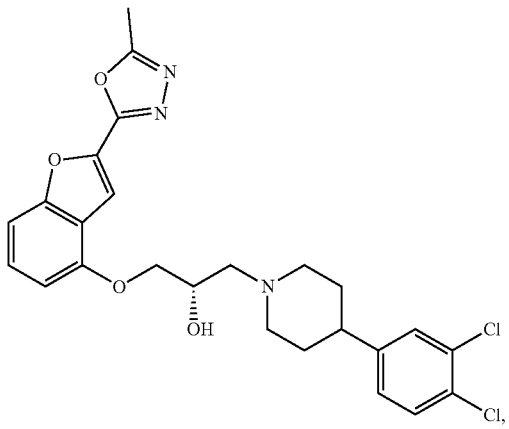 [SMILES: Cc1nnc(-c2cc3c(OC[C@@H](O)CN4CCC(c5ccc(Cl)c(Cl)c5)CC4)cccc3o2)o1]

or a pharmaceutically acceptable salt, solvate, or prodrug thereof, for use in the manufacture of a medicament for treating or preventing pain in a subject in need of treatment.

In one aspect, this application pertains to Compound I,

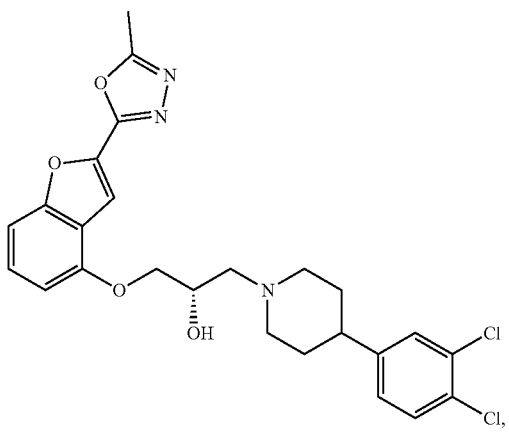 [SMILES: Cc1nnc(-c2cc3c(OC[C@@H](O)CN4CCC(c5ccc(Cl)c(Cl)c5)CC4)cccc3o2)o1]

or a pharmaceutically acceptable salt, solvate, or prodrug thereof, for use in the manufacture of a medicament for treating pain in a subject in need of treatment.

In one aspect, this application pertains to Compound I,

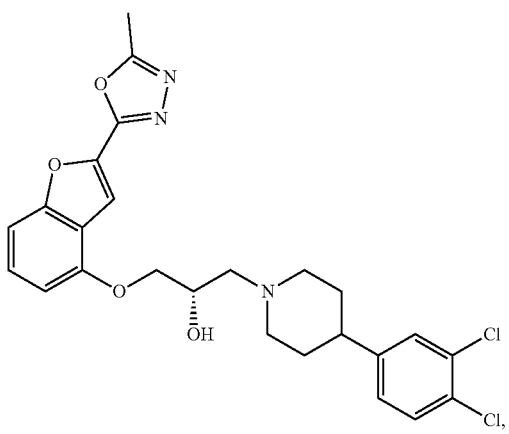 [SMILES: Cc1nnc(-c2cc3c(OC[C@@H](O)CN4CCC(c5ccc(Cl)c(Cl)c5)CC4)cccc3o2)o1]

or a pharmaceutically acceptable salt, solvate, or prodrug thereof, for use in the manufacture of a medicament for preventing pain in a subject in need of treatment.

In one embodiment, the pain is acute pain, chronic pain, toxic pain, neuropathic pain, nociceptive pain, inflammatory pain, post-operative pain, visceral pain, chemotherapy-induced pain, or a combination thereof.

In one embodiment, the pain is peripheral neuropathy.

In one embodiment, the pain is peripheral neuropathy that is peripheral mononeuropathy.

In one embodiment, the pain is peripheral neuropathy that is peripheral polyneuropathy.

In one embodiment, the pain is chemotherapy-induced peripheral neuropathy.

In one embodiment, the pain is chemotherapy-induced peripheral neuropathy, wherein the chemotherapy is paclitaxel.

In one aspect, this application pertains to Compound I,

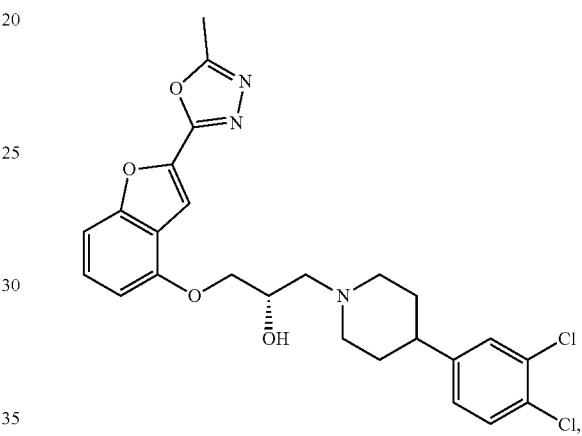

or a pharmaceutically acceptable salt, solvate, or prodrug thereof, for use in the manufacture of a medicament for treating or preventing fibromyalgia in a subject in need of treatment.

In one aspect, this application pertains to Compound I,

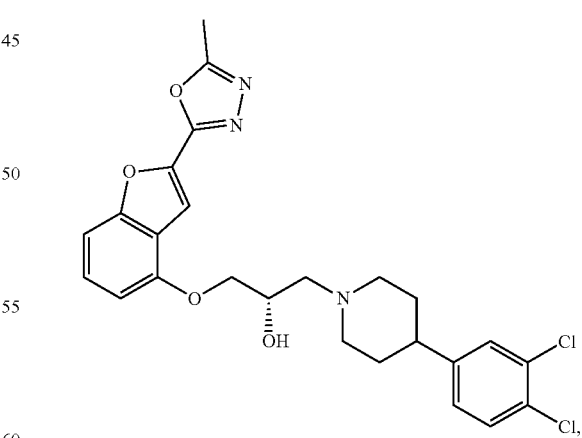

or a pharmaceutically acceptable salt, solvate, or prodrug thereof, for use in the manufacture of a medicament for treating or preventing neuropathy in a subject in need of treatment.

In one embodiment, the neuropathy is peripheral neuropathy.

In one embodiment, the neuropathy is peripheral mononeuropathy.

In one embodiment, the neuropathy is peripheral polyneuropathy.

In one embodiment, the neuropathy is induced by chemotherapy.

In one aspect, this application pertains to Compound I,

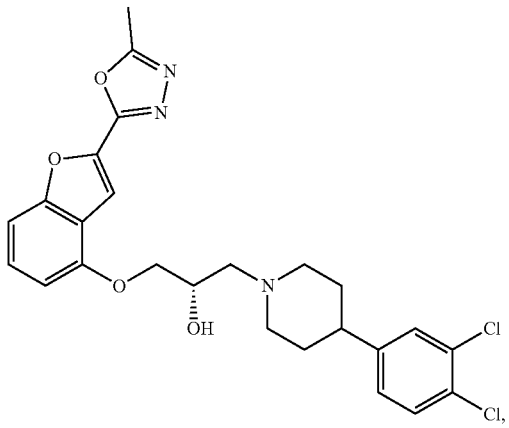 [SMILES: Cc1nnc(-c2cc3c(OC[C@@H](O)CN4CCC(c5ccc(Cl)c(Cl)c5)CC4)cccc3o2)o1]

or a pharmaceutically acceptable salt, solvate, or prodrug thereof, for use in the manufacture of a medicament for treating or preventing chemotherapy-induced pain in a subject in need of treatment.

In one embodiment, the chemotherapy-induced pain is peripheral neuropathic pain.

In one embodiment, the chemotherapy is paclitaxel.

In one aspect, this application pertains to Compound I,

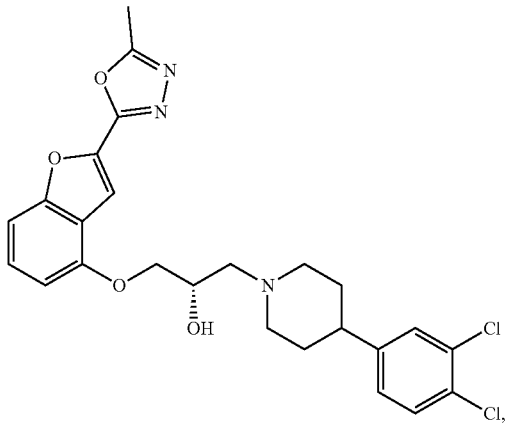 [SMILES: Cc1nnc(-c2cc3c(OC[C@@H](O)CN4CCC(c5ccc(Cl)c(Cl)c5)CC4)cccc3o2)o1]

or a pharmaceutically acceptable salt, solvate, or prodrug thereof, for use in the manufacture of a medicament for promoting an antihyperalgesic effect in a subject suffering from hyperalgesia.

In one aspect, this application pertains to Compound I,

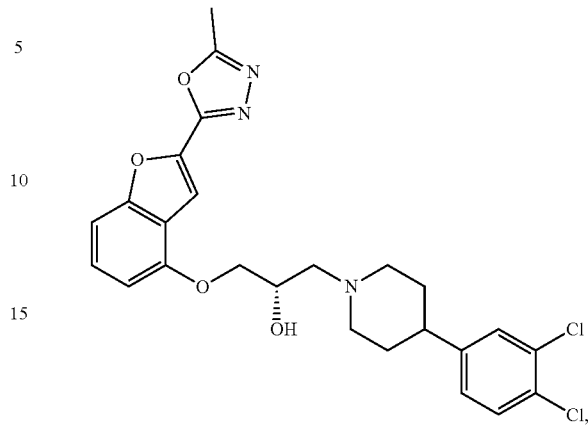

or a pharmaceutically acceptable salt, solvate, or prodrug thereof, for use in the manufacture of a medicament for reducing sensitivity to pain in a subject.

In one embodiment, for any of the uses of the application disclosed herein, the therapeutically effective amount of the medicament comprising Compound I is 0.1 mg/kg to 100 mg/kg.

In one embodiment, for any of the uses of the application disclosed herein, the therapeutically effective amount of the medicament comprising Compound I is about 10 mg/kg.

In one embodiment, for any of the uses of the application disclosed herein, the therapeutically effective amount of the medicament comprising Compound I is 1 mg to 1,000 mg.

In one embodiment, for any of the uses of the application disclosed herein, the medicament comprising Compound I is administered to the subject once a day, twice a day, three times a day, four times a day, once every two days, once every three days, once every four days, once every five days, once every six days, once a week, once every two weeks, once every three weeks, or once a month.

In one embodiment, for any of the uses of the application disclosed herein, the medicament is formulated with one or more pharmaceutically acceptable excipients. In one embodiment, the medicament further comprises an additional therapeutic agent for the treatment of pain.

In one embodiment, for any of the uses of the application disclosed herein, the medicament comprising Compound I, or a pharmaceutically acceptable salt, solvate, or prodrug thereof, is formulated for oral, parenteral, intravenous, intramuscular, intrathecal, subcutaneous, topical, systemic, cutaneous, sublingual, buccal, rectal, vaginal, ocular, otic, nasal, or transdermal administration, or for inhalation or nebulization.

In one embodiment, for any of the uses of the application disclosed herein, the medicament comprising Compound I, or a pharmaceutically acceptable salt, solvate, or prodrug thereof, is formulated for oral administration as a tablet, capsule, chew, gel, paste, multi-particulate, nanoparticulate, lozenge, pastille, granule, powder, solution, spray, emulsion, suspension, syrup, mouthwash, or drop.

In one embodiment, for any of the uses of the application disclosed herein, the medicament comprising Compound I, or a pharmaceutically acceptable salt, solvate, or prodrug thereof, is formulated for topical administration as a cream, paste, lotion, gel, patch, or spray.

In one embodiment, for any of the uses of the application disclosed herein, the use further comprises an additional therapeutic agent for the treatment of pain. In one embodiment, the additional therapeutic agent and the medicament comprising Compound I are administered in temporal proximity.

In one embodiment, for any of the uses of the application disclosed herein, the subject is a human.

In one embodiment, for any of the uses of the application disclosed herein, upon improvement in the subject's pain, fibromyalgia, neuropathy, or chemotherapy-induced pain, upon promotion of an antihyperalgesic effect in the subject, or upon a reduction in the subject's sensitivity to pain, the subject is then administered a maintenance dose of the medicament comprising Compound I and/or an additional therapeutic agent for the treatment of pain. In one embodiment, the maintenance dose of the medicament comprising Compound I and/or the additional therapeutic agent is lower than the induction dose, administered less frequently than the induction dose, or lower than the induction dose and administered less frequently than the induction dose.

In one embodiment, for any of the uses of the application disclosed herein, Compound I is a hydrochloride salt.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Other methods and features will become apparent to those skilled in the art upon examination of the following drawings and detailed description. It is intended that all such methods and features be included within this description, be within the scope of the present invention, and be protected by the accompanying claims.

DETAILED DESCRIPTION

Figure 1:
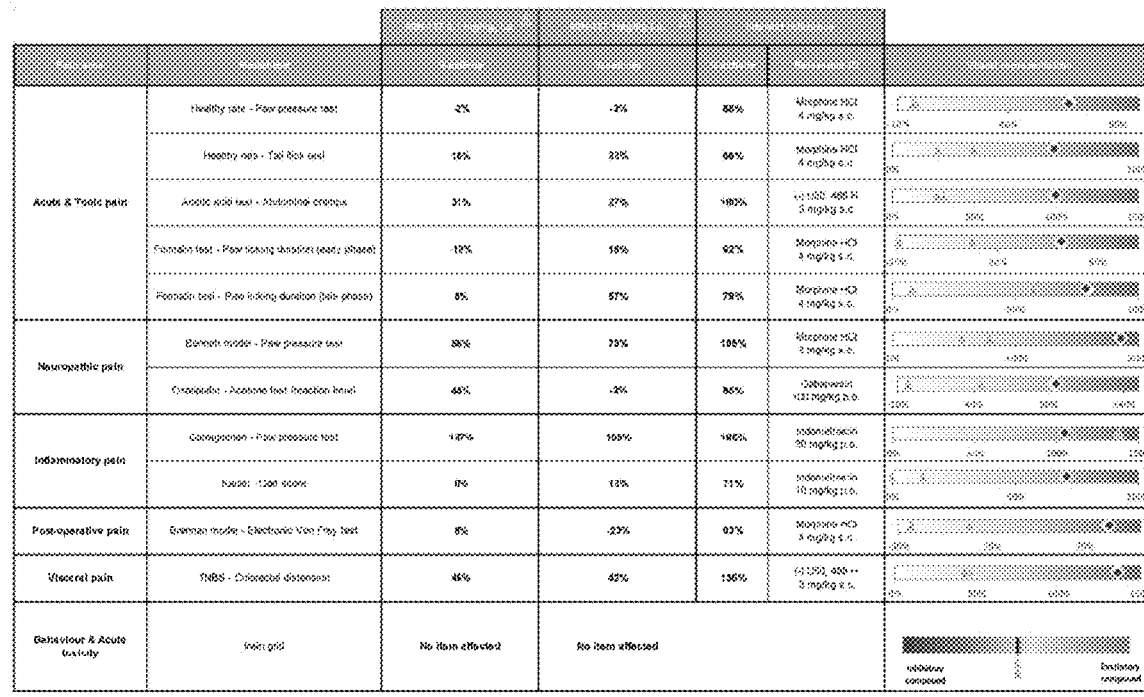
FIG. 1 summarizes the results of the effect of a single administration of MIN-117 at 0.1 mg/kg and 1 mg/kg doses intraperitoneal (i.p.) in ALGOGram™.

All definitions, as defined and used herein, should be understood to control over dictionary definitions, definitions in documents incorporated by reference, and/or ordinary meanings of the defined terms.

The term "about," as used herein, and unless explicitly stated otherwise, refers to a recited value +/−10%, +/−5%, +/−2.5%, +/−1%, +/−0.5%, or +/−0%. For example, "about" may refer to a recited value +/−5%. Alternatively, in another embodiment, "about" may refer to a recited value +/−0%.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein, phrases containing the term "and/or" such as "A, B and/or C" refer to any of the following: A only; B only; C only; A and B; A and C; B and C; A, B and C.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

"Prodrug", as used herein means a compound which is convertible in vivo by metabolic means (e.g., by hydrolysis) to afford any compound delineated by the formulae of the instant application. Various forms of prodrugs are known in the art, for example, as discussed in Bundgaard, (ed.), Design of Prodrugs, Elsevier (1985); Widder, et al., (ed.), Methods in Enzymology, vol. 4, Academic Press (1985); Krogsgaard-Larsen, et al., (ed). Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

The term "pharmaceutically acceptable prodrugs" as used herein refers to those prodrugs of Compound I, or a pharmaceutically acceptable salt or solvate thereof, which are, within the scope of sound medical judgment, suitable for use in contact with the tissues of humans and lower animals with undue toxicity, irritation, allergic response, and the like, commensurate with a reasonable benefit/risk ratio, and effective for their intended use.

In one embodiment, "pharmaceutically acceptable prodrugs", includes "pharmaceutically acceptable esters".

As used herein, the term "pharmaceutically acceptable ester" refers to an ester of Compound I, or a pharmaceutically acceptable salt or solvate thereof, which hydrolyzes in vivo and includes those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The phrase "pharmaceutically acceptable excipient" refers to any of the following classes of ingredients: fillers, binders, lubricants, disintegrating agents, glidants (e.g., silicon dioxide), flavoring agents and colorants. Suitable binders include, e.g., microcrystalline cellulose (e.g., Avicel PH200 LM, PH112, PH101, PH102, PH103, PH113, PH105, PH200, DG), mannitol, dicalcium phosphate, dicalcium phosphate anhydrous, povidone, lactose, glucose, starch, gelatin, acacia gum, tragacanth gum, sodium alginate, carboxymethylcellulose, polyethylene glycol, waxes or the like. Lubricants include, e.g., glyceryl dibehenate, hydrogenated vegetable oil, sodium oleate, sodium stearate, magnesium stearate, silicon dioxide, sodium benzoate, sodium acetate, sodium chloride or the like. Other excipients include, e.g., starch, methyl cellulose, agar, bentonite, xanthan gum, sodium starch glycolate, crospovidone, croscarmellose sodium or the like. Additional excipients for capsules include macrogols or lipids and/or any other excipients known in the art.

As used herein, the term "pharmaceutically acceptable salt" refers to those salts of Compound I which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al., describes pharmaceutically acceptable salts in detail in *J. Pharmaceutical Sciences,* 66: 1-19 (1977). The salts can be prepared in situ during the final isolation and purification of Compound I, or separately by reacting with a suitable acid.

"Temporal proximity" means that administration of an additional therapeutic agent occurs within a time period before or after the administration of Compound I, or a pharmaceutically acceptable salt, solvate, or prodrug thereof, such that the therapeutic effect of the additional therapeutic agent or therapy overlaps with the therapeutic effect of Compound I, or a pharmaceutically acceptable salt, solvate, or prodrug thereof. In some embodiments, the therapeutic effect of the additional therapeutic agent completely overlaps with the therapeutic effect of Compound I, or a pharmaceutically acceptable salt, solvate, or prodrug thereof. In some embodiments, "temporal proximity" means that administration of the additional therapeutic agent occurs within a time period before or after the administration of Compound I, or a pharmaceutically acceptable salt, solvate, or prodrug thereof, such that there is a synergistic effect between the additional therapeutic agent and Compound I, or a pharmaceutically acceptable salt, solvate, or prodrug thereof.

"Temporal proximity" may vary according to various factors, including but not limited to, the age, gender, weight, genetic background, medical condition, disease history, and treatment history of the subject to which the therapeutic agents are to be administered; the disease or condition to be treated or ameliorated; the therapeutic outcome to be achieved; the dosage, dosing frequency, and dosing duration of the therapeutic agents; the pharmacokinetics and pharmacodynamics of the therapeutic agents; and the route(s) through which the therapeutic agents are administered. In some embodiments, "temporal proximity" means within 15 minutes, within 30 minutes, within an hour, within two hours, within four hours, within six hours, within eight hours, within 12 hours, within 18 hours, within 24 hours, within 36 hours, within 2 days, within 3 days, within 4 days, within 5 days, within 6 days, within a week, within 2 weeks, within 3 weeks, within 4 weeks, with 6 weeks, or within 8 weeks. In some embodiments, multiple administration of one therapeutic agent can occur in temporal proximity to a single administration of another therapeutic agent. In some embodiments, temporal proximity may change during a treatment cycle or within a dosing regimen.

As used herein interchangeably, the terms "controlled-release" or "sustained-release" refer to pharmaceutical compositions which are prepared in a way designed to release one or more active compounds at a predetermined rate. The active compound(s) can be prepared with pharmaceutically acceptable carriers that will protect the compound against rapid absorption or rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, which is incorporated by reference herein in its entirety.

The phrase, "therapeutically effective amount" or "effective amount" as used herein indicates an amount necessary to administer to a subject, or to a cell, tissue, or organ of a subject, to achieve a therapeutic effect, such as an ameliorating or alternatively a curative effect.

In one aspect, the therapeutically effective amount of Compound I, or a pharmaceutically acceptable salt, solvate, or prodrug thereof, is the amount necessary to treat pain in a subject.

In one aspect, the therapeutically effective amount of Compound I, or a pharmaceutically acceptable salt, solvate, or prodrug thereof, is the amount necessary to prevent pain in a subject.

In one aspect, the therapeutically effective amount of Compound I, or a pharmaceutically acceptable salt, solvate, or prodrug thereof, is the amount necessary to ameliorate pain in a subject.

In one aspect, the therapeutically effective amount of Compound I, or a pharmaceutically acceptable salt, solvate, or prodrug thereof, is the amount necessary to eliminate pain in a subject.

In one aspect, the therapeutically effective amount of Compound I, or a pharmaceutically acceptable salt, solvate, or prodrug thereof, is the amount necessary to lessen the symptoms of pain in a subject.

In one aspect, the therapeutically effective amount of Compound I, or a pharmaceutically acceptable salt, solvate, or prodrug thereof, is the amount necessary to treat, prevent, eliminate, or lessen fibromyalgia or the symptoms of fibromyalgia in a subject.

In one aspect, the therapeutically effective amount of Compound I, or a pharmaceutically acceptable salt, solvate, or prodrug thereof, is the amount necessary to treat, prevent, eliminate, or lessen neuropathy or the symptoms of neuropathy in a subject.

In one aspect, the therapeutically effective amount of Compound I, or a pharmaceutically acceptable salt, solvate, or prodrug thereof, is the amount necessary to treat, prevent, eliminate, or lessen chemotherapy-induced pain in a subject.

In one aspect, the therapeutically effective amount of Compound I, or a pharmaceutically acceptable salt, solvate, or prodrug thereof, is the amount necessary to promote an antihyperalgesic effect in a subject suffering from hyperalgesia.

In one aspect, the therapeutically effective amount of Compound I, or a pharmaceutically acceptable salt, solvate, or prodrug thereof, is the amount necessary to reduce sensitivity to pain in a subject.

The term, "subject" as used herein refers to any warm-blooded animal such as, but not limited to, a mouse, rat, guinea pig, dog, cat, horse, or human. In one embodiment, the subject is a human.

In one embodiment, the subject is in a "fasted condition" or a "fasted state". "Fasted condition" or a "fasted state" as used to describe a subject means the subject has not eaten for at least 4 hours before a time point of interest, such as the time of administering Compound I. In an embodiment, a subject in the fasted state has not eaten for at least any of 6, 8, 10 or 12 hours prior to administration of Compound I.

In one embodiment, the subject is in a "fed condition" or a "fed state". "Fed condition" or "fed state" as used to describe a subject herein means the subject has eaten less than 4 hours before a time point of interest, such as the time of administering Compound I. In an embodiment, a subject in the fed state has not eaten for at least any of 3, 2, 1 or 0.5 hours prior to administration of Compound I.

The phrase "therapeutic agent for the treatment of pain," as used herein, refers to any agent other than Compound I, or a pharmaceutically acceptable salt, solvate, or prodrug thereof, used in the treatment and/or prevention of any of the types of pain disclosed herein.

In one embodiment, Compound I and the additional therapeutic agent for the treatment of pain are formulated as a single pharmaceutical composition further comprising one or more pharmaceutically acceptable excipients.

In one embodiment, any of the methods disclosed herein further comprise administration to the subject in need of treatment additional therapeutic agent for the treatment of pain. In one embodiment, Compound I and the additional therapeutic agent for the treatment of pain are administered simultaneously. In one embodiment, Compound I is administered before the additional therapeutic agent for the treatment of pain. In one embodiment, Compound I is administered after the additional therapeutic agent for the treatment of pain. In one embodiment, Compound I and the additional therapeutic agent for the treatment of pain are administered in temporal proximity.

In one embodiment, the additional therapeutic agent for the treatment of pain is an opioid such as morphine, codeine, papaverine, thebaine, and the like; a semi-synthetic opioid such as oxycodone, diamorphine, dihydrocodeine, and the like; a synthetic opioid such as the phenylpyridine derivative, e.g., 6-amino-5-(2,3,5-trichlorophenyl)-pyridine-2-carboxylic acid methylamide, and the like; a phenylpiperidine derivative, e.g., fentanyl, sulfentanil, alfentanil, and the like; a morphinan derivative, e.g., levorphanol, butorphanol, and the like; a diphenylheptane derivative, e.g., methadone, propoxyphene, and the like; a benzomorphan derivative, e.g., pentazocine, phenazocine, and the like; drugs that act at the opiate receptor and/or at monoamine reuptake transporters, i.e., tramadol, and the like; NSAIDs such as aspirin, indomethacin, sulindac, etodolac, tolmetin, ketorolac, nabumetone, diclofenac, ibuprofen, naproxen, fenoprofen, ketoprofen, flurbiprofen, oxaprozin piroxicam, meloxicam, tenoxicam, mefenamic acid, meclofenamic acid, flufenamic acid, and pharmaceutically acceptable salts of the foregoing.

Compound I

Compound I, i.e., (2S)-1-(4-(3,4-dichlorophenyl)piperidin-1-yl)-3-((2-(5-methyl-1,3,4-oxadiazol-2-yl)benzofuran-4-yl)oxy)propan-2-ol, has the following structure:

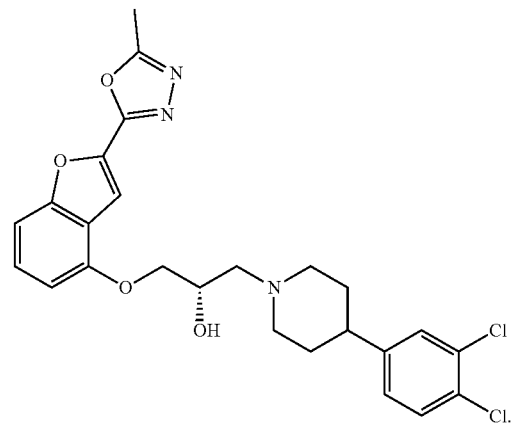 [SMILES: Cc1nnc(-c2cc3c(OC[C@@H](O)CN4CCC(c5ccc(Cl)c(Cl)c5)CC4)cccc3o2)o1]

The monohydrochloride salt of Compound I, i.e., (2S)-1-(4-(3,4-dichlorophenyl)piperidin-1-yl)-3-((2-(5-methyl-1,3,4-oxadiazol-2-yl)benzofuran-4-yl)oxy)propan-2-ol hydrochloride, is also referred to as MIN-117 or MIN117.

Compound I, and salts thereof, including MIN-17, can be prepared according to the methods described in U.S. Pat. Nos. 6,720,320 and 7,196,199, both of which are incorporated herein by reference it their entireties. Additional publications disclosing uses of Compound I, and salts thereof, include US Patent Application Publication Nos. 2014/0206722 and 2019/0183874, both of which are incorporated by reference herein in their entireties.

In one embodiment, Compound I can exist in the form of a pharmaceutically acceptable salt. For example, a monohydrochloride salt (MIN-117).

Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecyl sulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Additionally, Compound I, or a salt of Compound I, can exist as a solvate, meaning solvent addition forms that contain either stoichiometric or non-stoichiometric amounts of solvent. Some compounds have a tendency to trap a fixed molar ratio of solvent molecules in the crystalline solid state, thus forming a solvate. If the solvent is water, the solvate formed is a hydrate; and if the solvent is alcohol, the solvate formed is an alcoholate. Hydrates are formed by the combination of one or more molecules of water with one molecule of the substance in which the water retains its molecular state as $H_2O$ in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc.

Methods of Treatment

In one aspect, this application pertains to methods of treating and preventing pain comprising administering to a subject in need of treatment a therapeutically effective amount of Compound I, or a pharmaceutically acceptable salt, solvate, or prodrug thereof.

In one aspect, this application pertains to methods of treating and preventing pain comprising administering to a subject in need of treatment a therapeutically effective amount of a pharmaceutically acceptable salt of Compound I.

In one aspect, this application pertains to methods of treating and preventing pain comprising administering to a subject in need of treatment a therapeutically effective amount of a hydrochloride salt of Compound I, i.e., MIN-117.

In one embodiment, the pain treated and/or prevented by the methods of this application is acute pain.

Acute pain includes, but is not limited to, nociceptive or inflammatory pain arising from thermal, mechanical, or chemical stimulation of sensory nerve fibers responding to stimuli approaching or exceeding harmful intensity caused by injury and/or visceral pain, including, but not limited to, irritable bowel syndrome (IBS) with or without chronic fatigue syndrome (CFS), inflammatory bowel disease (IBD), Crohn's disease, food poisoning, food allergies, pain associated with gas, hernia, pain associate with gallstones and/or kidney stones, endometriosis, gastroesophageal reflux disease (GERD), appendicitis, interstitial cystitis, deep somatic pain (e.g., sprains, broken bones), neuropathic pain caused by damage or disease affecting the somatosensory nervous system, and superficial somatic pain (e.g., burns).

In one embodiment, the pain treated and/or prevented by the methods of this application is nociceptive pain.

Nociceptive pain includes, but is not limited to, pain arising from physical damage to the body from heat, cold, pressure, pinching, twisting, rubbing, chemicals, among others. Specific examples of nociceptive pain include sprains, bone fractures, burns, bruises, contusions, inflammation, obstructions, and myofascial pain.

In one embodiment, the pain treated and/or prevented by the methods of this application is inflammatory pain.

Inflammatory pain includes, but is not limited to, pain arising from inflammation, including arthritis.

In one embodiment, the pain treated and/or prevented by the methods of this application is visceral pain.

Visceral pain includes, but is not limited to, pain arising from the distension, ischemia, and inflammation of the nociceptors of the thoracic, pelvic, or abdominal organs.

In one embodiment, the pain treated and/or prevented by the methods of this application is chronic, i.e., persistent pain.

Chronic pain includes, but is not limited to, post-operative pain, cancer pain (e.g., chemotherapy-induced pain), degenerative major joint disease pain (e.g., osteoarthritis, rheumatoid arthritis, ankylosing spondylitis, Reiter's syndrome, psoriatic arthritis, gout, pseudogout, infectious arthritis, tendonitis, bursitis, bone lesions, and joint soft tissue inflammation) headaches (e.g., cluster headaches, migraine headaches, tension-type headaches), vascular pain (e.g., arteriosclerosis obliterans, thromboangiitis obliterans, acute arterial occlusion, embolism, congenital arteriovenous aneurysm, vasospastic disease, Raynaud's disease, acrocyanosis, acute venous occlusion, thrombophlebitis, varicose veins, and lymphedema), myofascial or muscle pain (e.g., temporomandibular joint (TMJ) disease/syndrome, chronic musculoskeletal pain, fibromyalgia with or without chronic fatigue syndrome, myofascial pain syndrome or referred pain), neuralgias (trigeminal, postherpetic, glossopharyngeal), shingles, neuropathy, central pain syndrome, complex regional pain syndrome, hyperalgesia, allodynia, central sensitization, peripheral sensitization, disinhibition, and augmented facilitation.

In one embodiment, the pain treated and/or prevented by the methods of this application is chemotherapy induced-pain.

In one embodiment, the pain treated and/or prevented by the methods of this application is post-operative pain.

Post-operative pain includes, but is not limited to, tissue injury together optionally combined with muscle spasm after surgery.

In one embodiment, the pain treated and/or prevented by the methods of this application is fibromyalgia and/or a symptom of fibromyalgia. Fibromyalgia is a disorder characterized by widespread musculoskeletal pain often accompanied by fatigue and/or sleep disorders.

In one embodiment, the pain treated and/or prevented by the methods of this application is fibromyalgia with chronic fatigue syndrome and/or a symptom of fibromyalgia with chronic fatigue syndrome.

In one embodiment, the pain treated and/or prevented by the methods of this application is neuropathic pain, i.e., neuropathy. In one embodiment, neuropathic pain may be caused by damage or disease to any part of the nervous system or somatosensory system. Types of neuropathic pain include, but are not limited to, diabetic neuropathy, peripheral neuropathy, and diabetic peripheral neuropathy, i.e., diabetic peripheral neuropathic pain.

Neuropathic pain caused by damage or disease to any part of the somatosensory system include, but is not limited to, phantom limb pain, multiple chemical sensitivity, sick building syndrome, repetition stress injury, chronic whiplash, chronic lime disease, side effects of silicone breast implants, candidiasis hypersensitivity, the Gulf War Syndrome, food allergies, mitral valve prolapse, and hypoglycemia.

In one embodiment, the pain treated and/or prevented by the methods of this application is diabetic neuropathy, i.e., nerve damage caused by diabetes.

In one embodiment, the pain treated and/or prevented by the methods of this application is peripheral neuropathy, i.e., peripheral neuropathic pain, which is damage or disease affecting sensory, motor, and/or autonomic nerves of the peripheral nervous system.

Peripheral neuropathic pain occurs when peripheral nerves fail to carry information to and from the brain and spinal cord, resulting in pain, loss of sensation, or inability to control muscles. In some cases, the failure of nerves that control blood vessels, intestines, and other organs results in abnormal blood pressure, digestion problems, and loss of other basic body processes. Symptoms also depend on whether the condition affects the whole body or just one nerve. Risk factors for neuropathy include diabetes, heavy alcohol use, exposure to certain chemicals and drugs, prolonged pressure on a nerve. Some people have a hereditary predisposition for peripheral neuropathy.

In one embodiment, the peripheral neuropathy in a subject results from an exposure to toxins, alcohol abuse, malnutrition, diabetes, Guillain-Barre syndrome, or complications from kidney failure, complications from cancer, infections (e.g., AIDS, shingles, Lyme disease), kidney disease, thyroid disease, parathyroid disease, and/or carpal tunnel syndrome.

Causes of peripheral neuropathic pain include, without limitation, neuropathies associated with systemic disease like diabetic neuropathy, neuropathies associated with metabolic conditions like alcoholic neuropathy and burning feet syndrome, neuropathies associated with viral infections like herpes zoster and HIV, neuropathies associated with nutritional deficiencies, neuropathies associated with toxins, neuropathies associated with tumor compression, neuropathies associated with remote manifestations of malignancies, neuropathies associated with drugs like chemotherapy, neuropathies associated with radiation, neuropathies associated with immune mediated disorders, and neuropathies associated with physical trauma to a nerve trunk.

The four cardinal patterns of peripheral neuropathic pain are mononeuropathy, mononeuropathic multiplex, polyneuropathy, and autonomic neuropathy.

In one embodiment, the pain treated and/or prevented by the methods of this application is peripheral neuropathy that is peripheral mononeuropathy. A mononeuropathy is a peripheral neuropathy involving functional loss or pathological change affecting a single nerve or nerve group. Mononeuropathy is most often caused by damage to a local area resulting from injury or trauma, although occasionally systemic disorders may cause isolated nerve damage. The usual causes are direct trauma, prolonged pressure on the nerve, and compression of the nerve by swelling or injury to nearby body structures.

In one embodiment, the damage from a mononeuropathy includes destruction of the myelin sheath (covering) of the nerve or of part of the nerve cell (the axon). This damage slows or prevents conduction of impulses through the nerve. Mononeuropathy may involve any part of the body. Mononeuropathic pain is associated with, e.g., a sciatic nerve dysfunction, a common peroneal nerve dysfunction. a radial nerve dysfunction, an ulnar nerve dysfunction, a cranial mononeuropathy VI, a cranial mononeuropathy VII, a cranial mononeuropathy III (compression type), a cranial mononeuropathy III (diabetic type), an axillary nerve dysfunction, a carpal tunnel syndrome, a femoral nerve dysfunction, a tibial nerve dysfunction, a Bell's palsy, a thoracic outlet syndrome, a carpal tunnel syndrome or other focal entrapment neuropathy, and a sixth (abducent) nerve palsy. For example, the mononeuropathy is ulnar nerve palsy, radial nerve palsy, or peroneal nerve palsy.

In one embodiment, the pain treated and/or prevented by the methods of this application is peripheral neuropathy that is a mononeuropathic multiplex. A mononeuropathic multiplex is a peripheral neuropathy involving functional loss or pathological change that sequentially or simultaneously affects several non-contiguous nerves in an asymmetric manner. A neuropathic pain based on mononeuropathy multiplex may develop over days to years and typically presents with acute or subacute loss of sensory and motor function of individual nerves. The pattern of involvement is asymmetric; however, as the disease progresses deficit(s) becomes more confluent and symmetrical, making it difficult to differentiate from polyneuropathy. Mononeuropathic multiplex may also cause pain characterized as deep, aching pain that is worse at night, and frequently present in the lower back, hip, or leg. Mononeuropathic multiplex may also cause pain characterized as acute, unilateral, severe limb pain followed by anterior muscle weakness and loss of knee reflex. Mononeuropathic multiplex pain is associated with, e.g., diabetes mellitus, infections, such as, e.g., leprosy, lyme disease, HIV, and toxicity.

In one embodiment, the pain treated and/or prevented by the methods of this application is peripheral neuropathy that is peripheral polyneuropathy, which is a peripheral neuropathy involving functional loss or pathological change affecting multiple nerves throughout the body in a symmetric manner. A polyneuropathy may be acute and appear without warning, or chronic and develop gradually over a longer period of time. Many polyneuropathies have both motor and sensory involvement, and some also involve dysfunction of the autonomic nervous system. These disorders are often symmetrical, and usually due to various systematic illnesses and disease processes that affect the peripheral nervous system in its entirety. A polyneuropathy frequently affect the feet and hands, causing weakness, loss of sensation, pins-and-needle sensations or burning pain. Polyneuropathies can be classified in different ways, such as by cause, by speed of progression, or by the parts of the body involved. Classes of polyneuropathy are also distinguished by which part of the nerve cell is mainly affected: the axon, the myelin sheath, or the cell body.

Causes of polyneuropathic pain, include, without limitation, post-polio syndrome, postmastectomy syndrome, diabetic neuropathy, alcohol neuropathy, amyloid, toxins, AIDS, hypothyroidism, uremia, vitamin deficiencies, chemotherapy-induced pain, 2',3'-didexoycytidine (ddC) treatment, Guillain-Barre syndrome, and Fabry's disease.

In one embodiment, the pain treated and/or prevented by the methods of this application is peripheral neuropathy that is an autonomic neuropathy. An autonomic neuropathy is a peripheral neuropathy involving functional loss or pathological change affecting the non-voluntary, non-sensory nervous system (i.e., the autonomic nervous system). Autonomic neuropathy is a form of polyneuropathy which affects mostly the internal organs such as the bladder, muscles, the cardiovascular system, the digestive tract, and the genital organs.

In one embodiment, the treatment and/or prevention of pain in a subject with peripheral and/or diabetic neuropathy includes the reduction in one or more symptoms in the subject selected from the group consisting of tingling, numbness, loss of sensation (e.g., in the arms and/or legs), and a burning sensation (e.g. in the feet and/or hands).

In one embodiment, the pain treated by the methods of this application is neuropathy induced by chemotherapy.

In one embodiment, the pain prevented by the methods of this application is neuropathy induced by chemotherapy.

In one embodiment, the pain treated and/or prevented by the methods of this application is neuropathy induced by chemotherapy with a taxane. For example, paclitaxel, docetaxel, abraxane, or taxotere.

In one embodiment, the pain treated and/or prevented by the methods of this application is neuropathy induced by chemotherapy with an alkylating agent. For example, cyclophosphamide, mechlorethamine, chlorambucil, melphalan, decarbazine, nitrosoureas, or temozolomide.

In one embodiment, the pain treated and/or prevented by the methods of this application is neuropathy induced by chemotherapy with an anthracycline. For example, daunorubicin, doxorubicin, epirubicin, idarubicin, mitoxantrone, or valrubicin.

In one embodiment, the pain treated and/or prevented by the methods of this application is neuropathy induced by chemotherapy with an anti-metabolite or nucleoside analog. For example, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

In one embodiment, the pain treated and/or prevented by the methods of this application is neuropathy induced by chemotherapy with a CDK inhibitor. For example, palbociclib, dinaciclib, P276-00, roniciclib, ribociclib, P1446A-05, AT7519M, SNS-032, SCH 727965, AG-024322, hygrolidin, fascaplysin, abemaciclib, arcyriaflavin A, CINK4, AM-5992, CDK4 Inhibitor (CAS #546102-60-7), CDK4 Inhibitor III (CAS #265312-55-8), Cdk4/6 Inhibitor IV (CAS #359886-84-3), MM-D37K, NSC 625987, or ON-123300. (See Law, M. E. et al. "Cyclin-Dependent Kinase Inhibitors as Anticancer Therapeutics" Mol. Pharmacol. 88:846-852 (2015), which is incorporated by reference herein in its entirety.)

In one embodiment, the pain treated and/or prevented by the methods of this application is neuropathy induced by chemotherapy with a vinca alkaloid or derivative thereof. For example, vinblastine, vincristine, vindesine, or vinorelbine.

In one embodiment, the pain treated and/or prevented by the methods of this application is neuropathy induced by chemotherapy with a platinum-based agent. For example, cisplatin, carboplatin, or oxaliplatin.

In one embodiment, the pain treated and/or prevented by the methods of this application is neuropathy induced by chemotherapy with a nucleotide analog or nucleotide precursor analog. For example, azacitidine, azathioprine, capecitabine, cytarabine, doxifluridine, fluorouracil, gemcitabine, hydroxyurea, mercaptopurine, methotrexate, or tioguanine.

In one embodiment, the pain treated and/or prevented by the methods of this application is neuropathy induced by chemotherapy with a topoisomerase inhibitor, e.g. an inhibitor or topoisomerase I or an inhibitor of topoisomerase II. For example, irinotecan, topotecan, etoposide, teniposide, or tafluposide.

In one embodiment, the pain treated and/or prevented by the methods of this application is neuropathy induced by chemotherapy with dactinomycin, bleomycin, sorafenib, lenvatinib, regorafenib, sunitinib, palbociclib, afatinib, alectinib, axitinib, bortezomib, bosutinib, cabozantinib, carfilzomib, ceritinib, cobimetinib, crizotinib, dabrafenib, erlotinib, gefitinib, ibrutinib, idelalisib, imatinib, ixazomib, lapatinib, nilotinib, nintedanib, niraparib, osimertinib, pazopanib, pegaptanib, ponatinib, rucaparib, ruxolitinib, sonidegib, tofacitinib, trametinib, vandetanib, vemurafenib, vismodegibor, necitumumab, cetuximab, neratinib, panitumumab, or dacomitinib.

In one embodiment, the pain treated and/or prevented by the methods of this application is toxic pain.

Toxic pain includes, but is not limited to, pain associated with contact with toxins, poisons, and chemicals. In one embodiment, this can happen through drug or chemical abuse or through exposure to industrial chemicals in the workplace or in the environment (after either limited or long-term exposure). For example, the toxin, poison, and/or chemical may be found in an insecticide, solvent, glue, or herbal medicines.

In one embodiment, the toxic pain arises from contact with one or more of the following: acrylamide, alcohol, arsenic, brevetoxin (via shellfish), buckthorn berry toxin, agent orange, carbon disulfide, ciguatera toxin (via shellfish), dioxin, ethanol, ethylene glycol (antifreeze), hexacarbons, tetrodotoxin (via puffer fish), lead, mercury, nitrous oxide, organophosphates, saxitoxin (via shellfish), thallium, or zinc.

In one aspect, this application pertains to a method of treating pain comprising administering to a subject in need of treatment a therapeutically effective amount of Compound I, or a pharmaceutically acceptable salt, solvate, or prodrug thereof, wherein the pain is treated, ameliorated, or eliminated in the subject, or the symptoms of the pain are lessened in the subject, in less than 8 hours after administration. For example, in less than 7 hours, 6 hours, 5 hours, 4 hours, 3 hours, 2 hours, 1 hour, 45 minutes, 30 minutes, 20 minutes, 15 minutes, 10 minutes, or 5 minutes after administration of the therapeutically effective amount of Compound I, or a pharmaceutically acceptable salt, solvate, or prodrug thereof.

In one aspect, the pain to be treated may be any type of pain disclosed herein, including, for example, acute pain, chronic pain, toxic pain, neuropathic pain, nociceptive pain, inflammatory pain, post-operative pain, visceral pain, chemotherapy-induced pain, or a combination thereof.

In one aspect, this application pertains to a method of preventing pain, i.e., prophylactically treating pain. For example, a subject about to undergo chemotherapy may be administered Compound I or a pharmaceutically acceptable salt, solvate, or prodrug thereof, in order to prevent the occurrence of neuropathy induced by chemotherapy before the pain ever starts.

In one embodiment, for any of the methods of preventing pain disclosed herein, the method comprises administering to a subject in need of treatment a therapeutically effective amount of Compound I, or a pharmaceutically acceptable salt, solvate, or prodrug thereof, wherein Compound I is administered to the subject before commencement of chemotherapy. For example 8 hours before administration of the chemotherapy, 7 hours before administration of the chemotherapy, 6 hours before administration of the chemotherapy, 5 hours before administration of the chemotherapy, 4 hours before administration of the chemotherapy, 3 hours before administration of the chemotherapy, 2 hours before administration of the chemotherapy, 1 hour before administration of the chemotherapy, 45 minutes before administration of the chemotherapy, 30 minutes before administration of the chemotherapy, 20 minutes before administration of the chemotherapy, 15 minutes before administration of the chemotherapy, 10 minutes before administration of the chemotherapy, or 5 minutes before administration of the chemotherapy.

In one aspect, the pain to be prevented may be any type of pain disclosed herein, including, for example, acute pain, chronic pain, toxic pain, neuropathic pain, nociceptive pain, inflammatory pain, post-operative pain, visceral pain, chemotherapy-induced pain, or a combination thereof.

In one aspect, the application pertains to simultaneously treating current pain suffered by the subject and preventing the occurrence of future pain in the subject.

For example, a subject undergoing chemotherapy may be administered a therapeutically effective amount of Compound I in order to treat neuropathy induced by chemotherapy. The same subject may be administered Compound I in order prevent future neuropathy induced by chemotherapy or any other type pain disclosed herein, e.g., acute pain, chronic pain, toxic pain, nociceptive pain, inflammatory pain, post-operative pain, visceral pain, and chemotherapy-induced pain.

Nociceptors can become hyperexcitable (sensitized) by various mechanisms in the presence of peripheral tissue injury. Individual nociceptors that have been sensitized can be activated by stimuli that previously would not have been intense enough to cause activation (allodynia), as well as by previously noxious stimuli that now produce an even greater sensation of pain (hyperalgesia). The electrophysiological correlates of this altered evoked pain response include a lowered threshold for nociceptor activation and increased frequency of firing in response to a suprathreshold stimulus, respectively. Furthermore, clinical symptoms of spontaneous pain can be directly correlated to the spontaneous spike firing in nociceptors. Peripheral sensitization often leads to central sensitization, or increased synaptic efficacy and spontaneous activity of dorsal horn neurons in the spinal cord.

The term "hyperalgesia", as used herein, refers to an extreme or increased sensitivity to pain in a subject.

The term "antihyperalgesic effect", as used herein, refers to a reduction in a subject's sensitivity to pain.

In one aspect, the therapeutically effective amount of Compound I, or a pharmaceutically acceptable salt, solvate, or prodrug thereof, induces or promotes an antihyperalgesic effect, i.e., it reduces a subject's sensitivity to pain. Thus, in another aspect, this application pertains to a method of reducing a subject's sensitivity to pain comprising administering to a subject in need thereof a therapeutically effective amount of Compound I, or a pharmaceutically acceptable salt, solvate, or prodrug thereof.

In one aspect, the therapeutically effective amount of Compound I, or a pharmaceutically acceptable salt, solvate, or prodrug thereof, induces or promotes an antihyperalgesic effect in the subject in less than 8 hours after administration. For example, in less than 7 hours, 6 hours, 5 hours, 4 hours, 3 hours, 2 hours, 1 hour, 45 minutes, 30 minutes, 20 minutes, 15 minutes, 10 minutes, or 5 minutes after administration of the therapeutically effective amount of Compound I, or a pharmaceutically acceptable salt, solvate, or prodrug thereof.

In one embodiment, the therapeutically effective amount of Compound I, or a pharmaceutically acceptable salt, solvate, or prodrug thereof, induces or promotes an antihyperalgesic effect, i.e., it reduces a subject's sensitivity to pain brought on by opioid use by the subject for the treatment of pain.

In one embodiment, the antihyperalgesic effect of the therapeutically effective amount of Compound I, or a pharmaceutically acceptable salt, solvate, or prodrug thereof, reduces or promotes a subject's sensitivity to pain by about 10%, by about 20%, by about 30%, by about 40%, by about 50%, by about 60%, by about 70%, by about 80%, by about 90%, or by about 100%.

In any of the methods disclosed herein, the treatment or amelioration of pain, fibromyalgia, neuropathy, or chemotherapy-induced pain in a subject, the promotion of an antihyperalgesic effect in a subject, or the reduction in a subject's sensitivity to pain can be determined by before and after assessments of the subject made by a medical practitioner using any one of the many methods know in the art. (Haefeli, M. "Pain Assessment" Eur. Spine J. 2006 January; 15(Suppl 1): S17-S24; Stewart, J. "The Challenges of Cancer Pain Assessment" Ulster Med. J. 2014 January; 83(1): 44-46.)

In the examples disclosed herein, nociceptive threshold testing deliberately applies a noxious stimulus to a subject in order to study pain, the efficacy of analgesic drugs, and to establish dosing levels and period of effect. After a baseline level is established the test drug is administered and the elevation in threshold recorded at specified time points. The threshold should return to the baseline (pre-treatment) value once the test drug or drugs wear off.

For instance, intraplantar injection of a carrageenan solution into an animal's (e.g., a rat's) hindpaw induces a mechanical hyperalgesia as evidenced by the marked and significant decrease in the nociceptive threshold. Morphine, used as positive control, fully reverses mechanical hyperalgesia with a maximum effect reached 30 min. after dosing.

In other examples, sciatic nerve ligation induces mechanical hyperalgesia as evidenced by a marked and significant decrease in the nociceptive threshold, significantly reduced by morphine, which may be used as a positive control.

In other examples, the efficacy of chronic administration of Compound I on paclitaxel-induced neuropathic pain to either reverse paclitaxel-induced pain response or prevent it was assessed. In one embodiment, Compound I, at 1, 3 and 10 mg/kg, showed significant increases in pain with threshold, thereby suggesting that Compound I is efficacious in the treatment and prevention of chemotherapy-induced peripheral neuropathic pain.

According to the methods of treatment and/or prevention of the present application, pain is treated, ameliorated, cured, or prevented in a subject by administering to the subject a therapeutically effective amount of Compound I, or a pharmaceutically acceptable salt, solvate, or prodrug thereof, in such amounts and for such time as is necessary to achieve the desired result.

According to the methods of treatment of the present application, pain is treated in a subject by administering to the subject a therapeutically effective amount of Compound I, or a pharmaceutically acceptable salt, solvate, or prodrug thereof, in such amounts and for such time as is necessary to achieve the desired result.

According to the methods of treatment of the present application, one or more symptoms of pain is lessened in a subject by administering to the subject a therapeutically effective amount of Compound I, or a pharmaceutically acceptable salt, solvate, or prodrug thereof, in such amounts and for such time as is necessary to achieve the desired result.

According to the methods of treatment of the present application, pain is ameliorated in a subject by administering to the subject a therapeutically effective amount of Compound I, or a pharmaceutically acceptable salt, solvate, or prodrug thereof, in such amounts and for such time as is necessary to achieve the desired result.

According to the methods of treatment of the present application, pain is cured in a subject by administering to the subject a therapeutically effective amount of Compound I, or a pharmaceutically acceptable salt, solvate, or prodrug thereof, in such amounts and for such time as is necessary to achieve the desired result.

According to the methods of treatment of the present application, pain is prevented in a subject by administering to the subject a therapeutically effective amount of Compound I, or a pharmaceutically acceptable salt, solvate, or prodrug thereof, in such amounts and for such time as is necessary to achieve the desired result.

As is well understood in the medical arts, a therapeutically effective amount of Compound I, or a pharmaceutically acceptable salt, solvate, or prodrug thereof, will be at a reasonable benefit/risk ratio applicable to any medical treatment.

In one aspect, this application pertains to the efficacy of Compound I, or a pharmaceutically acceptable salt, solvate, or prodrug thereof, in various pain areas, including, but not limited to, acute and toxic pain; neuropathic pain; inflammatory pain; post-operative pain; visceral pain; and behavior and acute toxicity, may be assessed using high throughput screening in rats (i.e., ALGOGram™) and comparing the data for various doses of Compound I, or a pharmaceutically acceptable salt, solvate, or prodrug thereof, with known controls. For instance, morphine (for acute pain, toxic pain, neuropathic pain, and post-operative pain); gabapentin (for neuropathic pain); indomethacin (for inflammatory pain), and U-50488 (for acute pain, toxic pain, and visceral pain).

In one aspect, this application pertains to the antihyperanalgesic effect of Compound I, or a pharmaceutically acceptable salt, solvate, or prodrug thereof, in a model of carrageenan-induced mechanical hyperalgesia in rats. In this model, inflammation is induced by intraplantar injection of carrageenan into the paw of a rat. Carrageenan is a polysaccharide obtained from various seaweeds. When injected into the plantar paw or the knee joint, carrageenan results in a localized inflammation, therefore decreases weight bearing, modifies guarding of the treated limb and induced thermal and mechanical hyperalgesia/allodynia. This type of model is widely and reliably used for revealing the efficacy of new analgesics. In one embodiment, intraperitoneal administration of various doses of Compound I, or a pharmaceutically acceptable salt, solvate, or prodrug thereof, induces an increase in the nociceptive threshold compared to a control group.

In one aspect, this application pertains to the antihyperalgesic effect of Compound I, or a pharmaceutically acceptable salt, solvate, or prodrug thereof, in a model of peripheral mononeuropathy in rats. In this model, unilateral peripheral mononeuropathy was induced by surgical loose ligation of the rat the sciatic nerve of the right hindpaw in anaesthetized rats. In one embodiment, intraperitoneally administration of various doses of Compound I, or a pharmaceutically acceptable salt, solvate, or prodrug thereof, induces an increase in the nociceptive threshold compared to a control group.

In one aspect, this application pertains to the analgesic efficacy of Compound I, or a pharmaceutically acceptable salt, solvate, or prodrug thereof, in a model of chemotherapy induced peripheral neuropathic pain in rats. In one embodiment, treatment with Compound I, or a pharmaceutically acceptable salt, solvate, or prodrug thereof, significantly reduced neuropathic pain in rats compared to a control group.

In general, Compound I, or a pharmaceutically acceptable salt, solvate, or prodrug thereof, will be administered in therapeutically effective amounts via any of the usual and acceptable modes known in the art, either singly or in combination with one or more therapeutic agents. A therapeutically effective amount may vary widely depending on the severity of the pain, the age and relative health of the subject, the clinical condition of the recipient subject, and the experience and judgment of the clinician or practitioner administering the therapy, among other factors affecting the selected dosage.

In one embodiment, the therapeutically effective amount of Compound I can be administered to the subject on a daily (e.g., 1, 2, or 3 times daily), weekly (e.g., 1, 2, 3, 4, or 5 times weekly), or monthly basis (e.g., 1, 2, 3, 4, 5, 6, 7, 8, 9, or 10 times monthly). Determination of the appropriate dosing schedule is within the routine level of skill in the art.

The therapeutically effective amount of Compound I may be administered one or more times over a day for up to 30 or more days, followed by 1 or more days of non-administration of Compound I. This type of treatment schedule, i.e., administration of Compound I on consecutive days followed by non-administration of Compound I on consecutive days may be referred to as a treatment cycle. A treatment cycle may be repeated as many times as necessary to achieve the intended affect.

In one embodiment, the therapeutically effective amount of Compound I is 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, 1200, 1225, 1250, 1275, 1300, 1325, 1350, 1375, 1400, 1425, 1450, 1475, 1500, 1525, 1550, 1575, 1600, 1625, 1650, 1675, 1700, 1725, 1750, 1775, 1800, 1825, 1850, 1875, 1900, 1925, 1950, 1975, or 2000 mg administered once, twice, three time, four times, or more daily for one, two, three, four, five, six, seven, eight, nine, ten, eleven, twelve, thirteen, fourteen, fifteen, thirty consecutive days, or, once, twice, three time, four times, or more daily for 2 months, 3 months, 4 months, 5 months, 6 months, or longer.

In one embodiment, the therapeutically effective amount of Compound I is about 10 to about 40 mg, about 20 to about 50 mg, about 30 to about 60 mg, about 40 to about 70 mg, about 50 to about 80 mg, about 60 to about 90 mg, about 70 to about 100 mg, about 80 to about 110 mg, about 90 to about 120 mg, about 100 to about 130 mg, about 110 to about 140 mg, about 120 to about 150 mg, about 130 to about 160 mg, about 140 to about 170 mg, about 150 to about 180 mg, about 160 to about 190 mg, about 170 to about 200 mg, about 180 to about 210 mg, about 190 to about 220 mg, about 200 to about 230 mg, about 210 to about 240 mg, about 220 to about 250 mg, about 230 to about 260 mg, about 240 to about 270 mg, about 250 to about 280 mg, about 260 to about 290 mg, about 270 to about 300 mg, about 280 to about 310 mg, about 290 to about 320 mg, about 300 to about 330 mg, about 310 to about 340 mg, about 320 to about 350 mg, about 330 to about 360 mg, about 340 to about 370 mg, about 350 to about 380 mg, about 360 to about 390 mg, or about 370 to about 400 mg administered once, twice, three time, four times, or more daily in single or divided doses (which dose may be adjusted for the patient's weight in kg, body surface area in m², and age in years).

The therapeutically effective amount of Compound I can also range from about 0.001 mg/kg per day to about 1,000 mg/kg per day. In an aspect, therapeutically effective amount of Compound I can range from about 0.01 mg/kg per day to about 100 mg/kg per day. In an aspect, therapeutically effective amount of Compound I can range from about 0.05 mg/kg per day to about 50 mg/kg per day. In an aspect, therapeutically effective amount of Compound I can range from about 0.1 mg/kg per day to about 25 mg/kg per day. In an aspect, therapeutically effective amount of Compound I can range from about 0.25 mg/kg per day to about 20 mg/kg per day. In an aspect, therapeutically effective amount of Compound I can range from about 0.5 mg/kg per day to about 10 mg/kg per day. In an aspect, therapeutically effective amount of Compound I can range from about 0.75 mg/kg per day to about 5 mg/kg per day. In an aspect, therapeutically effective amount of Compound I can range from about 0.10 mg/kg per day to about 1 mg/kg per day. The therapeutically effective amount of Compound I may be conveniently administered, e.g., divided into smaller doses and administered two times, three times, or four times a day in a controlled-release or a sustained-release form.

In one embodiment, the therapeutically effective amount of Compound I is about 0.05 mg/kg per day, about 0.10 mg/kg per day, about 0.15 mg/kg per day, about 0.20 mg/kg per day, about 0.25 mg/kg per day, about 0.30 mg/kg per day, about 0.35 mg/kg per day, about 0.40 mg/kg per day, about 0.45 mg/kg per day, about 0.50 mg/kg per day, about 0.55 mg/kg per day, about 0.60 mg/kg per day, about 0.65 mg/kg per day, about 0.70 mg/kg per day, about 0.75 mg/kg per day, about 0.80 mg/kg per day, about 0.85 mg/kg per day, about 0.90 mg/kg per day, about 0.95 mg/kg per day, or about 1.00 mg/kg per day. The therapeutically effective amount of Compound I may be conveniently administered, e.g., divided into smaller doses and administered two times, three times, or four times a day in a controlled-release or a sustained-release form.

In one embodiment, the therapeutically effective amount of Compound I is about 1.05 mg/kg per day, about 1.10 mg/kg per day, about 1.15 mg/kg per day, about 1.20 mg/kg per day, about 1.25 mg/kg per day, about 1.30 mg/kg per day, about 1.35 mg/kg per day, about 1.40 mg/kg per day, about 1.45 mg/kg per day, about 1.50 mg/kg per day, about 1.55 mg/kg per day, about 1.60 mg/kg per day, about 1.65 mg/kg per day, about 1.70 mg/kg per day, about 1.75 mg/kg per day, about 1.80 mg/kg per day, about 1.85 mg/kg per day, about 1.90 mg/kg per day, about 1.95 mg/kg per day, or about 2.00 mg/kg per day. The therapeutically effective amount of Compound I may be conveniently administered, e.g., divided into smaller doses and administered two times, three times, or four times a day in a controlled-release or a sustained-release form.

In one embodiment, the therapeutically effective amount of Compound I is about 2.05 mg/kg per day, about 2.10 mg/kg per day, about 2.15 mg/kg per day, about 2.20 mg/kg per day, about 2.25 mg/kg per day, about 2.30 mg/kg per day, about 2.35 mg/kg per day, about 2.40 mg/kg per day, about 2.45 mg/kg per day, about 2.50 mg/kg per day, about 2.55 mg/kg per day, about 2.60 mg/kg per day, about 2.65 mg/kg per day, about 2.70 mg/kg per day, about 2.75 mg/kg per day, about 2.80 mg/kg per day, about 2.85 mg/kg per day, about 2.90 mg/kg per day, about 2.95 mg/kg per day, or about 3.00 mg/kg per day. The therapeutically effective amount of Compound I may be conveniently administered, e.g., divided into smaller doses and administered two times, three times, or four times a day in a controlled-release or a sustained-release form.

In one embodiment, the therapeutically effective amount of Compound I is about 3.05 mg/kg per day, about 3.10 mg/kg per day, about 3.15 mg/kg per day, about 3.20 mg/kg per day, about 3.25 mg/kg per day, about 3.30 mg/kg per day, about 3.35 mg/kg per day, about 3.40 mg/kg per day, about 3.45 mg/kg per day, about 3.50 mg/kg per day, about 3.55 mg/kg per day, about 3.60 mg/kg per day, about 3.65 mg/kg per day, about 3.70 mg/kg per day, about 3.75 mg/kg per day, about 3.80 mg/kg per day, about 3.85 mg/kg per day, about 3.90 mg/kg per day, about 3.95 mg/kg per day, or about 4.00 mg/kg per day. The therapeutically effective amount of Compound I may be conveniently administered, e.g., divided into smaller doses and administered two times, three times, or four times a day in a controlled-release or a sustained-release form.

In one embodiment, the therapeutically effective amount of Compound I is about 4.05 mg/kg per day, about 4.10 mg/kg per day, about 4.15 mg/kg per day, about 4.20 mg/kg per day, about 4.25 mg/kg per day, about 4.30 mg/kg per day, about 4.35 mg/kg per day, about 4.40 mg/kg per day, about 4.45 mg/kg per day, about 4.50 mg/kg per day, about 4.55 mg/kg per day, about 4.60 mg/kg per day, about 4.65 mg/kg per day, about 4.70 mg/kg per day, about 4.75 mg/kg per day, about 4.80 mg/kg per day, about 4.85 mg/kg per day, about 4.90 mg/kg per day, about 4.95 mg/kg per day, or about 5.00 mg/kg per day. The therapeutically effective amount of Compound I may be conveniently administered, e.g., divided into smaller doses and administered two times, three times, or four times a day in a controlled-release or a sustained-release form.

In one embodiment, the therapeutically effective amount of Compound I is about 5.05 mg/kg per day, about 5.10 mg/kg per day, about 5.15 mg/kg per day, about 5.20 mg/kg per day, about 5.25 mg/kg per day, about 5.30 mg/kg per day, about 5.35 mg/kg per day, about 5.40 mg/kg per day, about 5.45 mg/kg per day, about 5.50 mg/kg per day, about 5.55 mg/kg per day, about 5.60 mg/kg per day, about 5.65 mg/kg per day, about 5.70 mg/kg per day, about 5.75 mg/kg per day, about 5.80 mg/kg per day, about 5.85 mg/kg per day, about 5.90 mg/kg per day, about 5.95 mg/kg per day, or about 6.00 mg/kg per day. The therapeutically effective amount of Compound I may be conveniently administered, e.g., divided into smaller doses and administered two times, three times, or four times a day in a controlled-release or a sustained-release form.

In one embodiment, the therapeutically effective amount of Compound I is about 6.05 mg/kg per day, about 6.10 mg/kg per day, about 6.15 mg/kg per day, about 6.20 mg/kg per day, about 6.25 mg/kg per day, about 6.30 mg/kg per day, about 6.35 mg/kg per day, about 6.40 mg/kg per day, about 6.45 mg/kg per day, about 6.50 mg/kg per day, about 6.55 mg/kg per day, about 6.60 mg/kg per day, about 6.65 mg/kg per day, about 6.70 mg/kg per day, about 6.75 mg/kg per day, about 6.80 mg/kg per day, about 6.85 mg/kg per day, about 6.90 mg/kg per day, about 6.95 mg/kg per day, or about 7.00 mg/kg per day. The therapeutically effective amount of Compound I may be conveniently administered, e.g., divided into smaller doses and administered two times, three times, or four times a day in a controlled-release or a sustained-release form.

In one embodiment, the therapeutically effective amount of Compound I is about 7.05 mg/kg per day, about 7.10 mg/kg per day, about 7.15 mg/kg per day, about 7.20 mg/kg per day, about 7.25 mg/kg per day, about 7.30 mg/kg per day, about 7.35 mg/kg per day, about 7.40 mg/kg per day, about 7.45 mg/kg per day, about 7.50 mg/kg per day, about 7.55 mg/kg per day, about 7.60 mg/kg per day, about 7.65 mg/kg per day, about 7.70 mg/kg per day, about 7.75 mg/kg per day, about 7.80 mg/kg per day, about 7.85 mg/kg per day, about 7.90 mg/kg per day, about 7.95 mg/kg per day, or about 8.00 mg/kg per day. The therapeutically effective amount of Compound I may be conveniently administered, e.g., divided into smaller doses and administered two times, three times, or four times a day in a controlled-release or a sustained-release form.

In one embodiment, the therapeutically effective amount of Compound I is about 8.05 mg/kg per day, about 8.10 mg/kg per day, about 8.15 mg/kg per day, about 8.20 mg/kg per day, about 8.25 mg/kg per day, about 8.30 mg/kg per day, about 8.35 mg/kg per day, about 8.40 mg/kg per day, about 8.45 mg/kg per day, about 8.50 mg/kg per day, about 8.55 mg/kg per day, about 8.60 mg/kg per day, about 8.65 mg/kg per day, about 8.70 mg/kg per day, about 8.75 mg/kg per day, about 8.80 mg/kg per day, about 8.85 mg/kg per day, about 8.90 mg/kg per day, about 8.95 mg/kg per day, or about 9.00 mg/kg per day. The therapeutically effective amount of Compound I may be conveniently administered, e.g., divided into smaller doses and administered two times, three times, or four times a day in a controlled-release or a sustained-release form.

In one embodiment, the therapeutically effective amount of Compound I is about 9.05 mg/kg per day, about 9.10 mg/kg per day, about 9.15 mg/kg per day, about 9.20 mg/kg per day, about 9.25 mg/kg per day, about 9.30 mg/kg per day, about 9.35 mg/kg per day, about 9.40 mg/kg per day, about 9.45 mg/kg per day, about 9.50 mg/kg per day, about 9.55 mg/kg per day, about 9.60 mg/kg per day, about 9.65 mg/kg per day, about 9.70 mg/kg per day, about 9.75 mg/kg per day, about 9.80 mg/kg per day, about 9.85 mg/kg per day, about 9.90 mg/kg per day, about 9.95 mg/kg per day, or about 10.00 mg/kg per day. The therapeutically effective amount of Compound I may be conveniently administered, e.g., divided into smaller doses and administered two times, three times, or four times a day in a controlled-release or a sustained-release form.

The therapeutically effective amount of Compound I can be estimated initially either in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in experimental animals. The dosage may vary within this range depending upon the dosage form employed, sensitivity of the patient, and the route of administration.

Upon improvement of a subject's pain after initial treatment with an induction dose of Compound I, or a pharmaceutically acceptably salt, solvate, or prodrug thereof, a maintenance dose of Compound I, or a pharmaceutically acceptable salt, solvate, or prodrug thereof, may be administered, if necessary. Subsequently, the dosage or frequency of administration of Compound I, or a pharmaceutically acceptably salt, solvate, or prodrug thereof, or both, may be reduced, as a function of the symptoms, to a level at which the improved condition is retained, i.e., a maintenance dose. Further, if and when the symptoms have been alleviated to the desired level, treatment with Compound I, or a pharmaceutically acceptably salt, solvate, or prodrug thereof, should cease. The subject may, however, require intermittent treatment with Compound I, or a pharmaceutically acceptably salt, solvate, or prodrug thereof, on a long-term basis upon any recurrence of disease symptoms or to prevent recurrence of the same.

Upon improvement of a subject's pain, fibromyalgia, neuropathy, or chemotherapy-induced pain, upon promotion of an antihyperalgesic effect in the subject, or upon a reduction in the subject's sensitivity to pain after initial treatment with an induction dose of Compound I, or a pharmaceutically acceptably salt, solvate, or prodrug thereof, a maintenance dose of Compound I, or a pharmaceutically acceptable salt, solvate, or prodrug thereof, may be administered, if necessary. Subsequently, the maintenance dose of Compound I, or a pharmaceutically acceptably salt, solvate, or prodrug thereof, may be reduced, as a function of the symptoms, to a level at which the improved condition is retained. Further, if and when the symptoms have been alleviated to the desired level, treatment with Compound I, or a pharmaceutically acceptably salt, solvate, or prodrug thereof, should cease. The subject may, however, require intermittent treatment with Compound I, or a pharmaceutically acceptably salt, solvate, or prodrug thereof, on a long-term basis upon any recurrence of disease symptoms or to prevent recurrence of the same.

Upon improvement of a subject's pain, fibromyalgia, neuropathy, or chemotherapy-induced pain, upon promotion of an antihyperalgesic effect in the subject, or upon a reduction in the subject's sensitivity to pain after initial treatment with an induction dose of Compound I, or a pharmaceutically acceptably salt, solvate, or prodrug thereof, a maintenance dose with Compound I, an additional therapeutic agent for the treatment of pain, or combinations thereof, may be administered, if necessary. The maintenance dose of Compound I and/or the additional therapeutic agent may be lower than the induction dose, may be administered less frequently than the induction dose, or may be both lower than and administered less frequently than the induction dose.

Subsequently, the maintenance dose of Compound I, or a pharmaceutically acceptably salt, solvate, or prodrug thereof, the additional therapeutic agent, or combinations thereof, may be reduced, as a function of the subject's symptoms, to a level at which the improved condition is retained. Further, if and when the symptoms have been alleviated to the desired level, treatment with Compound I, or a pharmaceutically acceptably salt, solvate, or prodrug thereof, the additional therapeutic agent, or combinations thereof, should cease. The subject may, however, require intermittent treatment of Compound I, or a pharmaceutically acceptably salt, solvate, or prodrug thereof, the additional therapeutic agent, or combinations thereof, on a long-term basis to prevent recurrence of disease symptoms or to treat disease symptoms upon their recurrence.

It will be understood, however, that the total daily usage of the compounds and compositions of the present application will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The methods of this application for treating pain may further comprise the administration of one or more additional therapeutic agents which may include, but are limited to, anticonvulsants, antidepressants, nonsteroidal anti-inflammatory drugs, glucocorticoids, gabapentin, pregabalin, cannabinoids, botulinum toxin, dietary supplements (e.g., alpha lipoic acid, benfotiamine), neuromodulators, and topical agents (e.g., lidocaine).

The methods of this application for treating pain may further comprise additional therapies including, but not limited to, acupuncture, electric nerve stimulation, minimally invasive spinal procedures, and psychologic treatment.

The application also provides for pharmaceutical combinations, e.g., a kit, comprising: (a) a first agent which is Compound I of the application as disclosed herein, in free form or in pharmaceutically acceptable salt form, and, optionally, (b) at least one co-agent. The kit can comprise instructions for its administration.

Pharmaceutical Compositions

Any of the compositions or pharmaceutical compositions described herein may be formulated with pharmaceutically acceptable carriers or diluents as well as any other known adjuvants and excipients in accordance with conventional techniques such as those disclosed in Remington: The Science and Practice of Pharmacy, 21$^{st}$ Edition, 2000, Lippincott Williams & Wilkins, which is incorporated herein in its entirety. In one aspect, the disclosure relates to a pharmaceutical composition comprising Compound I that is in the form of tablets, capsules, oral preparations, powders, granules, pills, injectable or infusible liquid, solutions, suspensions, emulsions, suppositories, ointments, creams, lotions, lozenges, chews, gels, pastes, multi- and nano-particulates, gels, solid solutions, liposomes, nanoparticles, films, ovules, sprays, injectables, and liquid formulations or transdermal delivery devices.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this application with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this application include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this application.

The ointments, pastes, creams and gels may contain, in addition to an active compound of this application, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this application, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As is common practice, the compositions are normally accompanied by written or printed instructions for use in the treatment in question.

The compositions of the application may further include one or more therapeutic agents. In one embodiment, the therapeutic agent may also be used for the treatment of pain in the subject. The therapeutic agent includes, but is not limited to, anticonvulsants, antidepressants, nonsteroidal anti-inflammatory drugs, glucocorticoids, gabapentin, pregabalin, cannabinoids, botulinum toxin, dietary supplements (e.g., alpha lipoic acid, benfotiamine), neuromodulators, and topical agents (e.g., lidocaine)

SUMMARY OF THE EXAMPLES

The effect of a single administration of 0.1 mg/kg MIN-117 and 1.0 mg/kg MIN-117 was assessed in various pain areas in ALGOGram™, including acute and toxic pain; neuropathic pain; inflammatory pain; post-operative pain; visceral pain; and behavior and acute toxicity were assessed using model test at 0.1 mg/kg MIN-117 and 1.0 mg/kg MIN-117 (i.p.). For each test, an internal reference (e.g., morphine) was used as a control for comparison. Testing was done 2 hours after treatment.

The antihyperalgesic effect of a single intraperitoneal administration of MIN-117 in a model of carrageenan-induced mechanical hyperalgesia in rats was assessed. Carrageenan is a polysaccharide obtained from various seaweeds. When injected into the plantar paw or the knee joint, carrageenan results in a localized inflammation, therefore decreases weight bearing, modifies guarding of the treated limb and induced thermal and mechanical hyperalgesia/allodynia.

In this model, inflammation is induced by intraplantar injection of carrageenan (2%) into the right hindpaw of the rat. Three hours later, reaction thresholds are measured using the paw pressure test. Pressure is gradually applied to both hind paws (inflamed and control) of the rat, and reaction thresholds are determined as the pressure (g) required to elicit paw withdrawal or vocalization. Morphine (3 mg/kg, s.c.) was used as a positive control.

This assay is widely and reliably used for revealing the efficacy of new analgesics in a model of inflammatory pain in conscious rats.

Static mechanical hyperalgesia was assessed using the Paw Pressure test or Randall & Selitto test. This test requires the application of an increasing pressure on the hind paws between a flat surface and a blunt pointer. This test is usually used with animals with one hind paw inflamed by an injection or injured by ligation, and one normal hind paw, to evaluate drugs for analgesic action. The apparatus exerts a steadily increasing force and reaction threshold is determined as the pressure (g) required to elicit paw withdrawal and/or vocalization. In one experiment, static mechanical hyperalgesia was assessed. Each reaction threshold measurement was done for both hind paws.

Five experimental groups of 10 rats each were used. Each group was first injected with of 100 µL of a 2% carrageenan suspension in the plantar aspect of the right hindpaw. Three hours after carrageenan injection, paw withdrawal threshold was measured using the paw pressure test (Baseline). The 5 groups were then administered the following: vehicle (0.5% HPMC, i.p.); MIN-117 (0.01 mg/kg, i.p.); MIN-117 (0.1 mg/kg, i.p.); MIN-117 (1 mg/kg, i.p.); and morphine (3 mg/kg, s.c.).

After administering vehicle, MIN-117, or morphine, the antihyperalgesic effect of the compounds was evaluated using the paw pressure test at 0 min. ($T_0$), 30 min., 60 min., 120 min., and 240 min.

Vehicle and MIN-117 were administered intraperitoneally at 10 mL/kg. Morphine was subcutaneously administered at 5 mL/kg. Dosing and testing were performed in a random order by a blinded experimenter except for the morphine-treated group. Doses were expressed in terms of free active substance. Rats were sacrificed at the end of the experiment by $CO_2$ inhalation pending subsequent removal by a certified company.

All the treatment groups exhibited a significantly reduced nociceptive threshold of the injured paw as compared to the control paw. Rats from the vehicle-treated group exhibited, for the injured paw, reduced and stable nociceptive thresholds as compared to the control paw throughout the observation period of the study. Morphine, subcutaneously administered at 3 mg/kg, induced a marked and significant increase in the injured paw withdrawal threshold from 30 min. to 120 min. after administration with a maximum effect reached 30 min. after treatment as compared to the vehicle-treated group. MIN-117 intraperitoneally administered at 0.01 or 0.1 mg/kg did not induce any significant increase in the paw withdrawal threshold throughout the time course study. However, MIN-117 intraperitoneally administered at 1 mg/kg induced a slight increase in the nociceptive threshold becoming significant 120 min. after injection as compared to the vehicle-treated group.

The antihyperalgesic effect of a single intraperitoneal administration of MIN-117 in a model of peripheral mononeuropathy (Bennett model) in rats was assessed.

The model of Chronic Constriction Injury (CCI) is based on a discrete peripheral nerve injury and can be related to post-traumatic/postsurgical neuropathic pain experienced by patients. Unilateral peripheral mononeuropathy was induced by loose ligation of the rat the sciatic nerve of the right hindpaw in anaesthetized rats (xylazine 10 mg/kg i.p., ketamine 60 mg/kg i.p.). The common sciatic nerve was exposed at the level of the middle of the thigh by blunt dissection through the biceps femoris. Proximal to the sciatic trifurcation, four ligatures were tied loosely around it with about 1 mm spacing. Great care was taken to tie the ligatures, such that the diameter of the nerve was seen to be just barely constricted.

Fourteen days later, static mechanical hyperalgesia is assessed using the Paw pressure test. This test requires the application of an increasing pressure on the hind paws between a flat surface and a blunt pointer. This test is usually used with animals with one hindpaw inflamed by an injection or injured by ligation, and one normal hindpaw, to evaluate drugs for analgesic action. The apparatus exerts a steadily increasing force and reaction threshold is determined as the pressure (g) required to elicit paw withdrawal and/or vocalization.

Fourteen days after surgery, nociceptive reaction thresholds were measured in order to select animals meeting the inclusion criteria: 20 g<paw withdrawal threshold<240 g (baseline).

In the experiment, static mechanical hyperalgesia was assessed. Each reaction threshold was measured for both hind paws.

Five experimental groups of 10 rats each were used: CCI (chronic constriction injury)/vehicle (0.5% HPMC, i.p.); CCI/MIN-117 (1 mg/kg, i.p.); CCI/MIN-117 (3 mg/kg, i.p.); CCI/MIN-117 (10 mg/kg, i.p.); and CCI/morphine (3 mg/kg, s.c.).

Vehicle and MIN-117 were intraperitoneally administered at 10 mL/kg. Morphine was subcutaneously administered at 5 mL/kg. Dosing and testing were performed in a random order by a blinded experimenter except for the morphine-treated group.

Thirty minutes after morphine injection, the antihyperalgesic effect of morphine was evaluated using the paw pressure test. For vehicle and MIN-117 administration, the antihyperalgesic effect of the was evaluated after 120 min. using the paw pressure test.

Rats were sacrificed at the end of the experiment by $CO_2$ inhalation.

After 14 days, sciatic nerve ligation induced a marked, significant, and homogeneous decrease in the nociceptive thresholds in the 5 experimental groups.

The 0.5% HPMC-treated group exhibited, for the injured paw, a stable nociceptive threshold 120 min. after treatment.

Morphine subcutaneously administered at 3 mg/kg induced a pronounced and significant increase in the nociceptive threshold 30 min. after the administration.

Intraperitoneal administration of MIN-117 at 1 mg/kg did not induce any significant increase in the nociceptive threshold, 120 min. after treatment. However, when MIN-117 was administered at 3 and 10 mg/kg, after 120 min. it induced a significant increase in the nociceptive thresholds.

The antihyperalgesic effect of a single intraperitoneal administration of MIN-117 in a model of carrageenan-induced mechanical hyperalgesia in rats was also assessed.

In this model, inflammation is induced by intraplantar injection of carrageenan (2%) into the right hindpaw of the rat. Three hours later, reaction thresholds are measured using the paw pressure test. Pressure is gradually applied to both hind paws (inflamed and control) of the rat, and reaction thresholds are determined as the pressure (g) required to elicit paw withdrawal or vocalization. Morphine (3 mg/kg, s.c.) was used as a positive control.

This assay is widely and reliably used for revealing the efficacy of new analgesics in a model of inflammatory pain in conscious rats.

Five experimental groups of 10 rats each were used. Each group was first injected with 100 μL of a 2% carrageenan suspension was injected into the plantar aspect of the right hindpaw. Three hours after carrageenan injection, nociceptive reaction thresholds (vocalization or paw withdrawal) were measured in order to select animals meeting the inclusion criteria: 20 g<paw withdrawal threshold<240 g (baseline). The 5 groups were then administered the following: vehicle (0.5% HPMC, i.p.); MIN-117 (1 mg/kg, i.p.); MIN-117 (3 mg/kg, i.p.); MIN-117 (10 mg/kg, i.p.); and morphine (3 mg/kg, s.c.).

Thirty minutes after morphine injection, the antihyperalgesic effect of morphine was evaluated using the paw pressure test. For vehicle and MIN-117 administration, the antihyperalgesic effect was evaluated after 120 min. using the paw pressure test.

Vehicle and MIN-117 were intraperitoneally administered at 10 mL/kg. Morphine was subcutaneously administered at 5 mL/kg. Dosing and testing were performed in a random order by a blinded experimenter except for the morphine-treated group. Doses were expressed in terms of free active substance.

Before dosing, all the groups exhibited a significantly reduced nociceptive threshold for the injured paw as compared to the control paw 3 h after injection of a 2% carrageenan suspension. Rats from the vehicle-treated group exhibited, for the injured paw, a stable nociceptive threshold 120 min. after treatment. Subcutaneously administered at 3 mg/kg, morphine induced a marked and significant increase in the nociceptive threshold 30 min. after the injection.

Intraperitoneal administration of MIN-117 at 1 mg/kg did not induce any significant increase in the nociceptive threshold. When administered at 3 and 10 mg/kg, however, MIN-117 induced, 120 min. later, a significant increase in the nociceptive thresholds.

Assessment of neuropathic pain using von Frey filaments was also performed. Rats were administered paclitaxel (2 mg/kg) on four alternate days (days 1, 3, 5 and 7). Baseline and post treatment paw withdrawal thresholds (PWT) were evaluated using von Frey filaments Animals were placed on a perforated metallic platform and allowed to acclimate to their surroundings for a minimum of 15 minutes before each test session. Each filament was presented perpendicular to the plantar surface with sufficient force to cause slight buckling against the paw, and then held until a positive response is noted (paw sharply withdrawn). As described by Chaplan, S. R. et al., once the threshold was crossed, the 2 responses straddling the threshold are retrospectively designated as the first 2 responses. Four additional responses were measured to stimuli varied sequentially up or down based on the animal's response.

Paclitaxel was injected i.p. (2 mg/kg) on four alternate days (day 1, 3, 5 and 7) for a total of 4 injections at a dose volume of 1 mL/kg.

On day 14, baseline von Frey responses were measured to ensure all rats showed a stable neuropathic pain response. Rats were subsequently balanced and assigned to treatment groups based on post-paclitaxel PWT values. On test day, PWT was assessed two hours post vehicle or MIN-117 injections and one hour after gabapentin administration.

The effects of Gabapentin or MIN-117 on PWT at Day 14 were assessed. Gabapentin was administered orally 60 minutes prior to test at a dose volume of 1 mL/kg. MIN-117 (1, 3 and 10 mg/kg) was administered i.p. at a dose volume of 1 mL/kg. MIN-117 was administered 2 hours prior to test.

One-way ANOVA indicated significant differences between groups. Gabapentin showed a significant increase in PWT compared to the vehicle. Animals treated with MIN-117 (3 and 10 mg/kg) also showed a significant increase in PWT compared to vehicle.

The analgesic efficacy of MIN-117 in a rat model of chemotherapy-induced peripheral neuropathic pain following chronic injection was assessed. Reference formulations: paclitaxel (2 mg/kg), was injected i.p. on four alternate days (day 1, 3, 5 and 7) for a total of 4 injections at a dose volume of 1 mL/kg. Gabapentin (100 mg/kg) was dissolved in saline and administered orally at a dose volume of 1 mL/kg. In a prevention study, MIN-117 (10 mg/kg) was administered i.p once daily for 7 or 14 days at a dose volume of 1 mL/kg. On test days, MIN-117 was administered 2 hours prior to test.

In a reversal study, MIN-117 (1, 3 and 10 mg/kg) administered i.p once daily for 2 weeks at a dose volume of 1 mL/kg. On test days, MIN-117 was administered 2 hours prior to test.

For the prevention study a single dose was tested (10 mg/kg) and was injected for either 7 or 14 days starting one day prior to paclitaxel. Under this treatment regimen, significant increases in PWT was seen 10 and 14 days after administration when compared to vehicle.

For the reversal study MIN-117 was tested at 1, 3, and 10 mg/kg following 2 weeks administration. All doses showed significant increase in PWT when tested on days 1, 7 and 14 of MIN-117 treatment corresponding to days 14, 21 and 28 from commencing the study.

When rats were tested one week following cessation of treatment, no analgesic effects were seen at any of the doses of MIN-117 in either study suggesting the effects were not long lasting.

Gabapentin when administered chronically or acutely showed a significant increase in PWT. The analgesic effects of gabapentin were not long lasting either and after cessation of treatment, no significant effect on PWT was seen when compared to vehicle.

Two classes of antidepressants were also evaluated in Paw Withdrawal Threshold (PWT) experiments: duloxetine, a serotonin norepinephrine reuptake inhibitor, and amitriptyline, a tricyclic antidepressant. It was shown that duloxetine had no effect on PWT in paclitaxel-treated rats, i.e., duloxetine was not found to reverse paclitaxel-induced neuropathy in rats. It was shown that amitriptyline only partially reversed this neuropathy, but only at the highest dose tested (30 mg/kg).

Further aspects of this application, include:

A. A method of treating pain comprising administering to a subject in need of treatment a therapeutically effective amount of Compound I, or a pharmaceutically acceptable salt or solvate thereof.

B. A method of treating pain comprising administering to a subject in need of treatment a therapeutically effective amount of a pharmaceutically acceptable salt of Compound I.

C. A method of treating pain comprising administering to a subject in need of treatment a therapeutically effective amount of a hydrochloride salt of Compound I.

D. A method of treating pain comprising administering to a subject in need of treatment a therapeutically effective amount of Compound I, or a pharmaceutically acceptable salt or solvate thereof, wherein the pain is acute, chronic, toxic, neuropathic, nociceptive, inflammatory, post-operative, visceral, chemotherapy-induced pain, or a combination thereof. For example, the pain is chemotherapy-induced peripheral neuropathic pain.

E. A method of treating fibromyalgia comprising administering to a subject in need of treatment a therapeutically effective amount of Compound I, or a pharmaceutically acceptable salt or solvate thereof.

F. A method of treating fibromyalgia comprising administering to a subject in need of treatment a therapeutically effective amount of a pharmaceutically acceptable salt of Compound I.

G. A method of treating fibromyalgia comprising administering to a subject in need of treatment a therapeutically effective amount of a hydrochloride salt of Compound I.

H. A method of treating neuropathy comprising administering to a subject in need of treatment a therapeutically effective amount of Compound I, or a pharmaceutically acceptable salt or solvate thereof.

I. A method of treating neuropathy comprising administering to a subject in need of treatment a therapeutically effective amount of a pharmaceutically acceptable salt of Compound I.

J. A method of treating neuropathy comprising administering to a subject in need of treatment a therapeutically effective amount of a hydrochloride salt of Compound I. For example, the neuropathy is peripheral neuropathy. For example, the neuropathy is induced by chemotherapy.

K. A method of treating chemotherapy-induced peripheral neuropathic pain comprising administering to a subject in need of treatment a therapeutically effective amount of Compound I, or a pharmaceutically acceptable salt or solvate thereof.

L. A method of treating chemotherapy-induced peripheral neuropathic pain comprising administering to a subject in need of treatment a therapeutically effective amount of a pharmaceutically acceptable salt of Compound I.

M. A method of treating chemotherapy-induced peripheral neuropathic pain comprising administering to a subject in need of treatment a therapeutically effective amount of a hydrochloride salt of Compound I.

N. Any of the methods disclosed herein, the treatment with a therapeutically effective amount of Compound I, or a pharmaceutically acceptable salt or solvate thereof, promotes an antihyperalgesic effect in the subject.

O. Any of the methods disclosed herein, including those in Aspects A-N, wherein the therapeutically effective amount of Compound I, or a pharmaceutically acceptable salt or solvate thereof, is 0.1 mg/kg to 100 mg/kg. For example, 10 mg/kg.

P. Any of the methods disclosed herein, including those in Aspects A-N, wherein the therapeutically effective amount of Compound I, or a pharmaceutically acceptable salt or solvate thereof, is 0.5 mg/kg to 50 mg/kg.

Q. Any of the methods disclosed herein, including those in Aspects A-N, wherein the therapeutically effective amount of Compound I, or a pharmaceutically acceptable salt or solvate thereof, is 1 mg/kg to 20 mg/kg.

R. Any of the methods disclosed herein, including those in Aspects A-N, wherein the amount of Compound I, or a pharmaceutically acceptable salt or solvate thereof, administered to the subject is 0.1 mg to 6,000 mg.

S. Any of the methods disclosed herein, including those in Aspects A-N, wherein the amount of Compound I, or a pharmaceutically acceptable salt or solvate thereof, administered to the subject is 1 mg to 1,000 mg.

T. Any of the methods disclosed herein, including those in Aspects A-N, wherein the amount of Compound I, or a pharmaceutically acceptable salt or solvate thereof, administered to the subject is 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 mg.

U. Any of the methods disclosed herein, including those in Aspects A-N, wherein the amount of Compound I, or a pharmaceutically acceptable salt or solvate thereof, administered to the subject is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg.

V. Any of the methods disclosed herein, including those in Aspects A-N, wherein the amount of Compound I, or a pharmaceutically acceptable salt or solvate thereof, is administered to the subject once a day, twice a day, three times a day, once every two days, once every three days, once every four days, once every five days, once every six days, once a week, once every two weeks, once every three weeks, or once a month.

W. Any of the methods disclosed herein, including those in Aspects A-N, wherein Compound I, or a pharmaceutically acceptable salt or solvate thereof, is formulated as a pharmaceutical composition comprising one or more pharmaceutically acceptable excipients.

X. Any of the methods disclosed herein, including those in Aspects A-N, wherein the pharmaceutical composition further comprises an additional therapeutic agent for the treatment of pain.

Y. Any of the methods disclosed herein, including those in Aspects A-N, wherein Compound I, or a pharmaceutically acceptable salt or solvate thereof, or a pharmaceutical composition comprising Compound I, or a pharmaceutically acceptable salt or solvate thereof, is administered orally, parenterally, intravenously, intramuscularly, intrathecally, subcutaneously, topically, systemically, cutaneously, sublingually, buccally, rectally, vaginally, ocularly, otically, nasally, by inhalation, or by nebulization, or transdermally.

Z. Any of the methods disclosed herein, including those in Aspects A-N, wherein Compound I, or a pharmaceutically acceptable salt or solvate thereof, or a pharmaceutical composition comprising Compound I, or a pharmaceutically acceptable salt or solvate thereof, is administered to the subject orally and is formulated as a tablet, capsule, chew, gel, paste, multi-particulate, nano-particulate, lozenge, pastille, granule, powder, solution, spray, emulsion, suspension, syrup, mouthwash, or drop.

AA. Any of the methods disclosed herein, including those in Aspects A-N, wherein Compound I, or a pharmaceutically acceptable salt or solvate thereof, or a pharmaceutical composition comprising Compound I, or a pharmaceutically acceptable salt or solvate thereof, is administered to the subject topically and is formulated as a cream, paste, lotion, gel, patch, or spray.

BB. Any of the methods disclosed herein, including those in Aspects A-N, further comprising administering an additional therapeutic agent for the treatment of pain.

CC. Any of the methods disclosed herein, including those in Aspects A-N, further comprising administering an additional therapeutic agent for the treatment of pain, wherein the additional therapeutic agent for the treatment of pain and Compound I, or a pharmaceutically acceptable salt or solvate thereof, or a pharmaceutical composition comprising Compound I, or a pharmaceutically acceptable salt or solvate thereof, are administered in temporal proximity.

DD. Any of the methods disclosed herein, including those in Aspects A-N, wherein the subject is a human.

EE. A pharmaceutical composition comprising Compound I, or a pharmaceutically acceptable salt or solvate thereof, for use in treating pain in a subject in need of treatment. For example, a pharmaceutical composition comprising the hydrochloride salt of Compound I for use in treating pain in a subject in need of treatment.

FF. Compound I, or a pharmaceutically acceptable salt or solvate thereof, for use in treating pain in a subject in need of treatment. For example, the hydrochloride salt of Compound I for use in treating pain in a subject in need of treatment.

GG. Compound I, or a pharmaceutically acceptable salt or solvate thereof, in the manufacture of a medicament for treating pain in a subject in need of treatment. For example, the hydrochloride salt of Compound I in the manufacture of a medicament for treating pain in a subject in need of treatment.

Equivalents

Those skilled in the art will recognize, or be able to ascertain using no more than routine experimentation, many equivalents to the specific embodiments and methods described herein. Such equivalents are intended to be encompassed by the scope of the present application. All patents, patent applications, and literature references cited herein are hereby expressly incorporated by reference in their entirety.

Citation of publications and patent documents is not intended as an admission that any is pertinent prior art, nor does it constitute any admission as to the contents or date of the same.

The invention having now been described by way of written description, those of skill in the art will recognize that the invention can be practiced in a variety of embodiments and that the foregoing description and examples below are for purposes of illustration and not limitation of the claims that follow.

EXAMPLES

Example 1

Assessment of the Efficacy of a Single Administration of MIN-117 at 2 Doses in ALGOGram™ (High Throughput Screening in Rats)

The effect of a single administration of MIN-117 at 2 doses in ALGOGram™ is summarized in FIG. 1. Various pain areas (acute and toxic pain; neuropathic pain; inflammatory pain; post-operative pain; visceral pain; and behavior and acute toxicity) were assessed using model test at 0.1 mg/kg MIN-117 and 1.0 mg/kg MIN-117 (i.p.). For each test, an internal reference (e.g., morphine) was used as a control for comparison. Testing was done 2 hours after treatment. n=4/model/test. Results are expressed for each group as a percentage of activity calculated from the mean value of the vehicle-treated animals and compared to naïve animals, control paw, or cut-off value, depending on the test.

Example 2

Assessment of the Antihyperalgesic Effect of a Single Intraperitoneal Administration of MIN-117 in a Model of Carrageenan-Induced Mechanical Hyperalgesia in Rats The antihyperalgesic effect of a single intraperitoneal administration of MIN-117 in a model of carrageenan-induced mechanical hyperalgesia in rats was assessed.

Carrageenan is a polysaccharide obtained from various seaweeds. When injected into the plantar paw or the knee joint, carrageenan results in a localized inflammation, therefore decreases weight bearing, modifies guarding of the treated limb and induced thermal and mechanical hyperalgesia/allodynia.

In this model, inflammation is induced by intraplantar injection of carrageenan (2%) into the right hindpaw of the rat. Three hours later, reaction thresholds are measured using the paw pressure test. Pressure is gradually applied to both hind paws (inflamed and control) of the rat, and reaction thresholds are determined as the pressure (g) required to elicit paw withdrawal or vocalization. Morphine (3 mg/kg, s.c.) was used as a positive control.

This assay is widely and reliably used for revealing the efficacy of new analgesics in a model of inflammatory pain in conscious rats.

The experiments in this study used fifty (50) male Sprague-Dawley rats (SPF status, Janvier, France), each weighing 204-260 grams. The rats were housed in a temperature (20-24° C.) and relative humidity (45%-65%) controlled room and acclimated to an artificial day/night cycle of 12 hours light (6.30 a.m. to 6.30 p.m.)/12 hours darkness. Rats had free access to sterilized tap water and were fed ad libitum with pelleted complete diet (reference A04, S.A.F.E.). Rats were housed 4 per cage (cages Type E) and were acclimated for a period of at least 5 days before any testing. Each rat was identified by tail markings. Based on the SPF status of the animal facilities, there is no reason to expect that contaminants were present in the food, water or bedding, at levels capable of interfering with the results of the tests.

MIN-117 was supplied by Minerva Neuroscience, Inc. as a white to pale yellowish power or crystalline powder and was stored at room temperature prior to use.

Morphine was supplied by Francopia (Catalog reference no. 3695, batch no. HR00002) and was stored at room temperature prior to use.

Vehicles (HPMC, water, saline) were stored at 4° C. 0.5% (w/v) hydroxypropylmethylcellulose (HPMC) 80-120 centipoises in water for injection was used as vehicle for MIN-117. 0.9% NaCl was used as vehicle for morphine.

Carrageenan was supplied by Sigma-Aldrich (Catalog reference no. C1013, batch no. SLBD1934V) and was stored in suspension at 4° C. 0.9 NaCl (w/v) was used vehicle for 2% carrageenan suspension.

Ugo Basile Analgesimeter (Ugo Basile, Italy) was used for the paw pressure test.

SigmaStat software version 3.5 (SPSS Science Software, Erkrath, Germany) and Lab X direct software version 2.4 (Mettler Toledo, France) were used for data processing.

Pain Test: Static mechanical hyperalgesia was assessed using the Paw Pressure test or Randall & Selitto test (Randall, L. O. and Selitto, J. J., A method for measurement of analgesic activity on inflamed tissue, *Arch Int Pharmacodyn,* 1957(111): 409-419). This test requires the application of an increasing pressure on the hind paws between a flat surface and a blunt pointer. This test is usually used with animals with one hind paw inflamed by an injection or injured by ligation, and one normal hind paw, to evaluate drugs for analgesic action. The apparatus exerts a steadily increasing force and reaction threshold is determined as the pressure (g) required to elicit paw withdrawal and/or vocalization. In the experiment, animals were gently handled by the experimenter and static mechanical hyperalgesia was assessed. Each reaction threshold measurement was done for both hind paws.

Five (5) experimental groups of 10 rats each were used. Each group was first injected with of 100 μL of a 2% carrageenan suspension in the plantar aspect of the right hindpaw. Three hours after carrageenan injection, paw withdrawal threshold was measured using the paw pressure test (Baseline). The 5 groups were then administered the following:

Group 1: vehicle (0.5% HPMC), i.p., solution (negative control);

Group 2: MIN-117 (0.01 mg/kg, i.p.) in 0.5% HPMC, suspension;

Group 3: MIN-117 (0.1 mg/kg, i.p.) in 0.5% HPMC, suspension;

Group 4: MIN-117 (1 mg/kg, i.p.) in 0.5% HPMC, suspension; and

Group 5: morphine (3 mg/kg, s.c.) in 0.9% NaCl, solution (positive control).

After administering vehicle, MIN-117, or morphine, the antihyperalgesic effect of the compounds was evaluated using the paw pressure test at 0 min. ($T_0$), 30 min., 60 min., 120 min., and 240 min.

Vehicle and MIN-117 were administered intraperitoneally at 10 mL/kg. Morphine was subcutaneously administered at 5 mL/kg. Dosing and testing were performed in a random order by a blinded experimenter except for the morphine-treated group. Doses were expressed in terms of free active substance. Rats were sacrificed at the end of the experiment by $CO_2$ inhalation pending subsequent removal by a certified company.

Results were assessed as: the paw withdrawal threshold (mean±s.e.m.) in grams of contact pressure for each group, calculated from individual paw withdrawal thresholds; the percentage of variation of the paw withdrawal threshold calculated from the mean value of the vehicle-treated group; and/or the percentage of activity. To determine a statistical effect of the test substance and the reference substance, data were analyzed by a non-parametrical test. The significance level was $p<0.05$.

Figure 2:
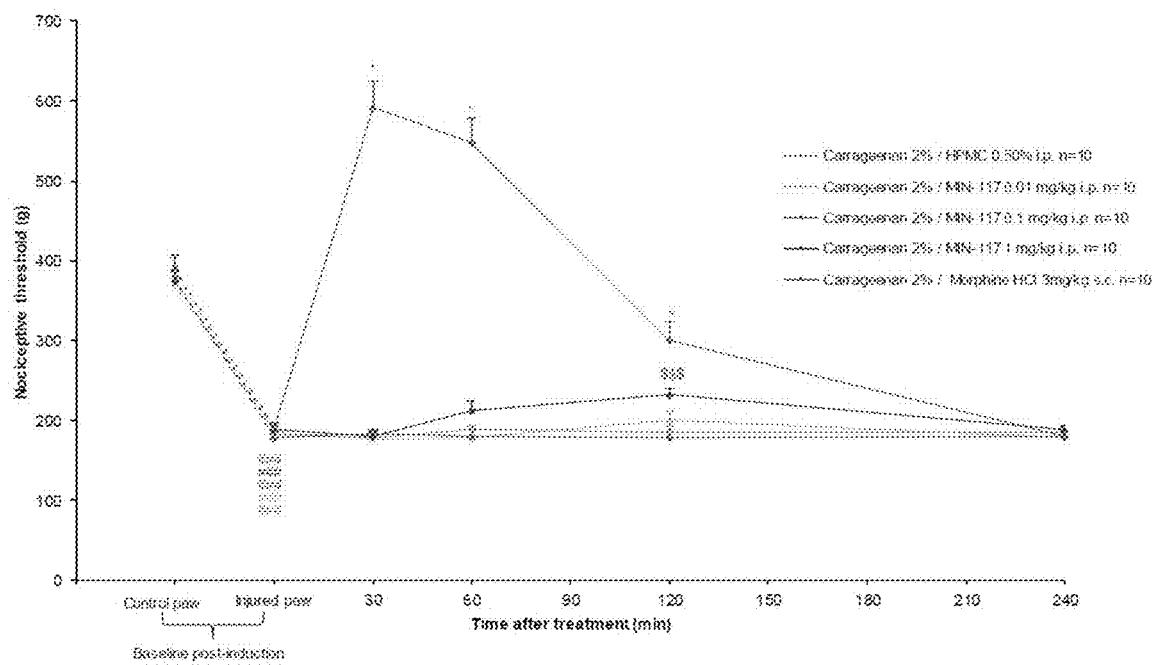
FIG. 2 is a graph showing the effect of a single i.p. administration of MIN-117 (at 0.01, 0.1, and 1 mg/kg i.p.), morphine (3 mg/kg i.p., positive control), and vehicle (negative control) in a model of carrageenan-induced mechanical hyperalgesia (injured paw) in rats. Results are expressed as mean±s.e.m. (###: $p<0.05$ as compared to the control (uninjured) paw of the corresponding group, Mann-Whitney rank sum test.) (*: $p<0.05$ as compared to the vehicle-treated group, Tuckey's test after significant Kruskal-Wallis one-way ANOVA on ranks) ($$$: $p<0.001$ as compared to the vehicle-treated group, Mann-Whitney rank sum test.)

As summarized in Table 1 and FIG. 2, the raw data in Table 2 show that before dosing all the treatment groups exhibited a significantly reduced nociceptive threshold of the injured paw ranged from 50% to 53% ($p<0.001$) as compared to the control paw. Rats from the vehicle-treated group (0.5% HPMC) exhibited, for the injured paw, reduced and stable nociceptive thresholds as compared to the control paw throughout the observation period of the study (ranged between 178±7.0 g at $T_0$+30 min. and 188±6.1 g at $T_0$+60 min). Morphine, subcutaneously administered at 3 mg/kg, induced a marked and significant increase in the injured paw withdrawal threshold from 30 min. to 120 min. after administration with a maximum effect reached 30 min. after treatment (592±31.3 g vs 178±7.0 g, +233%, $p<0.05$) as compared to the vehicle-treated group. MIN-117 intraperitoneally administered at 0.01 or 0.1 mg/kg did not induce any significant increase in the paw withdrawal threshold throughout the time course study. However, MIN-117 intraperitoneally administered at 1 mg/kg induced a slight increase in the nociceptive threshold becoming significant 120 min. after injection (See $$$ in FIG. 2) as compared to the vehicle-treated group (232±7.4 g vs 186±7.3, +25%, $p<0.001$, Mann-Whitney rank sum test).

TABLE 1

| Reagent | Carrageenan 2% | Carrageenan 2% | Carrageenan 2% | Carrageenan 2% | Carrageenan 2% |
|---|---|---|---|---|---|
| Substance | HPMC | MIN-117 | MIN-117 | MIN-117 | Morphine |
| Dose | 0.5% | 0.01 mg/kg | 0.1 mg/kg | 1 mg/kg | 3 mg/kg |
| Route of administration | i.p. | i.p. | i.p. | i.p. | s.c. |

T0

Control paw

| | | | | | |
|---|---|---|---|---|---|
| Nociceptive threshold (g) | 388.0 ± 14.7 | 370.0 ± 9.1 | 378.0 ± 10.5 | 374.0 ± 12.7 | 390.0 ± 15.6 |
| n | 10 | 10 | 10 | 10 | 10 |

Injured paw

| | | | | | |
|---|---|---|---|---|---|
| Nociceptive threshold (g) | 182 ± 5.5 | 186 ± 7.3 | 178 ± 5.5 | 188 ± 9.0 | 192 ± 5.3 |
| % variation vs vehicle-treated group | — | 2% | −2% | 3% | 5% |
| % variation vs control paw | −53% | −50% | −53% | −50% | −51% |
| % activity | — | 2% | −2% | 3% | 2% |
| Statistical analysis | ### | ### | ### | ### | ### |

T0 + 30 min

Injured paw

| | | | | | |
|---|---|---|---|---|---|
| Nociceptive threshold (g) | 178 ± 7.0 | 176 ± 8.3 | 184 ± 5.0 | 180 ± 7.3 | 592 ± 31.3 |
| % variation vs pre-drug threshold | −2% | −5% | 3% | −4% | 208% |
| % variation vs vehicle-treated group | — | −1% | 3% | 1% | 233% |
| % variation vs control paw | −50% | −51% | −48% | −49% | −11% |
| % activity | — | −1% | 3% | 1% | 230% |
| Statistical analysis | — | NS | NS | NS | * |

T0 + 60 min

Injured paw

| | | | | | |
|---|---|---|---|---|---|
| Nociceptive threshold (g) | 188 ± 6.1 | 178 ± 10.1 | 180 ± 7.9 | 212 ± 12.4 | 548 ± 31.3 |
| % variation vs pre-drug threshold | 3% | −4% | 1% | 13% | 185% |
| % variation vs vehicle-treated group | — | −5% | −4% | 13% | 191% |
| % variation vs control paw | −47% | −49% | −48% | −45% | −16% |
| % activity | — | −6% | −5% | 14% | 214% |
| Statistical analysis | — | NS | NS | NS | * |

T0 +120 min

Injured paw

| | | | | | |
|---|---|---|---|---|---|
| Nociceptive threshold (g) | 186 ± 7.3 | 200 ± 12.6 | 178 ± 7.6 | 232 ± 7.4 | 300 ± 23.5 |
| % variation vs pre-drug threshold | 2% | 8% | 0% | 23% | 56% |
| % variation vs vehicle-treated group | — | 8% | −4% | 25% | 61% |
| % variation vs control paw | −46% | −48% | −50% | −41% | −31% |
| % activity | — | 9% | −5% | 29% | 72% |
| Statistical analysis | — | NS | NS | $$$ | * |

T0 + 240 min

Injured paw

| | | | | | |
|---|---|---|---|---|---|
| Nociceptive threshold (g) | 186 ± 6.0 | 178 ± 6.3 | 180 ± 8.4 | 188 ± 6.1 | 180 ± 8.9 |
| % variation vs pre-drug threshold | 2% | −4% | 1% | 0% | −6% |
| % variation vs vehicle-treated group | — | −4% | −3% | 1% | −3% |
| % variation vs control paw | −47% | −49% | −49% | −49% | −49% |
| % activity | — | −5% | −4% | 1% | −4% |
| Statistical analysis | — | NS | NS | NS | NS |

TABLE 2

| Substances | Rat | Weight (g) | Baseline control paw | Baseline injured paw | 30 control paw | 30 injured paw | 60 control paw | 60 injured paw | 120 control paw | 120 injured paw | 240 control paw | 240 injured paw |
|---|---|---|---|---|---|---|---|---|---|---|---|---|
| Carrageenan 2%/ HPMC 0.50% i.p. n = 10 | 3 | 204 | 360 | 180 | 300 | 200 | 320 | 160 | 340 | 180 | 340 | 180 |
| | 7 | 223 | 400 | 180 | 360 | 140 | 340 | 180 | 340 | 200 | 320 | 160 |
| | 11 | 214 | 400 | 140 | 340 | 180 | 360 | 180 | 320 | 160 | 340 | 180 |
| | 16 | 205 | 300 | 180 | 320 | 160 | 300 | 180 | 280 | 140 | 320 | 180 |
| | 22 | 235 | 400 | 180 | 340 | 180 | 380 | 180 | 340 | 200 | 380 | 160 |
| | 27 | 207 | 460 | 180 | 420 | 180 | 400 | 200 | 360 | 220 | 340 | 200 |
| | 38 | 230 | 440 | 200 | 360 | 180 | 360 | 180 | 320 | 180 | 400 | 220 |
| | 41 | 248 | 380 | 200 | 380 | 220 | 420 | 220 | 380 | 200 | 400 | 200 |
| | 46 | 214 | 400 | 180 | 380 | 180 | 360 | 220 | 340 | 180 | 340 | 180 |
| | 55 | 226 | 340 | 200 | 380 | 160 | 320 | 180 | 420 | 200 | 360 | 200 |

TABLE 2-continued

| Substances | Rat | Weight (g) | Baseline control paw | Baseline injured paw | 30 control paw | 30 injured paw | 60 control paw | 60 injured paw | 120 control paw | 120 injured paw | 240 control paw | 240 injured paw |
|---|---|---|---|---|---|---|---|---|---|---|---|---|
| Mean | | 220.6 | 388 | 182 | 358 | 178 | 356 | 188 | 344 | 186 | 354 | 186 |
| S.E.M | | 4.6 | 14.7 | 5.5 | 10.9 | 7.0 | 11.9 | 6.1 | 11.9 | 7.3 | 9.5 | 6.0 |
| n | | | 10.0 | 10.0 | 10.0 | 10.0 | 10.0 | 10.0 | 10.0 | 10.0 | 10.0 | 10.0 |
| % variation vs pre-drug threshold | | | — | — | — | −2% | — | 3% | — | 2% | — | 2% |
| % variation vs control paw | | | — | −53% | — | −50% | — | −47% | — | −46% | — | −47% |
| Carrageenan | 4 | 221 | 400 | 240 | 360 | 180 | 380 | 220 | 440 | 300 | 340 | 200 |
| 2%/ | 10 | 221 | 380 | 180 | 360 | 180 | 340 | 160 | 360 | 180 | 360 | 180 |
| MIN-117 | 15 | 232 | 320 | 180 | 380 | 220 | 320 | 180 | 340 | 160 | 380 | 180 |
| 0.01 mg/kg | 17 | 206 | 380 | 180 | 380 | 160 | 320 | 140 | 320 | 160 | 300 | 160 |
| i.p. | 25 | 229 | 360 | 200 | 360 | 140 | 340 | 160 | 400 | 200 | 320 | 140 |
| n = 10 | 30 | 245 | 400 | 180 | 380 | 160 | 360 | 220 | 420 | 200 | 360 | 160 |
| | 34 | 221 | 400 | 160 | 420 | 200 | 420 | 220 | 360 | 220 | 420 | 200 |
| | 36 | 222 | 340 | 180 | 360 | 200 | 360 | 180 | 420 | 200 | 380 | 200 |
| | 42 | 246 | 340 | 200 | 340 | 180 | 340 | 140 | 380 | 180 | 320 | 180 |
| | 48 | 247 | 380 | 160 | 280 | 140 | 300 | 160 | 400 | 200 | 320 | 180 |
| Mean | | 229 | 370 | 186 | 362 | 176 | 348 | 178 | 384 | 200 | 350 | 178 |
| S.E.M | | 4.3 | 9.1 | 7.3 | 11.3 | 8.3 | 10.8 | 10.1 | 12.2 | 12.6 | 11.6 | 6.3 |
| n | | | 10.0 | 10.0 | 10.0 | 10.0 | 10.0 | 10.0 | 10.0 | 10.0 | 10.0 | 10.0 |
| % variation vs pre-drug threshold | | | — | — | — | −5% | — | −4% | — | 8% | — | −4% |
| % variation vs vehicle treated group | | | — | 2% | — | 1% | — | 5% | — | 8% | — | −4% |
| % variation vs control paw | | | — | −50% | — | −51% | — | −49% | — | −48% | — | −49% |
| % activity | | | — | 2% | — | −1% | — | −6% | — | 9% | — | −5% |
| Carrageenan | 5 | 234 | 420 | 200 | 440 | 200 | 360 | 180 | 380 | 160 | 400 | 180 |
| 2%/ | 8 | 222 | 380 | 180 | 320 | 160 | 300 | 140 | 280 | 140 | 320 | 160 |
| MIN-117 | 18 | 221 | 400 | 180 | 460 | 200 | 420 | 180 | 420 | 160 | 340 | 180 |
| 0.1 mg/kg | 23 | 205 | 360 | 200 | 300 | 160 | 300 | 160 | 300 | 160 | 280 | 140 |
| i.p. | 51 | 219 | 420 | 160 | 320 | 180 | 400 | 160 | 420 | 220 | 400 | 220 |
| n = 10 | 26 | 223 | 380 | 180 | 320 | 180 | 320 | 200 | 340 | 200 | 360 | 180 |
| | 33 | 229 | 400 | 200 | 360 | 200 | 360 | 200 | 360 | 200 | 360 | 220 |
| | 45 | 217 | 340 | 160 | 340 | 200 | 360 | 200 | 340 | 180 | 380 | 200 |
| | 47 | 226 | 320 | 160 | 340 | 180 | 340 | 220 | 340 | 180 | 300 | 160 |
| | 56 | 230 | 360 | 160 | 340 | 180 | 320 | 160 | 360 | 180 | 360 | 160 |
| Mean | | 222.6 | 378 | 178 | 354 | 184 | 348 | 180 | 354 | 178 | 350 | 180 |
| S.E.M | | 2.6 | 10.5 | 5.5 | 16.9 | 5.0 | 12.7 | 7.9 | 14.3 | 7.6 | 12.7 | 8.4 |
| n | | | 10.0 | 10.0 | 10.0 | 10.0 | 10.0 | 10.0 | 10.0 | 10.0 | 10.0 | 10.0 |
| % variation vs pre-drug threshold | | | — | — | — | 3% | — | 1% | — | 0% | — | 1% |
| % variation vs vehicle treated group | | | — | −2% | — | 3% | — | −4% | — | −4% | — | −3% |
| % variation vs control paw | | | — | −53% | — | −48% | — | −48% | — | −50% | — | −49% |
| % activity | | | — | −2% | — | 3% | — | −5% | — | −5% | — | −4% |
| Carrageenan | 2 | 205 | 340 | 220 | 320 | 160 | 360 | 180 | 420 | 240 | 360 | 180 |
| 2%; | 9 | 207 | 360 | 220 | 320 | 160 | 360 | 180 | 360 | 200 | 320 | 180 |
| MIN-117 | 13 | 229 | 420 | 160 | 320 | 180 | 320 | 220 | 400 | 240 | 360 | 200 |
| 1 mg/kg | 19 | 221 | 340 | 140 | 300 | 140 | 320 | 140 | 320 | 200 | 280 | 160 |
| i.p. | 52 | 227 | 440 | 200 | 360 | 180 | 380 | 220 | 340 | 220 | 360 | 180 |
| n = 10 | 29 | 260 | 380 | 220 | 360 | 220 | 360 | 200 | 440 | 220 | 420 | 180 |
| | 35 | 252 | 420 | 180 | 320 | 180 | 360 | 240 | 360 | 220 | 340 | 180 |
| | 37 | 249 | 320 | 160 | 400 | 200 | 400 | 220 | 420 | 260 | 440 | 220 |
| | 44 | 259 | 360 | 180 | 440 | 200 | 520 | 280 | 460 | 260 | 400 | 180 |
| | 49 | 222 | 360 | 200 | 420 | 180 | 480 | 240 | 400 | 260 | 420 | 220 |
| Mean | | 233.1 | 374 | 188 | 356 | 180 | 380 | 212 | 392 | 232 | 370 | 188 |
| S.E.M | | 6.5 | 12.7 | 9.0 | 15.4 | 7.3 | 20.7 | 12.4 | 14.4 | 7.4 | 15.8 | 6.1 |
| n | | | 10.0 | 10.0 | 10.0 | 10.0 | 10.0 | 10.0 | 10.0 | 10.0 | 10.0 | 10.0 |
| % variation vs pre-drug threshold | | | — | — | — | 4% | — | 13% | — | 23% | — | 0% |
| % variation vs vehicle treated group | | | — | 3% | — | 1% | — | 13% | — | 25% | — | 1% |
| % variation vs control paw | | | — | −50% | — | −49% | — | −45% | — | −41% | — | −49% |
| % activity | | | — | 3% | — | 1% | — | 14% | — | 29% | — | 1% |
| Carrageenan | 1 | 210 | 320 | 160 | 680 | 600 | 580 | 440 | 480 | 280 | 320 | 160 |
| 2%/ | 6 | 246 | 440 | 200 | 680 | 620 | 680 | 600 | 320 | 280 | 360 | 180 |
| Morphine HCl | 14 | 205 | 420 | 220 | 680 | 560 | 680 | 460 | 440 | 260 | 320 | 160 |
| 3 mg/kg | 20 | 241 | 360 | 200 | 680 | 640 | 680 | 620 | 500 | 400 | 360 | 200 |
| s.c. | 24 | 221 | 460 | 180 | 680 | 680 | 680 | 680 | 440 | 320 | 360 | 240 |
| n = 10 | 28 | 229 | 380 | 200 | 680 | 680 | 680 | 620 | 380 | 280 | 400 | 160 |
| | 31 | 232 | 360 | 200 | 680 | 440 | 680 | 480 | 520 | 440 | 320 | 140 |
| | 39 | 255 | 420 | 180 | 680 | 620 | 680 | 600 | 460 | 320 | 420 | 200 |
| | 43 | 227 | 320 | 180 | 520 | 400 | 520 | 380 | 360 | 220 | 360 | 180 |
| | 50 | 238 | 420 | 200 | 680 | 680 | 680 | 600 | 440 | 200 | 320 | 180 |
| Mean | | 230.4 | 390. | 192 | 664 | 592 | 654 | 548 | 434 | 300 | 354 | 180 |
| S.E.M | | 4.9 | 15.6 | 5.3 | 16.0 | 31.3 | 17.9 | 31.3 | 20.0 | 23.5 | 11.2 | 8.9 |
| n | | | 10.0 | 10.0 | 10.0 | 10.0 | 10.0 | 10.0 | 10.0 | 10.0 | 10.0 | 10.0 |
| % variation vs pre-drug threshold | | | — | — | — | 208% | — | 185% | — | 56% | — | −6% |
| % variation vs vehicle treated group | | | — | 5% | — | 233% | — | 191% | — | 61% | — | −3% |
| % variation vs control paw | | | — | −51% | — | −11% | — | −16% | — | −31% | — | −49% |
| % activity | | | — | 2% | — | 230% | — | 214% | — | 72% | — | −4% |

Example 3

Assessment of the Antihyperalgesic Effect of a Single Intraperitoneal Administration of MIN-117 in a Model of Peripheral Mononeuropathy (Bennett Model) in Rats The antihyperalgesic effect of a single intraperitoneal administration of MIN-117 in a model of peripheral mononeuropathy (Bennett model) in rats was assessed.

The model of Chronic Constriction Injury (CCI) is based on a discrete peripheral nerve injury and can be related to post-traumatic/postsurgical neuropathic pain experienced by patients (Bennett, G. J. and Xie, Y. K., A peripheral mononeuropathy in rat that produces disorders of pain sensation like those seen in man, *Pain,* 1988(33):87-107). Unilateral peripheral mononeuropathy was induced by loose ligation of the rat the sciatic nerve of the right hindpaw in anaesthetized rats (xylazine 10 mg/kg i.p., ketamine 60 mg/kg i.p.). The common sciatic nerve was exposed at the level of the middle of the thigh by blunt dissection through the biceps femoris. Proximal to the sciatic trifurcation, four ligatures were tied loosely around it with about 1 mm spacing. Great care was taken to tie the ligatures, such that the diameter of the nerve was seen to be just barely constricted.

Fourteen days later, static mechanical hyperalgesia is assessed using the Paw pressure test (Randall, L. O. and Selitto, J. J., A method for measurement of analgesic activity on inflamed tissue, *Arch Int Pharmacodyn,* 1957(111):409-419). This test requires the application of an increasing pressure on the hind paws between a flat surface and a blunt pointer. This test is usually used with animals with one hindpaw inflamed by an injection or injured by ligation, and one normal hindpaw, to evaluate drugs for analgesic action. The apparatus exerts a steadily increasing force and reaction threshold is determined as the pressure (g) required to elicit paw withdrawal and/or vocalization. Ugo Basile Analgesimeter (Ugo Basile, Italy) was used for the paw pressure test.

Fourteen days after surgery ($D_0$), nociceptive reaction thresholds (vocalization or paw withdrawal) was measured in order to select animals meeting the inclusion criteria: 20 g<paw withdrawal threshold<240 g (baseline).

Fifty (50) male Sprague-Dawley rats (SPF status, Janvier, France), weighing 133-181 grams the day of surgery were used. Rats were housed in a temperature (20-24° C.) and relative humidity (45%-65%) controlled room and acclimated to an artificial day/night cycle of 12 hours light (6:30 a.m. to 6:30 p.m.)/12 hours darkness. Rats had free access to sterilized tap water and were fed ad libitum with pelleted complete diet (reference A04, S.A.F.E.). Animals were housed 4 per cage (cages Type E) and were acclimated for a period of at least 5 days before any testing. Each rat was identified by tail markings. Based on the SPF status of the animal facilities, there is no reason to expect that contaminants were present in the food, water or bedding, at levels capable of interfering with the results of the tests.

In the experiment, animals were gently handled by the experimenter and static mechanical hyperalgesia was assessed. Each reaction threshold was measured for both hind paws.

Five (5) experimental groups of 10 rats each were used:
Group 1: CCI (chronic constriction injury)/vehicle (0.5% HPMC), i.p., solution (negative control);
Group 2: CCI/MIN-117 (1 mg/kg, i.p.) in 0.5% HPMC, suspension;
Group 3: CCI/MIN-117 (3 mg/kg, i.p.) in 0.5% HPMC, suspension;
Group 4: CCI/MIN-117 (10 mg/kg, i.p.) in 0.5% HPMC, suspension; and
Group 5: CCI/morphine (3 mg/kg, s.c.) in 0.9% NaCl, solution (positive control).

MIN-117 was supplied by Minerva Neuroscience, Inc. as a white to pale yellowish power or crystalline powder and was stored at room temperature prior to use. Morphine was used as a reference substance as a positive control and was supplied by Francopia (Catalog reference no. 3695, batch no. HR00002) and stored at room temperature prior to use. Vehicles (HPMC, water, saline) were stored at 4° C. 0.5% (w/v) hydroxypropylmethylcellulose (HPMC) 80-120 centipoises in water for injection was used as vehicle for MIN-117. 0.9% NaCl was used as vehicle for morphine.

Vehicle and MIN-117 were intraperitoneally administered at 10 mL/kg. Morphine was subcutaneously administered at 5 mL/kg. Dosing and testing were performed in a random order by a blinded experimenter except for the morphine-treated group.

Thirty minutes after morphine injection, the antihyperalgesic effect of morphine was evaluated using the paw pressure test. For vehicle and MIN-117 administration, the antihyperalgesic effect of the was evaluated after 120 min. using the paw pressure test.

Rats were sacrificed at the end of the experiment by $CO_2$ inhalation pending subsequent removal by a certified company.

Results were expressed as:
The paw withdrawal threshold (mean±s.e.m.) in grams of contact pressure for each group, calculated from individual paw withdrawal thresholds
The percentage of variation of the paw withdrawal threshold calculated from the mean value of the vehicle-treated group
The percentage of activity of the compound on mechanical hyperalgesia induced by the sciatic nerve ligation, calculated as follows:

$$\frac{\text{(Nociceptive threshold injured paw)}_{treated} - \text{(Nociceptive threshold injured paw)}_{vehicle}}{\text{(Nociceptive threshold control paw)}_{vehicle} - \text{(Nociceptive threshold injured paw)}_{vehicle}}.$$

To determine a statistical effect of the test substances and the reference substance, data were analyzed by a non-parametrical test. SigmaStat software version 3.5 (SPSS Science Software, Erkrath, Germany) and Lab X direct software version 2.4 (Mettler Toledo, France) were used for data processing. The significance level was $p<0.05$.

Figure 3:
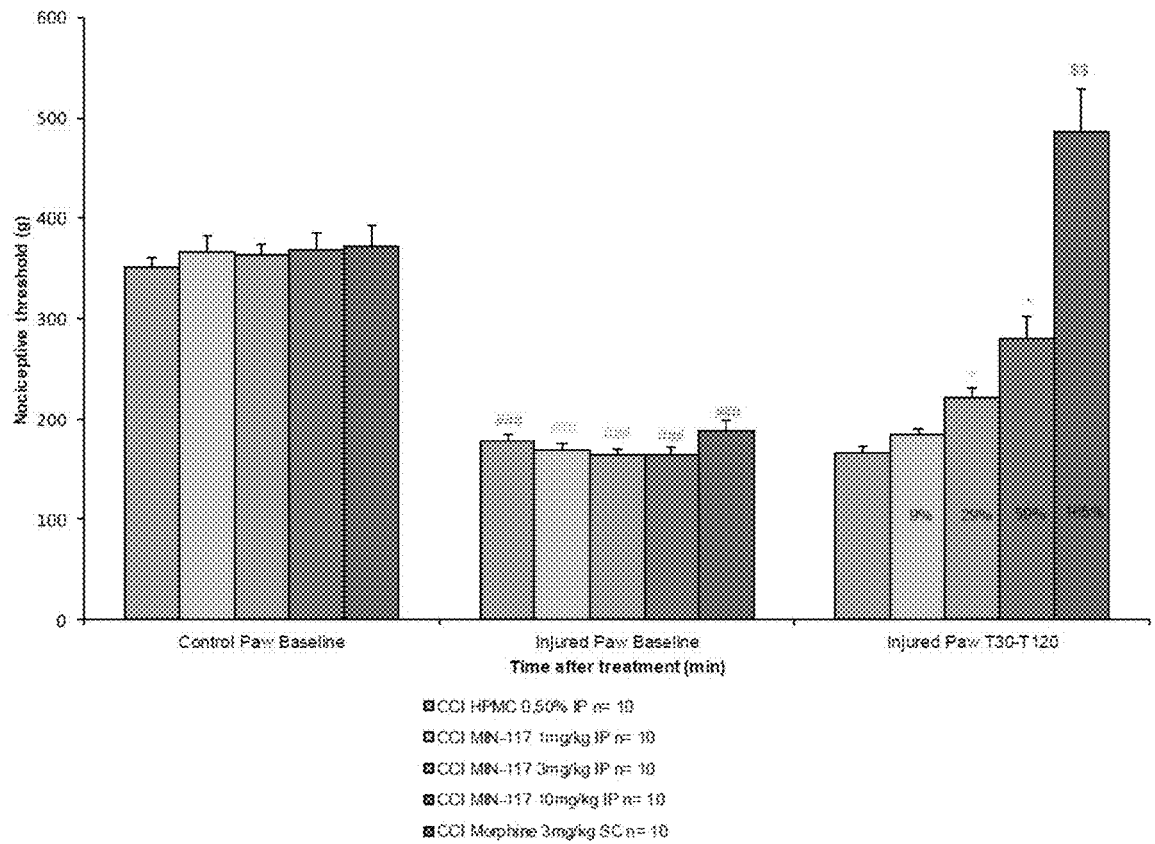
FIG. 3 is a series of bar graphs showing the effect of a single intraperitoneal administration of MIN-117 at various doses, morphine, and vehicle in a model of peripheral neuropathy in rats. Nociceptive threshold was measured 120 min. after vehicle or MIN-117 administration and 30 min. after morphine injection. Results are expressed as mean±s.e.m. Percentage are expressed as percentage of activity. (###: $p<0.001$ as compared to the control paw of the corresponding group, Mann-Whitney Rank sum test.) (*: $p<0.05$ as compared to the vehicle-treated group, Tuckey's test after significant Kruskal-Wallis one-way ANOVA on ranks.) ($$: $p<0.01$ as compared to the baseline of the corresponding group, Wilcoxon rank sum test).

As summarized in Table 3 and FIG. 3, the raw data in Table 4 show that after 14 days, sciatic nerve ligation induced a marked, significant, and homogeneous decrease in the nociceptive thresholds in the 5 experimental groups ranged between 49% and 55% as compared to the control paw ($p<0.001$).

The 0.5% HPMC-treated group exhibited (left-most columns in FIG. 3), for the injured paw, a stable nociceptive threshold 120 min. after treatment (166±6.7 g vs 178±6.3 g at $T_0$).

Morphine subcutaneously administered at 3 mg/kg (right-most columns in FIG. 3) induced a pronounced and significant increase in the nociceptive threshold 30 min. after the administration with a percentage of activity of +165% (486±42.8 g vs 188±10.4 g, p<0.01, as compared to the baseline pre-treatment).

Intraperitoneal administration of MIN-117 at 1 mg/kg (second columns from left in FIG. 3) did not induce any significant increase in the nociceptive threshold, 120 min. after treatment, as compared to the vehicle-treated group (percentage of activity: +9%). However, when MIN-117 was administered at 3 and 10 mg/kg (middle columns and second columns from right in FIG. 3, respectively), after 120 min. it induced a significant increase in the nociceptive thresholds as compared to the vehicle-treated group (respectively 222±9.2 g and 280±20.9 g vs 166±6.7 g) with a percentage of activity of +29% and +59% respectively.

TABLE 3

| Control paw T0 | | | | | |
|---|---|---|---|---|---|
| | Reagent | | | | |
| | CCI | CCI | CCI Substance | CCI | CCI |
| | HPMC | MIN-117 | MIN-117 Dose | MIN-117 | Morphine |
| | 0.5% | 1 mg/kg | 3 mg/kg | 10 mg/kg | 3 mg/kg |
| | | | Route of administration | | |
| | IP | IP | IP | IP | SC |
| Nociceptive threshold (g) | 350 ± 10.9 | 366 ± 16.1 | 364 ± 9.8 | 368 ± 16.9 | 372 ± 20.7 |
| n | 10 | 10 | 10 | 10 | 10 |

| Injured paw | | | | | |
|---|---|---|---|---|---|
| | Reagent | | | | |
| | CCI | CCI | CCI Substance | CCI | CCI |
| | HPMC | MIN-117 | MIN-117 Dose | MIN-117 | Morphine |
| | 0.5% | 1 mg/kg | 3 mg/kg | 10 mg/kg | 3 mg/kg |
| | | | Route of administration | | |
| | IP | IP | IP | IP | SC |
| Nociceptive threshold (g) | 178 ± 6.3 | 168 ± 8.0 | 164 ± 5.8 | 164 ± 7.2 | 188 ± 10.4 |
| % variation vs vehicle-treated group | — | −6% | −8% | −8% | 6% |
| % variation vs control paw | −49% | −54% | −55% | −55% | −49% |
| Statistical analysis | ### | ### | ### | ### | ### |

| Injured paw T0 + 30 min | | | | | |
|---|---|---|---|---|---|
| | Reagent | | | | |
| | CCI | CCI | CCI Substance | CCI | CCI |
| | HPMC | MIN-117 | MIN-117 Dose | MIN-117 | Morphine |
| | 0.5% | 1 mg/kg | 3 mg/kg | 10 mg/kg | 3 mg/kg |
| | | | Route of administration | | |
| | IP | IP | IP | IP | SC |
| Nociceptive threshold (g) | — | — | — | — | 486 ± 42.8 |
| % variation vs pre-drug threshold | — | — | — | — | 159% |
| % variation vs vehicle-treated group | — | — | — | — | — |
| % variation vs control paw | — | — | — | — | −23% |
| % activity | — | — | — | — | 165% |
| Statistical analysis | — | — | — | — | $$ |

TABLE 3-continued

| | Reagent | | | | |
|---|---|---|---|---|---|
| | CCI | CCI | CCI Substance | CCI | CCI |
| | HPMC | MIN-117 | MIN-117 Dose | MIN-117 | Morphine |
| | 0.5% | 1 mg/kg | 3 mg/kg | 10 mg/kg | 3 mg/kg |
| | | | Route of administration | | |
| | IP | IP | IP | IP | SC |
| Nociceptive threshold (g) | 166 ± 6.7 | 184 ± 6.5 | 222 ± 9.2 | 280 ± 20.9 | — ± — |
| % variation vs pre-drug threshold | −7% | 10% | 35% | 71% | — |
| % variation vs vehicle-treated group | — | 11% | 34% | 69% | — |
| % variation vs control paw | −54% | −47% | −40% | −33% | — |
| % activity | — | 9% | 29% | 59% | — |
| Statistical analysis | — | NS | * | * | — |

Injured paw T0 + 120 min

TABLE 4

| | | | Baseline | | 30 | | 120 | |
|---|---|---|---|---|---|---|---|---|
| Substances | Rat | Weight (g) | control paw | injured paw | control paw | injured paw | control paw | injured paw |
| CCI | 9 | 274 | 300 | 160 | | | 420 | 140 |
| HPMC | 11 | 274 | 360 | 200 | | | 340 | 160 |
| 0.50% | 17 | 279 | 360 | 220 | | | 380 | 180 |
| IP | 21 | 289 | 340 | 180 | | | 380 | 180 |
| n = 10 | 51 | 310 | 300 | 160 | | | 300 | 140 |
| | 26 | 298 | 360 | 180 | | | 340 | 200 |
| | 35 | 282 | 360 | 180 | | | 400 | 180 |
| | 39 | 286 | 360 | 180 | | | 320 | 180 |
| | 42 | 270 | 420 | 160 | | | 400 | 160 |
| | 49 | 287 | 340 | 160 | | | 320 | 140 |
| Mean | | 284.9 | 350 | 178 | | | 360 | 166 |
| S.E.M | | 3.8 | 10.9 | 6.3 | | | 13.0 | 6.7 |
| n | | | 10.0 | 10.0 | | | 10.0 | 10.0 |
| % variation vs pre-drug threshold | | | — | — | | | — | −7% |
| % variation vs control paw | | | — | −49% | | | — | −54% |
| CCI | 2 | 301 | 420 | 120 | | | 400 | 200 |
| MIN-117 | 10 | 283 | 320 | 160 | | | 300 | 180 |
| 1 mg/kg | 18 | 268 | 400 | 140 | | | 400 | 160 |
| IP | 25 | 322 | 340 | 180 | | | 360 | 180 |
| n = 10 | 52 | 302 | 320 | 160 | | | 320 | 160 |
| | 30 | 281 | 380 | 160 | | | 440 | 160 |
| | 37 | 270 | 400 | 180 | | | 320 | 200 |
| | 41 | 290 | 440 | 180 | | | 300 | 200 |
| | 47 | 273 | 280 | 200 | | | 320 | 220 |
| | 57 | 273 | 360 | 200 | | | 320 | 180 |
| Mean | | 286 | 366 | 168 | | | 348 | 184 |
| S.E.M | | 5.5 | 16.1 | 8.0 | | | 15.5 | 6.5 |
| n | | | 10.0 | 10.0 | | | 10.0 | 10.0 |
| % variation vs pre-drug threshold | | | — | — | | | — | 10% |
| % variation vs vehicle treated group | | | — | −6% | | | — | 11% |
| % variation vs control paw | | | — | −54% | | | — | −47% |
| % activity | | | — | — | | | — | 9% |
| CCI | 1 | 290 | 340 | 160 | | | 440 | 280 |
| MIN-117 | 6 | 248 | 360 | 160 | | | 420 | 220 |
| 3 mg/kg | 12 | 296 | 360 | 180 | | | 420 | 200 |
| IP | 16 | 285 | 340 | 140 | | | 300 | 200 |
| n = 10 | 54 | 280 | 360 | 160 | | | 360 | 220 |
| | 29 | 315 | 380 | 200 | | | 340 | 180 |
| | 31 | 282 | 340 | 180 | | | 360 | 240 |
| | 36 | 303 | 340 | 140 | | | 460 | 240 |
| | 43 | 305 | 440 | 160 | | | 280 | 240 |
| | 48 | 258 | 380 | 160 | | | 340 | 200 |
| Mean | | 286.3 | 364 | 164 | | | 372 | 222 |
| S.E.M | | 6.6 | 9.8 | 5.8 | | | 19.1 | 9.2 |
| n | | | 10.0 | 10.0 | | | 10.0 | 10.0 |
| % variation vs pre-drug threshold | | | — | — | | | — | 35% |
| % variation vs vehicle treated group | | | — | −8% | | | — | 34% |
| % variation vs control paw | | | — | −55% | | | — | −40% |
| % activity | | | — | — | | | — | 29% |

TABLE 4-continued

| | | | Baseline | | 30 | | 120 | |
|---|---|---|---|---|---|---|---|---|
| Substances | Rat | Weight (g) | control paw | injured paw | control paw | injured paw | control paw | injured paw |
| CCI | 5 | 288 | 440 | 180 | | | 600 | 440 |
| MIN-117 | 7 | 271 | 300 | 160 | | | 320 | 320 |
| 10 mg/kg | 15 | 264 | 440 | 160 | | | 440 | 260 |
| IP | 20 | 262 | 320 | 140 | | | 400 | 220 |
| n = 10 | 53 | 295 | 320 | 120 | | | 280 | 240 |
| | 27 | 281 | 420 | 200 | | | 440 | 240 |
| | 33 | 264 | 360 | 180 | | | 480 | 320 |
| | 44 | 270 | 360 | 160 | | | 440 | 280 |
| | 50 | 266 | 320 | 160 | | | 360 | 240 |
| | 58 | 285 | 400 | 180 | | | 440 | 240 |
| Mean | | 274.6 | 368 | 164 | | | 420 | 280 |
| S.E.M | | 3.7 | 16.9 | 7.2 | | | 28.1 | 20.9 |
| n | | | 10.0 | 10.0 | | | 10.0 | 10.0 |
| % variation vs pre-drug threshold | | | — | — | | | — | 71% |
| % variation vs vehicle treated group | | | — | −8% | | | — | 69% |
| % variation vs control paw | | | — | −55% | | | — | −33% |
| % activity | | | — | — | | | — | 59% |
| CCI | 3 | 293 | 440 | 220 | 680 | 680 | | |
| Morphine | 8 | 292 | 400 | 180 | 640 | 600 | | |
| 3 mg/kg | 14 | 305 | 400 | 180 | 600 | 480 | | |
| IP | 19 | 285 | 300 | 180 | 640 | 560 | | |
| n = 10 | 24 | 292 | 300 | 140 | 640 | 320 | | |
| | 28 | 273 | 360 | 200 | 680 | 500 | | |
| | 34 | 300 | 460 | 180 | 600 | 240 | | |
| | 38 | 288 | 440 | 240 | 560 | 400 | | |
| | 45 | 271 | 340 | 220 | 660 | 600 | | |
| | 59 | 266 | 280 | 140 | 600 | 480 | | |
| Mean | | 286.5 | 372 | 188 | 630 | 486 | | |
| S.E.M | | 4.0 | 20.7 | 10.4 | 12.4 | 42.8 | | |
| n | | | 10.0 | 10.0 | 10.0 | 10.0 | | |
| % variation vs pre-drug threshold | | | — | — | — | 159% | | |
| % variation vs vehicle treated group | | | — | 6% | — | — | | |
| % variation vs control paw | | | — | −49% | — | −23% | | |
| % activity | | | — | — | — | 165% | | |

Example 4

Assessment of the Antihyperalgesic Effect of a Single Intraperitoneal Administration of MIN-117 in a Model of Carrageenan-Induced Mechanical Hyperalgesia in Rats The antihyperalgesic effect of a single intraperitoneal administration of MIN-117 in a model of carrageenan-induced mechanical hyperalgesia in rats was assessed.

In this model, inflammation is induced by intraplantar injection of carrageenan (2%) into the right hindpaw of the rat. Three hours later, reaction thresholds are measured using the paw pressure test. Pressure is gradually applied to both hind paws (inflamed and control) of the rat, and reaction thresholds are determined as the pressure (g) required to elicit paw withdrawal or vocalization. Morphine (3 mg/kg, s.c.), used as positive control.

This assay is widely and reliably used for revealing the efficacy of new analgesics in a model of inflammatory pain in conscious rats.

The experiments in this study used fifty (50) male Sprague-Dawley rats (SPF status, Janvier, France), each weighing 183-244 g during the experimental phase. The rats were housed in a temperature (20-24° C.) and relative humidity (45%-65%) controlled room and acclimated to an artificial day/night cycle of 12 hours light (6.30 a.m. to 6.30 p.m.)/12 hours darkness. Rats had free access to sterilized tap water and were fed ad libitum with pelleted complete diet (reference A04, S.A.F.E.). Animals were housed 4 per cage (cages Type E) and were acclimated for a period of at least 5 days before any testing. Each rat was identified by tail markings. Based on the SPF status of the animal facilities, there is no reason to expect that contaminants were present in the food, water or bedding, at levels capable of interfering with the results of the tests.

MIN-117 was supplied by Minerva Neuroscience, Inc. as a white to pale yellowish power or crystalline powder and was stored at room temperature prior to use.

Morphine was supplied by Francopia (Catalog reference no. 3695, batch no. HR00002) and was stored at room temperature prior to use.

Vehicles (HPMC, water, saline) were stored at 4° C. 0.5% (w/v) hydroxypropylmethylcellulose (HPMC) 80-120 centipoises in water for injection was used as vehicle for MIN-117. 0.9% NaCl was used as vehicle for morphine.

Carrageenan was supplied by Sigma-Aldrich (Catalog reference no. C1013, batch no. SLBD1934V) and was stored in suspension at 4° C. 0.9 NaCl (w/v) was used vehicle for 2% carrageenan suspension.

Ugo Basile Analgesimeter (Ugo Basile, Italy) was used for the paw pressure test.

SigmaStat software version 3.5 (SPSS Science Software, Erkrath, Germany) and Lab X direct software version 2.4 (Mettler Toledo, France) were used for data processing.

Static mechanical hyperalgesia was assessed using the Paw Pressure test or Randall & Selitto test (Randall, L. O. and Selitto, J. J., A method for measurement of analgesic activity on inflamed tissue, *Arch Int Pharmacodyn*, 1957 (111): 409-419). This test requires the application of an increasing pressure on the hind paws between a flat surface and a blunt pointer. This test is usually used with animals with one hind paw inflamed by an injection or injured by ligation, and one normal hind paw, to evaluate drugs for analgesic action. The apparatus exerts a steadily increasing force and reaction threshold is determined as the pressure (g) required to elicit paw withdrawal and/or vocalization. In the experiment, animals were gently handled by the experimenter and static mechanical hyperalgesia was assessed. Each reaction threshold measurement was done for both hind paws.

Five (5) experimental groups of 10 rats each were used. Each group was first injected with 100 μL of a 2% carrageenan suspension was injected into the plantar aspect of the right hindpaw. Three hours after carrageenan injection, nociceptive reaction thresholds (vocalization or paw withdrawal) were measured in order to select animals meeting the inclusion criteria: 20 g<paw withdrawal threshold<240 g (baseline). The 5 groups were then administered the following:
  Group 1: vehicle (0.5% HPMC), i.p., solution (negative control);
  Group 2: MIN-117 (1 mg/kg, i.p.) in 0.5% HPMC, suspension;
  Group 3: MIN-117 (3 mg/kg, i.p.) in 0.5% HPMC, suspension;
  Group 4: MIN-117 (10 mg/kg, i.p.) in 0.5% HPMC, suspension; and
  Group 5: morphine (3 mg/kg, s.c.) in 0.9% NaCl, solution (positive control).

Thirty minutes after morphine injection, the antihyperalgesic effect of morphine was evaluated using the paw pressure test. For vehicle and MIN-117 administration, the antihyperalgesic effect was evaluated after 120 min. using the paw pressure test.

Vehicle and MIN-117 were intraperitoneally administered at 10 mL/kg. Morphine was subcutaneously administered at 5 mL/kg. Dosing and testing were performed in a random order by a blinded experimenter except for the morphine-treated group. Doses were expressed in terms of free active substance.

Rats were sacrificed at the end of the experiment by $CO_2$ inhalation pending subsequent removal by a certified company.

Results were expressed as:
  The paw withdrawal threshold (mean±s.e.m.) in grams of contact pressure for each group, calculated from individual paw withdrawal thresholds
  The percentage of variation of the paw withdrawal threshold calculated from the mean value of the vehicle-treated group The percentage of activity of activity of the compound on carrageenan-induced mechanical hyperalgesia, calculated as follows:

$$\frac{\text{(Nociceptive threshold injured paw)}_{treated} - \text{(Nociceptive threshold injured paw)}_{vehicle}}{\text{(Nociceptive threshold control paw)}_{vehicle} - \text{(Nociceptive threshold injured paw)}_{vehicle}}.$$

To determine a statistical effect of the test substance and the reference substance, data were analyzed by a non-parametrical test. The significance level was p<0.05.

Figure 4:
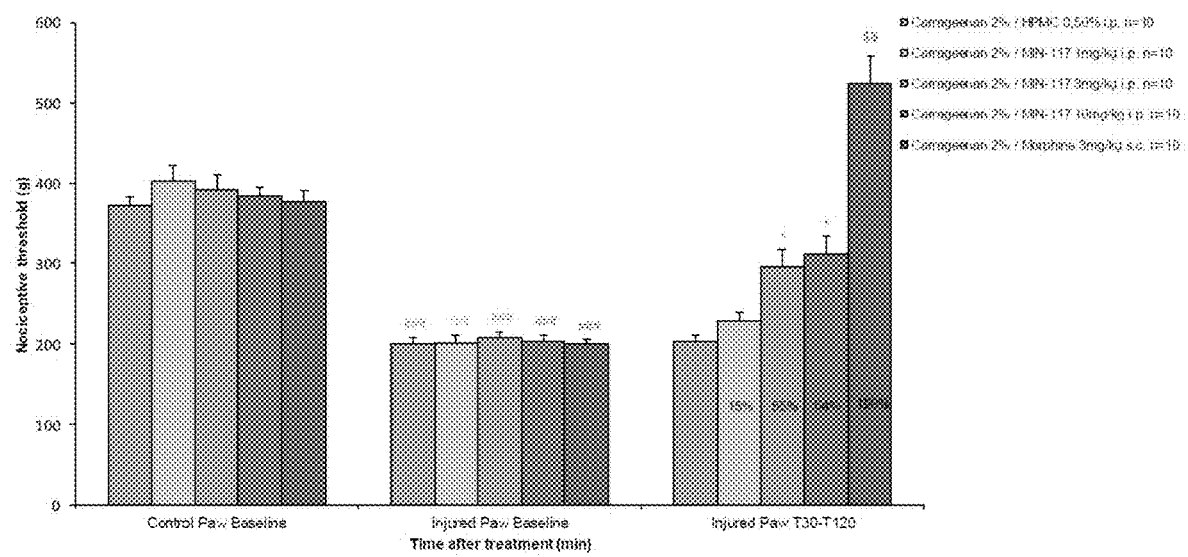
FIG. 4 is a series of bar graphs showing the effect of a single intraperitoneal administration of MIN-117 at various doses, morphine, and vehicle in a model of carrageenan-induced mechanical hyperalgesia in rats. Nociceptive threshold was measured 120 min. after vehicle or MIN-117 administration and 30 min. after morphine injection. Results are expressed as mean±s.e.m. Percentage are expressed as percentage of activity. ###: $p<0.001$ as compared to the control paw of the corresponding group, Mann-Whitney Rank sum test. *: $p<0.05$ as compared to the vehicle-treated group, Kruskal-Wallis one-way ANOVA on ranks. $$: $p<0.01$ as compared to the baseline of the corresponding group, Wilcoxon rank sum test. Results are expressed as mean±s.e.m. Percentage of variation are expressed as increase (+) or decrease (−) as compared to the pre-drug threshold, to the vehicle-treated group, to the control paw or as percentage of activity. ###: $p<0.001$ as compared to the control paw of the corresponding group, Mann-Whitney Rank sum test. *: $p<0.05$ as compared to the vehicle-treated group, Kruskal-Wallis one-way ANOVA on ranks. $$: $p<0.01$ as compared to the baseline of the corresponding group, Wilcoxon rank sum test. NS: Not significant.

As summarized in Table 5 and FIG. 4, the raw data in Table 6 show that before dosing, all the groups exhibited a significantly reduced nociceptive threshold for the injured paw ranged from 46% to 50% (p<0.001) as compared to the control paw, 3 h after injection of a 2% carrageenan suspension. Rats from the vehicle-treated group (0.5% HPMC, left-most columns in FIG. 4) exhibited, for the injured paw, a stable nociceptive threshold 120 min. after treatment (204±6.5 g vs. 200±7.3 g at $T_0$). Subcutaneously administered at 3 mg/kg (right-most columns in FIG. 4), morphine induced a marked and significant increase in the nociceptive threshold 30 min. after the injection with a percentage of activity of +190% (524±35.6 g vs 200±6.7 g, p<0.01, as compared to the baseline pre-treatment).

Intraperitoneal administration of MIN-117 at 1 mg/kg (second columns from left in FIG. 4) did not induce any significant increase in the nociceptive threshold, 120 min. after treatment, as compared to the vehicle-treated group (percentage of activity: +15%). When administered at 3 and 10 mg/kg (middle columns and second columns from right in FIG. 4, respectively), however, MIN-117 induced, 120 min. later, a significant increase in the nociceptive thresholds as compared to the vehicle-treated group (respectively 296±20.8 g and 312±22.7 g vs 204±6.5 g) with a percentage of activity of +55% and +64% respectively (p<0.05). Results are expressed as mean±s.e.m. Percentage are expressed as percentage of activity. ###: p<0.001 as compared to the control paw of the corresponding group, Mann-Whitney Rank sum test. *: p<0.05 as compared to the vehicle-treated group, Kruskal-Wallis one-way ANOVA on ranks. $$: p<0.01 as compared to the baseline of the corresponding group, Wilcoxon rank sum test.

TABLE 5

| | Control paw T0 | | | | |
|---|---|---|---|---|---|
| | Reagent | | | | |
| | Carrageenan 2%/ | Carrageenan 2%/ | Carrageenan 2%/ | Carrageenan 2%/ | Carrageenan 2%/ |
| | | | Substance | | |
| | HPMC | MIN-117 | MIN-117 | MIN-117 | Morphine |
| | | | Dose | | |
| | 0.5% | 1 mg/kg | 3 mg/kg | 10 mg/kg | 3 mg/kg |
| | | | Route of administration | | |
| | i.p. | i.p. | i.p. | i.p. | s.c. |
| Nociceptive threshold (g) | 372 ± 11.2 | 402 ± 19.9 | 392 ± 18.4 | 384 ± 10.2 | 376 ± 14.5 |
| n | 10 | 10 | 10 | 10 | 10 |

TABLE 5-continued

| | Injured paw | | | | |
|---|---|---|---|---|---|
| | Reagent | | | | |
| | Carrageenan 2%/ | Carrageenan 2%/ | Carrageenan 2%/ Substance | Carrageenan 2%/ | Carrageenan 2%/ |
| | HPMC | MIN-117 | MIN-117 Dose | MIN-117 | Morphine |
| | 0.5% | 1 mg/kg | 3 mg/kg Route of administration | 10 mg/kg | 3 mg/kg |
| | i.p. | i.p. | i.p. | i.p. | s.c. |
| Nociceptive threshold (g) | 200 ± 7.3 | 202 ± 8.7 | 208 ± 7.4 | 204 ± 6.5 | 200 ± 6.7 |
| % variation vs vehicle-treated group | — | 1% | 4% | 2% | 0% |
| % variation vs control paw | −46% | −50% | −47% | −47% | −47% |
| Statistical analysis | ### | ### | ### | ### | ### |

| | Injured paw T0 + 30 min | | | | |
|---|---|---|---|---|---|
| | Reagent | | | | |
| | Carrageenan 2%/ | Carrageenan 2%/ | Carrageenan 2%/ Substance | Carrageenan 2%/ | Carrageenan 2%/ |
| | HPMC | MIN-117 | MIN-117 Dose | MIN-117 | Morphine |
| | 0.5% | 1 mg/kg | 3 mg/kg Route of administration | 10 mg/kg | 3 mg/kg |
| | i.p. | i.p. | i.p. | i.p. | s.c. |
| Nociceptive threshold (g) | — | — | — | — | 524 ± 35.6 |
| % variation vs pre-drug threshold | — | — | — | — | 162% |
| % variation vs vehicle-treated group | — | — | — | — | — |
| % variation vs control paw | — | — | — | — | −17% |
| % activity | — | — | — | — | 190% |
| Statistical analysis | — | — | — | — | $$ |

| | Injured paw T0 + 120 min | | | | |
|---|---|---|---|---|---|
| | Reagent | | | | |
| | Carrageenan 2%/ | Carrageenan 2%/ | Carrageenan 2%/ Substance | Carrageenan 2%/ | Carrageenan 2%/ |
| | HPMC | MIN-117 | MIN-117 Dose | MIN-117 | Morphine |
| | 0.5% | 1 mg/kg | 3 mg/kg Route of administration | 10 mg/kg | 3 mg/kg |
| | i.p. | i.p. | i.p. | i.p. | s.c. |
| Nociceptive threshold (g) | 204 ± 6.4 | 230 ± 9.5 | 296 ± 20.8 | 312 ± 22.7 | — |
| % variation vs pre-drug threshold | 2% | 14% | 42% | 53% | — |
| % variation vs vehicle-treated group | — | 13% | 45% | 53% | — |
| % variation vs control paw | −45% | −39% | −23% | −27% | — |
| % activity | — | 15% | 55% | 64% | — |
| Statistical analysis | — | NS | * | * | — |

TABLE 6

| Substances | Rat | Weight (g) | Baseline control paw | Baseline injured paw | 30 control paw | 30 injured paw | 120 control paw | 120 injured paw |
|---|---|---|---|---|---|---|---|---|
| Carrageenan 2%/ | 4 | 204 | 340 | 180 | | | 360 | 200 |
| HPMC | 7 | 221 | 420 | 220 | | | 420 | 220 |
| 0.5% | 15 | 189 | 320 | 160 | | | 340 | 180 |
| i.p. | 20 | 195 | 380 | 200 | | | 360 | 180 |
| n = 10 | 21 | 202 | 340 | 220 | | | 380 | 220 |
| | 27 | 205 | 400 | 200 | | | 460 | 220 |
| | 33 | 233 | 420 | 240 | | | 320 | 200 |
| | 30 | 218 | 340 | 200 | | | 380 | 240 |
| | 43 | 202 | 380 | 180 | | | 380 | 200 |
| | 47 | 211 | 380 | 200 | | | 320 | 180 |
| Mean | | 208 | 372 | 200 | | | 372 | 204 |
| S.E.M | | 4.1 | 11.2 | 7.3 | | | 13.7 | 6.5 |
| n | | | 10.0 | 10.0 | | | 10.0 | 10.0 |
| % variation vs pre-drug threshold | | | — | — | | | — | 35% |
| % variation vs control paw | | | — | −46% | | | — | −45% |
| Carrageenan 2%/ | 3 | 217 | 440 | 240 | | | 400 | 260 |
| MIN-117 | 6 | 229 | 460 | 220 | | | 440 | 260 |
| 1 mg/kg | 12 | 214 | 360 | 220 | | | 340 | 220 |
| i.p. | 18 | 227 | 420 | 200 | | | 480 | 240 |
| n = 10 | 22 | 197 | 360 | 160 | | | 360 | 260 |
| | 28 | 196 | 460 | 220 | | | 380 | 260 |
| | 32 | 188 | 420 | 180 | | | 360 | 200 |
| | 37 | 197 | 300 | 160 | | | 320 | 200 |
| | 41 | 244 | 480 | 220 | | | 360 | 220 |
| | 46 | 209 | 320 | 200 | | | 360 | 180 |
| Mean | | 212 | 402 | 202 | | | 380 | 230 |
| S.E.M | | 5.6 | 19.9 | 8.7 | | | 15.2 | 9.5 |
| n | | | 10.0 | 10.0 | | | 10.0 | 10.0 |
| % variation vs pre-drug threshold | | | — | — | | | — | 14% |
| % variation vs vehicle treated group | | | — | 1% | | | — | 13% |
| % variation vs control paw | | | — | −50% | | | — | −39% |
| % activity | | | — | — | | | — | 15% |
| Carrageenan 2%/ | 2 | 215 | 400 | 240 | | | 380 | 360 |
| MIN-117 | 10 | 219 | 400 | 200 | | | 360 | 220 |
| 3 mg/kg | 14 | 183 | 440 | 220 | | | 360 | 420 |
| i.p. | 16 | 188 | 320 | 180 | | | 360 | 280 |
| n = 10 | 24 | 199 | 400 | 200 | | | 440 | 340 |
| | 29 | 215 | 380 | 220 | | | 500 | 280 |
| | 36 | 207 | 320 | 180 | | | 320 | 280 |
| | 49 | 217 | 320 | 180 | | | 360 | 320 |
| | 55 | 217 | 480 | 220 | | | 360 | 260 |
| | 56 | 210 | 460 | 240 | | | 420 | 200 |
| Mean | | 207 | 392 | 208 | | | 368 | 296 |
| S.E.M | | 4.1 | 18.4 | 7.4 | | | 16.6 | 20.8 |
| n | | | 10.0 | 10.0 | | | 10.0 | 10.0 |
| % variation vs pre-drug threshold | | | — | — | | | — | 42% |
| % variation vs vehicle treated group | | | — | 4% | | | — | 45% |
| % variation vs control paw | | | — | −47% | | | — | −23% |
| % activity | | | — | — | | | — | 55% |
| Carrageenan 2%/ | 5 | 217 | 400 | 240 | | | 440 | 320 |
| MIN-117 | 9 | 205 | 420 | 200 | | | 440 | 280 |
| 10 mg/kg | 17 | 206 | 360 | 180 | | | 480 | 340 |
| i.p. | 26 | 209 | 420 | 200 | | | 440 | 360 |
| n = 10 | 34 | 207 | 400 | 220 | | | 520 | 480 |
| | 40 | 217 | 320 | 220 | | | 400 | 260 |
| | 45 | 200 | 360 | 180 | | | 340 | 240 |
| | 50 | 193 | 360 | 180 | | | 320 | 280 |
| | 51 | 205 | 400 | 220 | | | 360 | 240 |
| | 54 | 206 | 400 | 200 | | | 540 | 320 |
| Mean | | 207 | 384 | 204 | | | 428 | 312 |
| S.E.M | | 2.3 | 10.2 | 6.5 | | | 23.3 | 22.7 |
| n | | | 10.0 | 10.0 | | | 10.0 | 10.0 |
| % variation vs pre-drug threshold | | | — | — | | | — | 53% |
| % variation vs vehicle treated group | | | — | 2% | | | — | 53% |
| % variation vs control paw | | | — | −47% | | | — | −27% |
| % activity | | | — | — | | | — | 64% |
| Carrageenan 2%/ | 1 | 222 | 440 | 220 | 680 | 680 | | |
| Morphine | 8 | 206 | 360 | 180 | 680 | 600 | | |
| 3 mg/kg | 19 | 225 | 340 | 200 | 640 | 500 | | |
| s.c. | 25 | 197 | 440 | 200 | 680 | 640 | | |
| n = 10 | 30 | 208 | 320 | 160 | 640 | 320 | | |
| | 35 | 223 | 360 | 180 | 600 | 400 | | |
| | 38 | 236 | 360 | 220 | 620 | 600 | | |

TABLE 6-continued

| Substances | Rat | Weight (g) | Baseline control paw | Baseline injured paw | 30 control paw | 30 injured paw | 120 control paw | 120 injured paw |
|---|---|---|---|---|---|---|---|---|
| | 44 | 206 | 360 | 220 | 560 | 540 | | |
| | 53 | 188 | 440 | 220 | 680 | 440 | | |
| | 57 | 212 | 340 | 200 | 520 | 520 | | |
| Mean | | 212 | 376 | 200 | 630 | 524 | | |
| S.E.M | | 4.5 | 14.5 | 6.7 | 17.7 | 35.6 | | |
| n | | | 10.0 | 10.0 | 10.0 | 10.0 | | |
| % variation vs pre-drug threshold | | | — | — | — | 162% | | |
| % variation vs vehicle treated group | | | — | 0% | — | — | | |
| % variation vs control paw | | | — | −47% | — | −17% | | |
| % activity | | | — | — | — | 190% | | |

Example 5

Evaluation of the Analgesic Efficacy of MIN-117 for Neuropathic Pain Following MIN-117 Intraperitoneal Administration in Sprague Dawley Rat Model of Chemotherapy-Induced Peripheral Neuropathic Pain Assessment of neuropathic pain using von Frey filaments was performed. Rats were administered paclitaxel (2 mg/kg) on four alternate days (days 1, 3, 5 and 7). Baseline and post treatment paw withdrawal thresholds (PWT) were evaluated using von Frey filaments (Semmes-Weinstein filaments, Stoelting, Wood Dale, Ill., USA) of varying stiffness (0.4, 0.7, 1.2, 2.0, 3.6, 5.5, 8.5, 10, 15, 26 g). Animals were placed on a perforated metallic platform and allowed to acclimate to their surroundings for a minimum of 15 minutes before each test session. Each filament was presented perpendicular to the plantar surface with sufficient force to cause slight buckling against the paw, and then held until a positive response is noted (paw sharply withdrawn). As described by Chaplan, S. R. et al. "Qualitative Assessment of Tactile Allodynia in the Rat Paw" Journal of Neuroscience Methods, 53 (1994), 55-63 ("Chaplan"), once the threshold was crossed, the 2 responses straddling the threshold are retrospectively designated as the first 2 responses. Four additional responses were measured to stimuli varied sequentially up or down based on the animal's response. The 6 responses in the immediate vicinity of the threshold were used to calculate the 50% g threshold:

$$50\% \text{ g threshold} = (10^{[Xf+k*d]})/10000$$

Xf is the final filament used (in log units). The parameter k is from the Appendix 1 in Chaplan and was determined by the pattern of the von Frey responses (e.g. OXOXOX where 'O' indicates no response and 'X' denotes a withdrawal). The parameter d is the difference between stimuli which Chaplan used a constant d=0.224. To accommodate for the use of the 10 g and 26 g filaments, the exact difference between stimuli were used.

Figure 5:
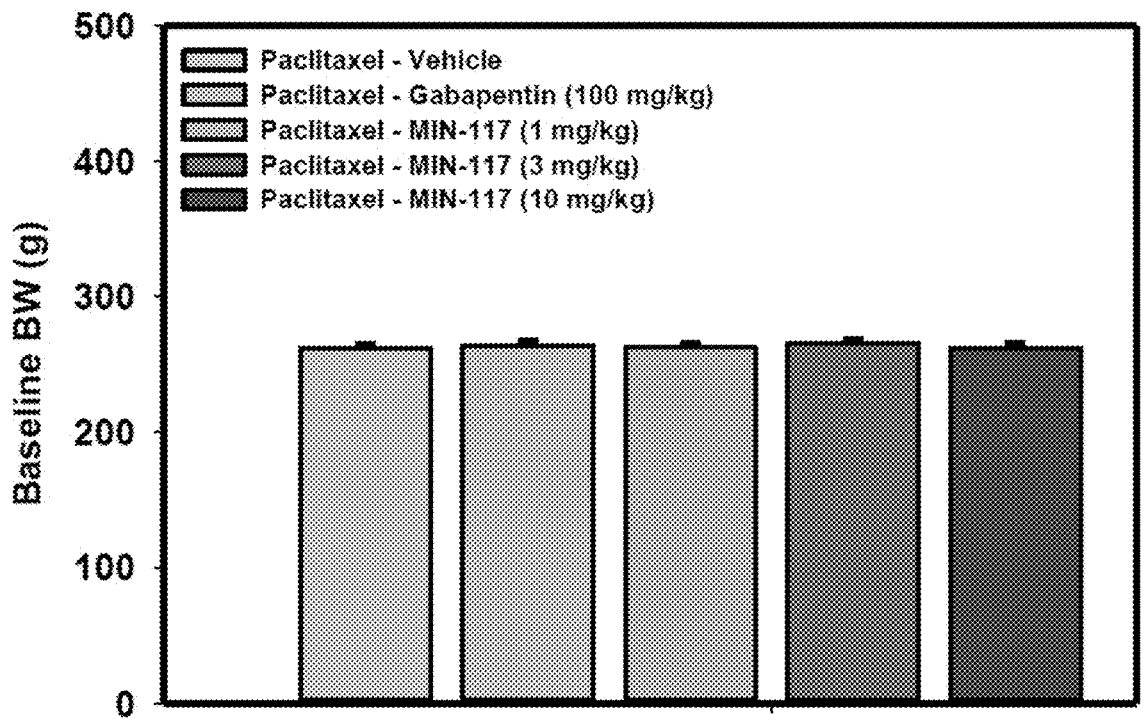
FIG. 5 is series of bar graphs that represent baseline body weight of rats prior to paclitaxel injections in the chemotherapy induced neuropathic pain study. (Data are presented as mean±s.e.m.) Repeated measures ANOVA found no significant difference between groups.

Male Sprague Dawley rats (from Envigo, Ind., USA) were used in the study. Animals were received at approximately 250 g and housed 3 per cage upon arrival. All rats were examined, handled, and weighed prior to initiation of the study to assure adequate health and suitability. During the course of the study, 12 h/12 h light/dark cycles was maintained. The room temperature was be maintained between 20 and 23° C. with a relative humidity maintained around 50%. Chow and water was provided ad libitum for the duration of the study. All testing was performed during the animal's light cycle phase. Every effort was made to minimize suffering of animals. Rats with baseline PWT less than 12 g were not included in the study. Rats were balanced by body weight and by their pre-paclitaxel PWT values. The baseline body weight (BW) of all rats prior to paclitaxel injections are shown in FIG. 5. ANOVA found no significant differences between the treatment groups.

Paclitaxel was purchased from Biolyse Pharma (Ontario, Canada) and was injected i.p. (2 mg/kg) on four alternate days (day 1, 3, 5 and 7) for a total of 4 injections at a dose volume of 1 mL/kg.

On day 14, baseline VF responses were measured to ensure all rats showed a stable neuropathic pain response. Rats were subsequently balanced and assigned to treatment groups based on post-paclitaxel PWT values. On test day, PWT was assessed two hours post vehicle or MIN-117 injections and one hour after gabapentin administration.

Figure 6:
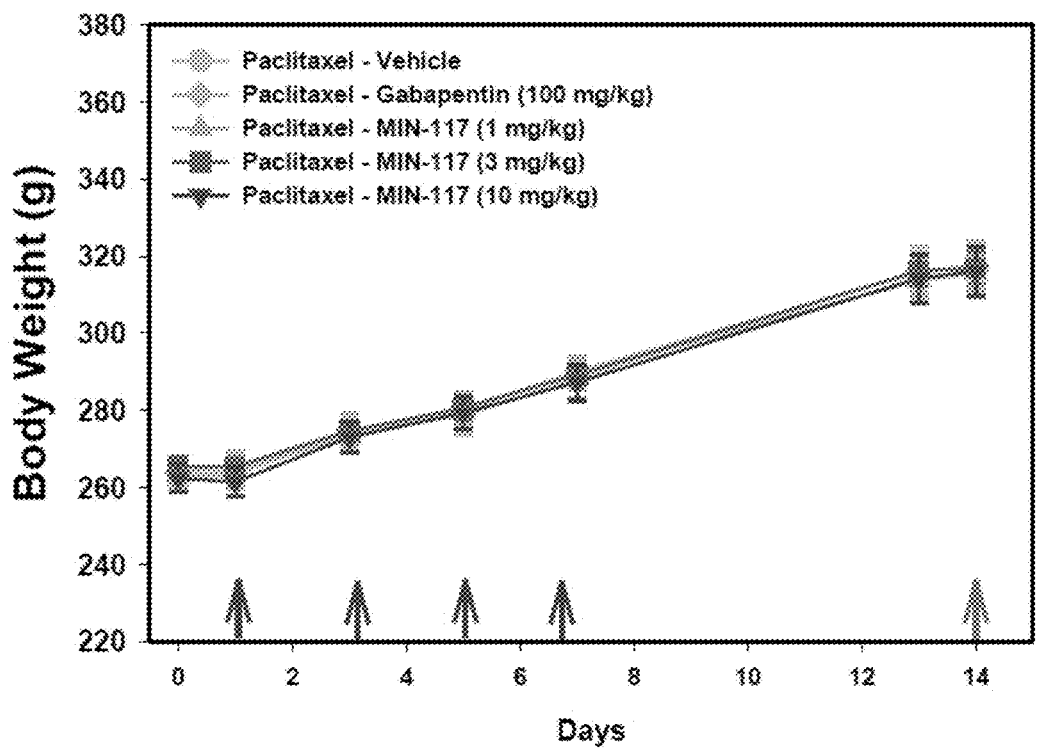
FIG. 6 is series of line graphs that represent the body weight of the rats during the chemotherapy induced neuropathic pain study described in Example 5. Arrows at days 1, 3, 5 and 7 indicate days of paclitaxel injections and the arrow at day 14 indicates the day of MIN-117 or gabapentin (positive control) administration. (Data are presented as mean±s.e.m.) Repeated measures ANOVA found no significant difference between groups.

The body weight of all rats during paclitaxel treatment and MIN-117 administration are shown in FIG. 6. Repeated measures ANOVA found no significant difference between groups.

Figure 7:
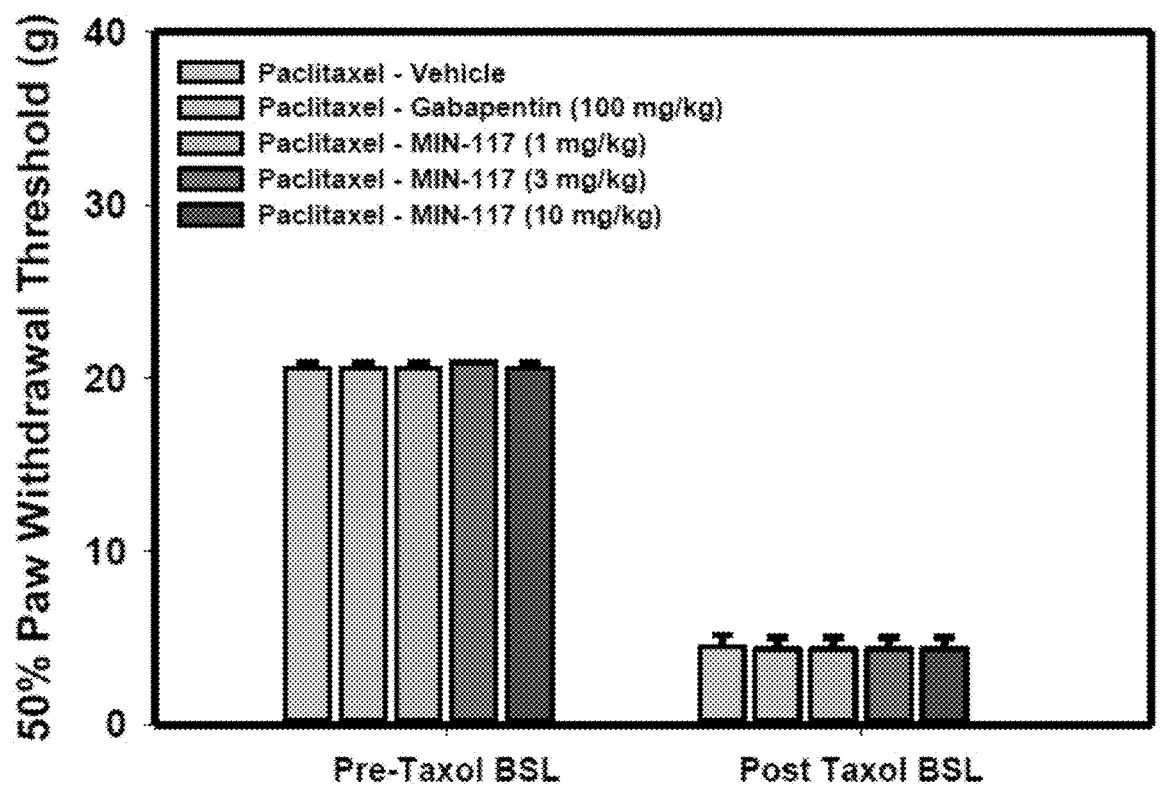
FIG. 7 is a series of bar graphs showing the effect of baseline paw withdrawal threshold before and after paclitaxel injections between the various treatment groups (vehicle, gabapentin, and various doses of MIN-117). (Data are presented as mean±s.e.m.) ANOVA found no significant differences between the treatment groups prior to treatment.

Baseline Paw Withdrawal Threshold (PWT) prior to and after paclitaxel injections are shown in FIG. 7. ANOVA found no significant differences between the treatment groups prior to treatment.

Figure 8:
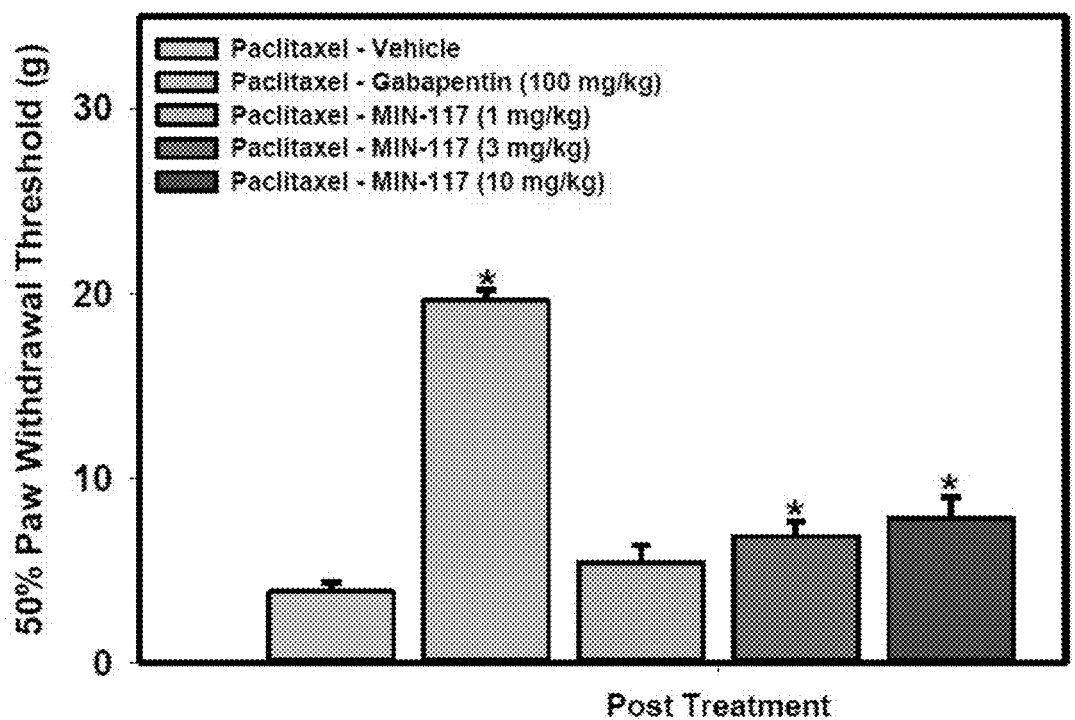
FIG. 8 is a series of bar graphs showing the effect of gabapentin, various doses of MIN-117, and vehicle on paw withdrawal thresholds at day 14 since the first paclitaxel treatment. (Data are presented as mean±s.e.m.) *$p<0.05$ compared to vehicle.

The effects of Gabapentin or MIN-117 on PWT at Day 14 are shown in FIG. 8. Gabapentin was purchased from Toronto Research Chemicals and was dissolved in saline and administered orally 60 minutes prior to test at a dose volume of 1 mL/kg. MIN-117 (1, 3 and 10 mg/kg), formulated in 0.5% (w/v) hydroxypropylmethylcellulose (HPMC, Sigma-Aldrich), was administered i.p. at a dose volume of 1 mL/kg. MIN-117 was administered 2 hours prior to test.

One-way ANOVA indicated significant differences between groups. Gabapentin (second column from left in FIG. 8) showed a significant increase in PWT compared to the vehicle (left-most column in FIG. 8). Animals treated with MIN-117 at a dose of 3 mg/kg (second column from right in FIG. 8) and with MIN-117 at a dose of 10 mg/kg (right-most column in FIG. 8) also showed a significant increase in PWT compared to vehicle. Animals treated with MIN-117 at a dose of 1 mg/kg (middle column in FIG. 8) did not show a significant increase in PWT compared to vehicle. Raw data for these experiments are included below in Table 7.

TABLE 7

ANOVA Table for Day 14 Avg.

|  | DF | Sum of Squares | Mean Square | F-Value | P-Value | Lambda | Power |
|---|---|---|---|---|---|---|---|
| Treatment | 4 | 1891.683 | 472.921 | 58.467 | <.0001 | 233.867 | 1.000 |
| Residual | 55 | 444.880 | 8.089 |  |  |  |  |

Means Table for Day 14 Avg.
Effect: Treatment

|  | Count | Mean | Std. Dev. | Std. Err. |
|---|---|---|---|---|
| Paclitaxel + Vehicle | 12 | 3.874 | 1.745 | .504 |
| Paclitaxel + Gabapentin (100 mg/kg) | 12 | 19.633 | 1.861 | .537 |
| Paclitaxel + MIN-117 (1 mg/kg) | 12 | 5.433 | 3.257 | .940 |
| Paclitaxel + MIN-117 (3 mg/kg) | 12 | 6.858 | 2.775 | .801 |
| Paclitaxel + MIN-117 (10 mg/kg) | 12 | 7.832 | 3.953 | 1.141 |

Fisher's PLSD for Day 14 Avg.
Effect: Treatment
Significance Level: 5%

|  | Mean Diff. | Crit. Diff. | P-Value |
|---|---|---|---|
| Paclitaxel + Vehicle, Paclitaxel + Gabapentin (100 mg/kg) | −15.759 | 2.327 | <.0001 |
| Paclitaxel + Vehicle, Paclitaxel + MIN-117 (1 mg/kg) | −1.558 | 2.327 | .1850 |
| Paclitaxel + Vehicle, Paclitaxel + MIN-117 (3 mg/kg) | −2.984 | 2.327 | .0129 |
| Paclitaxel + Vehicle, Paclitaxel + MIN-117 (10 mg/kg) | −3.957 | 2.327 | .0012 |
| Paclitaxel + Gabapentin (100 mg/kg), Paclitaxel + MIN-117 (1 mg/kg) | 14.200 | 2.327 | <.0001 |
| Paclitaxel + Gabapentin (100 mg/kg), Paclitaxel + MIN-117 (3 mg/kg) | 12.775 | 2.327 | <.0001 |
| Paclitaxel + Gabapentin (100 mg/kg), Paclitaxel + MIN-117 (10 mg/kg) | 11.802 | 2.327 | <.0001 |
| Paclitaxel + MIN-117 (1 mg/kg), Paclitaxel + MIN-117 (3 mg/kg) | −1.425 | 2.327 | .2249 |
| Paclitaxel + MIN-117 (1 mg/kg), Paclitaxel + MIN-117 (10 mg/kg) | −2.399 | 2.327 | .0436 |
| Paclitaxel + MIN-117 (3 mg/kg), Paclitaxel + MIN-117 (10 mg/kg) | −973 | 2.327 | .4055 |

Treatment with MIN-117 (3 and 10 mg/kg) significantly reduced neuropathic pain as indicated by a significantly increased PWT compared to the paclitaxel-vehicle group.

Example 6

Evaluation of the Analgesic Efficacy of MIN-117 Following Chronic Administration in a Rat Model of Chemotherapy-Induced Peripheral Neuropathic Pain The objective of this study was to assess the analgesic efficacy of MIN-117 in a rat model of chemotherapy-induced peripheral neuropathic pain following chronic injection.

Male Sprague Dawley rats from Envigo were used in the study. Animals were received at approximately 250 g and housed 3 per cage upon arrival. All rats were examined, handled, and weighed prior to initiation of the study to assure adequate health and suitability. During the course of the study, 12/12 light/dark cycles was maintained. The room temperature was be maintained between 20 and 23° C. with a relative humidity maintained around 50%. Chow and water was provided ad libitum for the duration of the study. All testing was performed during the animal's light cycle phase.

Reference Formulations:

Paclitaxel (2 mg/kg) was purchased from Biolyse Pharma and injected i.p. on four alternate days (day 1, 3, 5 and 7) for a total of 4 injections at a dose volume of 1 mL/kg.

Gabapentin (100 mg/kg) was dissolved in saline and administered orally at a dose volume of 1 mL/kg. For prevention study, gabapentin was administered on day 14, sixty minutes prior to test. For reversal study, gabapentin was administered once daily for 2 weeks. On test days it was administered 60 minutes prior to test.

Sponsor Test Article

Prevention study: MIN-117 (10 mg/kg) was formulated in 0.5% (w/v) hydroxypropylmethyl cellulose (HPMC) 8°-120 centipoises in water and was administered i.p once daily for 7 or 14 days at a dose volume of 1 mL/kg. On test days, MIN-117 was administered 2 hours prior to test.

Reversal study: MIN-117 (1, 3 and 10 mg/kg) was formulated in 0.5% (w/v) hydroxypropylmethyl cellulose (HPMC) 8°-120 centipoises in water and administered i.p once daily for 2 weeks at a dose volume of 1 mL/kg. On test days, MIN-117 was administered 2 hours prior to test.

Behavioral Testing

Body weight (BW) was measured daily during treatment and twice a week after cessation of dosing.

Paw Withdrawal Threshold Using Von Frey Filaments

Rats were administered paclitaxel (2 mg/kg) on four alternate days (days 1, 3, 5 and 7). Baseline and post treatment Paw Withdrawal Threshold (PWT) were evaluated using von Frey filaments (Semmes-Weinstein filaments, Stoelting, Wood Dale, Ill., USA) of varying stiffness (0.4, 0.7, 1.2, 2.0, 3.6, 5.5, 8.5, 10, 15, 26 g). Animals were placed on a perforated metallic platform and allowed to acclimate to their surroundings for a minimum of 15 minutes before each test session. Each filament was presented perpendicular to the plantar surface with sufficient force to cause slight buckling against the paw, and then held until a positive response is noted (paw sharply withdrawn). As described by Chaplan et al. 1994, once the threshold was crossed, the 2 responses straddling the threshold are retrospectively designated as the first 2 responses. Four additional responses were measured to stimuli varied sequentially up or down based on the animal's response. The 6 responses in the immediate vicinity of the threshold were used to calculate the 50% g threshold:

$$50\% \text{ g threshold} = (10^{[Xf+k*d]})/10000$$

Xf is the final filament used (in log units). The parameter k is from the Appendix 1 in Chaplan and was determined by the pattern of the von Frey responses (e.g. OXOXOX where 'O' indicates no response and 'X' denotes a withdrawal). The parameter d is the difference between stimuli which Chaplan used a constant d=0.224. To accommodate for the use of the 10 g and 26 g filaments, the exact difference between stimuli were used.

Rats that had a pre-paclitaxel von Frey score of less than 12 g were not included in the study. PWT was measured according to the Schematics in FIG. 9 (prevention) and FIG. 10 (reversal study).

Statistical Analysis

Data was analyzed by analysis of variance (ANOVA) followed by post-hoc comparisons where appropriate. An effect will be considered significant if p<0.05. Data was represented as the mean and standard error to the mean (s.e.m). Statistical outliers that fell above or below 2 standard deviations of the mean were identified but not removed from the final analysis.

Results

Body Weight

Baseline Body Weight—One way ANOVA found no differences in the BW among the groups prior to treatment.

Figures 9, 10, 11:
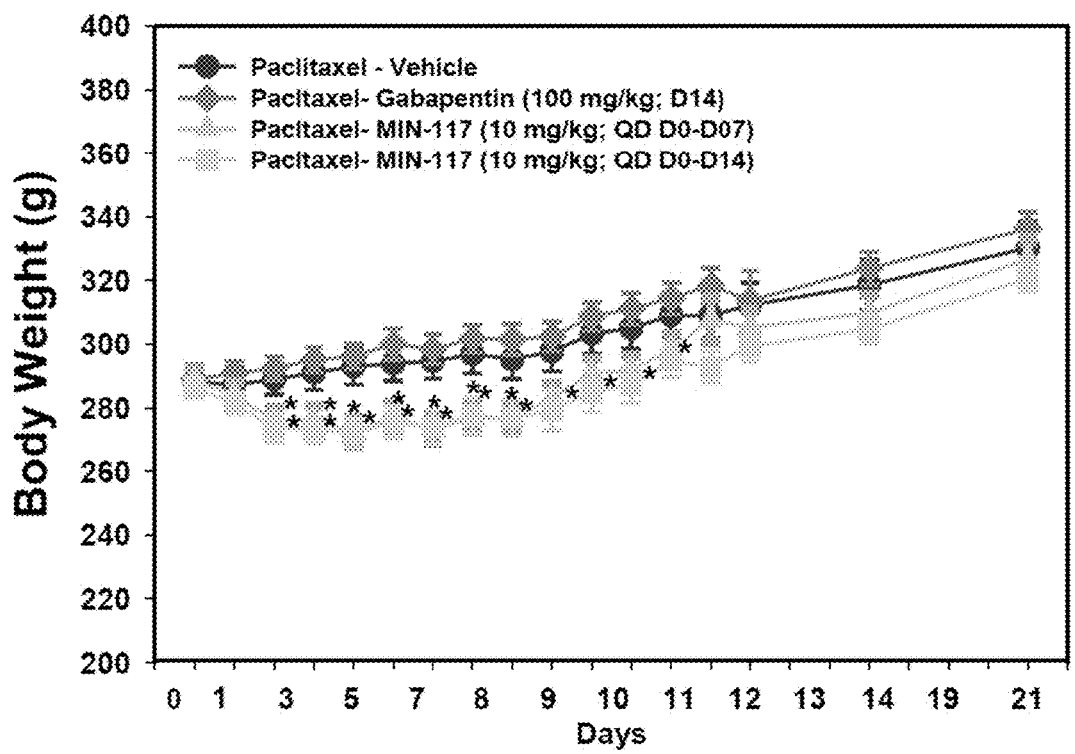
FIG. 9 is a schematic summarizing the experiments to determine the efficacy of MIN-117 in preventing paclitaxel-induced peripheral neuropathic pain.
FIG. 10 is a schematic summarizing the experiments to determine the efficacy of MIN-117 in reversing the effects of paclitaxel-induced peripheral neuropathic pain
FIG. 11 is series of line graphs that represent the effect of paclitaxel and test compounds on body weight of rats during the paclitaxel-induced peripheral neuropathic pain study described in Example 6. (Data are presented as mean±s.e.m.)

Body Weight during treatment—the effect of paclitaxel and test compounds on BW throughout the study is shown in FIG. 11. Repeated measures ANOVA found a significant treatment effect and treatment x day interactions. Compared to vehicle (line with ● in FIG. 11), rats treated with MIN-117 10 mg/kg (lines with ▲ and ■ in FIG. 11) showed a decrease in body weight. The effect was seen from day 2 until day 11.

Paw Withdrawal Threshold (PWT)

Figure 12:
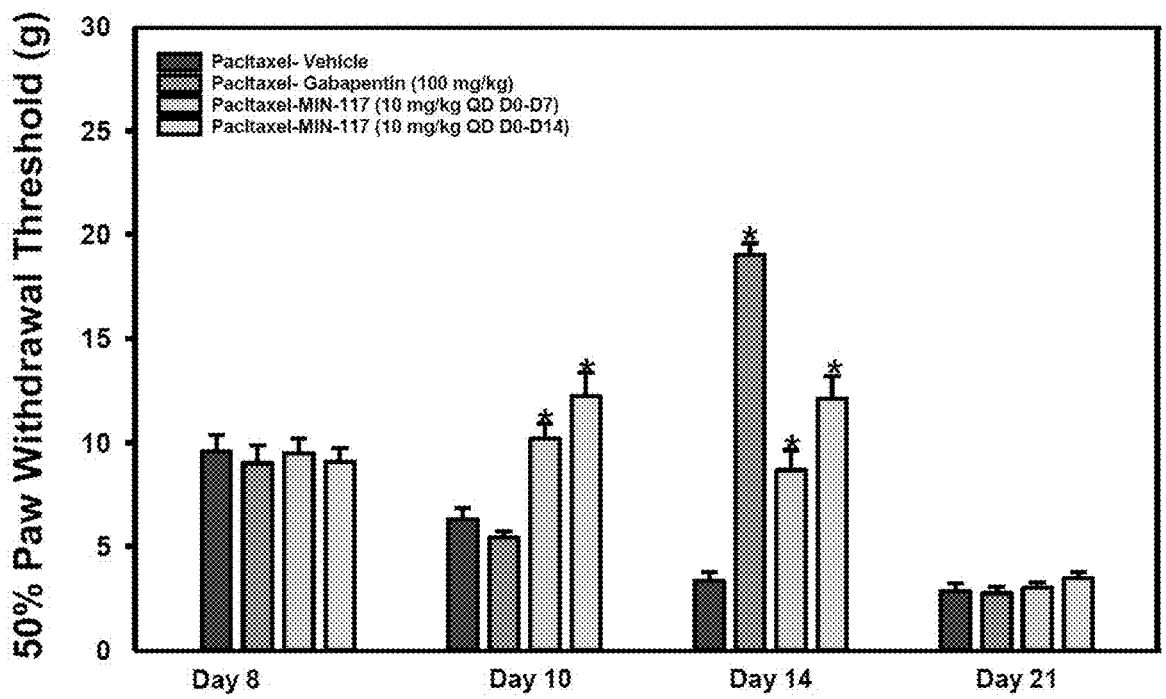
FIG. 12 is a series of bar graphs showing the effect of gabapentin, various doses of MIN-117, and vehicle on paw withdrawal thresholds on days 8, 10, 14 and 21 after paclitaxel treatment on days 1, 3, 5, and 7. (Data are presented as mean±s.e.m.) *$p<0.05$ compared to vehicle.

ANOVA found no differences in the baseline PWT among the treatment groups. On the other hand, the effects of MIN-117 on PWT on days 8, 10, 14 and 21 are shown in FIG. 12. ANOVA found a significant treatment effect on days 10 and 14. Compared to vehicle (left-most columns in FIG. 12), rats treated with MIN-117 at a dose of 10 mg/kg for either one (second columns from right in FIG. 12) or two weeks (right-most columns in FIG. 12) showed significantly higher PWT when tested 2 hours post dosing. Gabapentin tested on day 14 also showed significantly higher PWT compared to vehicle (second columns from left in FIG. 12).

On day 21, one week or two weeks after cessation of treatment, PWT responses of MIN-117-10 mg/kg treated groups returned to vehicle levels and no significant differences were seen between the various treatment groups.

Reversal Study Results

Body Weight

Baseline Body Weight—one way ANOVA found no differences in the BW among the groups prior to treatment.

Post-paclitaxel Baseline Body Weight—one way ANOVA found no differences in the BW among the groups prior to treatment.

Figure 13:
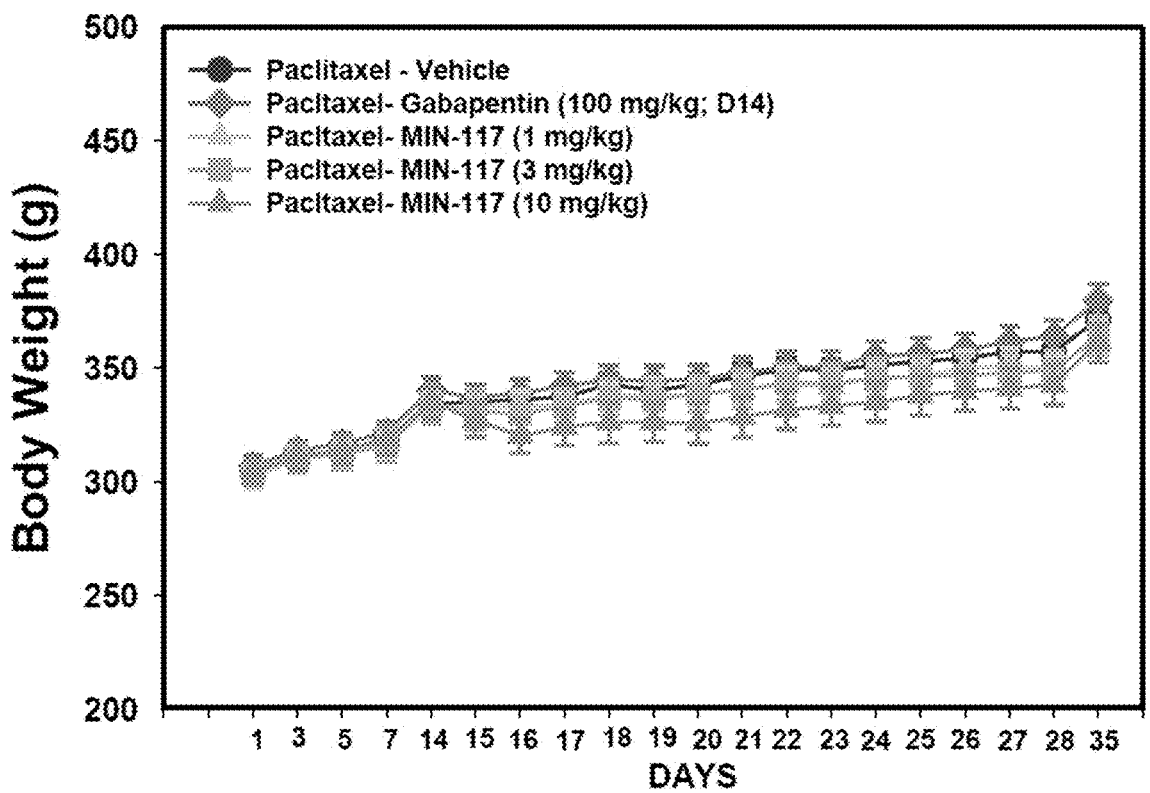
FIG. 13 is a series of line graphs that represent the effect of paclitaxel and test compounds on the body weight of rats during the reversal of paclitaxel-induced peripheral neuropathic pain study described in Example 6. (Data are presented as mean±s.e.m.)

Body Weight during treatment—the effects of paclitaxel and MIN-117 on BW throughout the study are shown in FIG. 13. Repeated measures ANOVA found no significant treatment effect. Although there was a significant treatment x day interactions, compared to vehicle none of the treatments showed significant effect on BW.

Paw Withdrawal Threshold (PWT)

Figure 14:
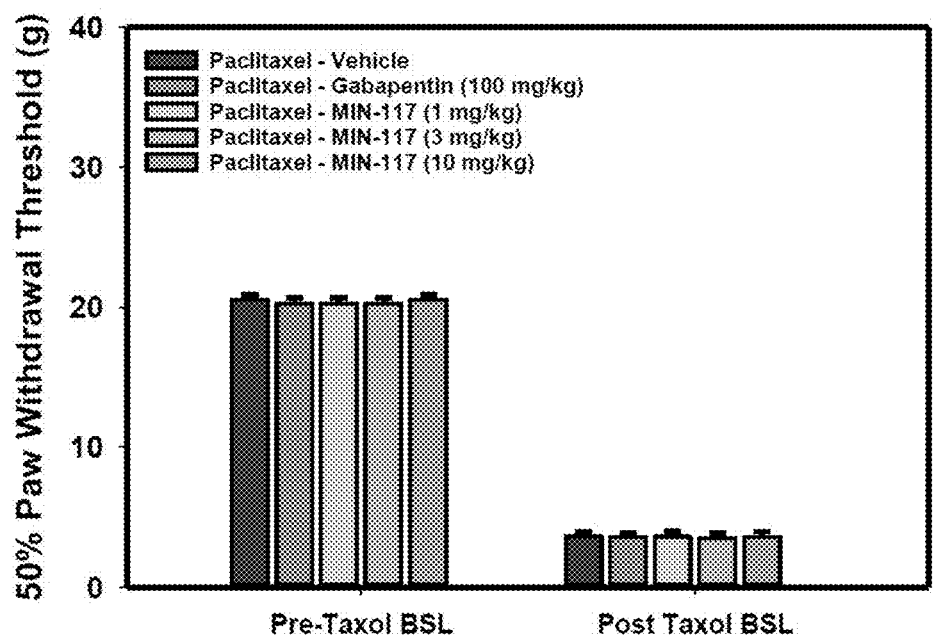
FIG. 14 is a series of bar graphs showing the effects of paclitaxel treatment on baseline paw withdrawal thresholds. (Data are presented as mean±s.e.m.)

ANOVA found no differences in the baseline PWT among the treatment groups. (FIG. 14)

Figure 15:
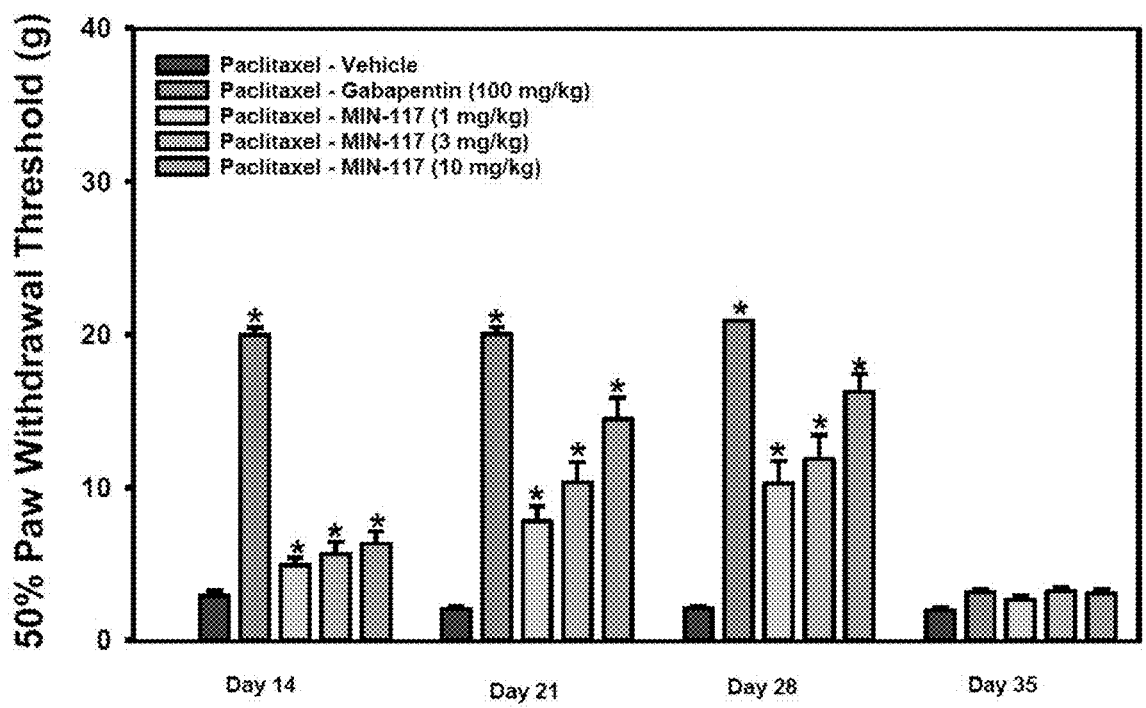
FIG. 15 is a series of bar graphs showing the effect of gabapentin, various doses of MIN-117, and vehicle on paw withdrawal thresholds on days 14, 21, 28 and 35 after paclitaxel treatment on days 1, 3, 5, and 7. (Data are presented as mean±s.e.m.) *p<0.05 compared to vehicle.

The effects of MIN-117 on PWT on days 14, 21, 28, and 35 are shown in FIG. 15. ANOVA found a significant treatment effect on days 14, 21, and 28. Compared to vehicle (left-most columns in FIG. 15), rats treated with MIN-117 at doses of 1 mg/kg (middle columns in FIG. 15), 3 mg/kg (second columns from right in FIG. 15), and 10 mg/kg (right-most columns in FIG. 15) or Gabapentin at a dose of 100 mg/kg (second columns from left in FIG. 15) showed significantly higher PWT when tested 2 hours post dosing. (Gabapentin was tested at 1 hour post dosing.) On day 35, one week after cessation of treatment, PWT responses of MIN-117 or Gabapentin treated groups returned to vehicle levels and no significant differences were seen between the various treatment groups.

SUMMARY

This study evaluated the efficacy of chronic administration of MIN-117 on paclitaxel-induced neuropathic pain to either reverse paclitaxel-induced pain response or prevent it.

For the prevention study a single dose was tested (10 mg/kg) and was injected for either 7 or 14 days starting one day prior to paclitaxel. Under this treatment regimen significant increases in PWT was seen 10 and 14 days after administration when compared to vehicle.

For the reversal study MIN-117 was tested at 1, 3 and 10 mg/kg following 2 weeks administration. All doses showed significant increase in PWT when tested on days 1, 7 and 14 of MIN-117 treatment corresponding to days 14, 21 and 28 from commencing the study.

When rats were tested one week following cessation of treatment, no analgesic effects were seen at any of the doses of MIN-117 in either study suggesting the effects were not long lasting.

Gabapentin when administered chronically or acutely showed a significant increase in PWT. The analgesic effects of gabapentin were not long lasting either and after cessation of treatment, no significant effect on PWT was seen when compared to vehicle.

Example 7

Evaluation of Other Antidepressants in Treating Chemotherapy-Induced Neuropathy

Two classes of antidepressants were also evaluated in Paw Withdrawal Threshold (PWT) experiments: duloxetine, a serotonin norepinephrine reuptake inhibitor, and amitriptyline, a tricyclic antidepressant. These experiments were conducted in a similar manner to the experiments described in Example 6.

Figure 16:
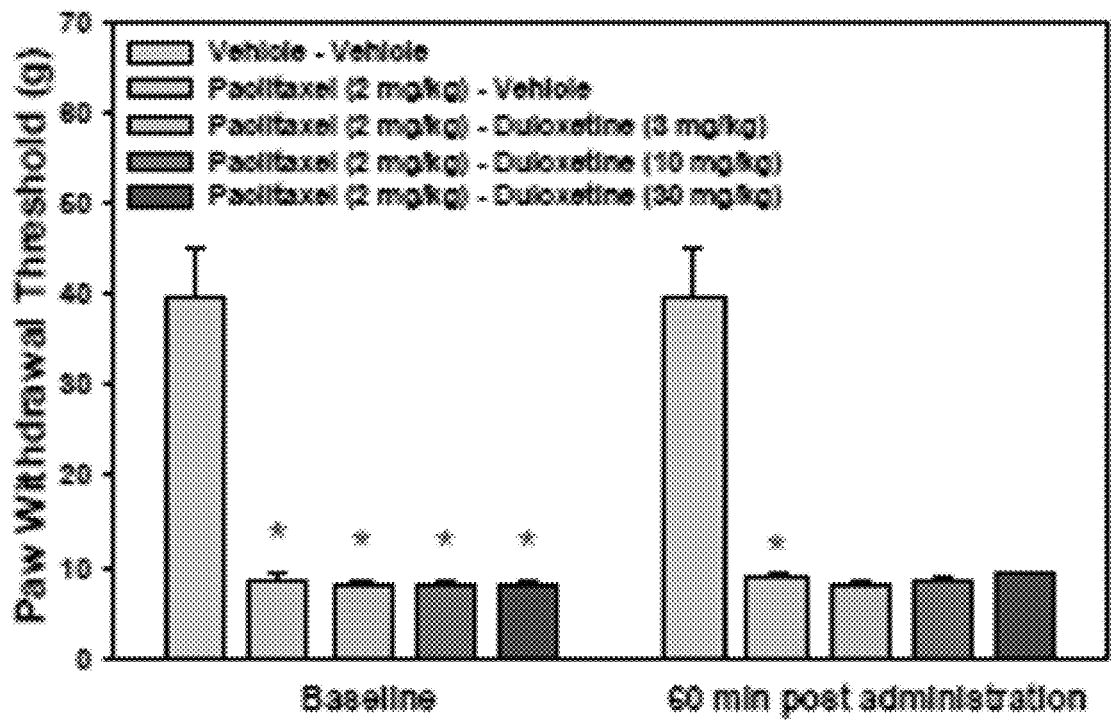
FIG. 16 is a series of bar graphs showing the effect of vehicle and various doses of duloxetine on paw withdrawal thresholds (pre-treatment and 60 minutes post-treatment). (Data are presented as mean±s.e.m.) *p<0.05 compared to vehicle/vehicle.

On day 22, post-paclitaxel administration (left-most columns in FIG. 16 correspond to rats not administered paclitaxel), rats were administered vehicle (second columns from left in FIG. 16) or duloxetine (orally) and PWT was assessed 60 min. following injection. Data represents mean±s.e.m. (* p<0.05 vs. vehicle/vehicle).

It was shown that duloxetine at doses of 3 mg/kg (middle columns in FIG. 16), 10 mg/kg (second columns from right in FIG. 16), and 30 mg/kg (right-most columns in FIG. 16) had no effect on PWT in paclitaxel-treated rats, i.e., duloxetine was not found to reverse paclitaxel-induced neuropathy in rats.

On day 27, post-paclitaxel administration (left-most columns in FIG. 17 correspond to rats not administered paclitaxel), rats were administered vehicle (second columns from left in FIG. 17) or amitriptyline (orally) and PWT was assessed 60 min. following injection. Data represents mean±s.e.m. (* $p<0.05$ vs. vehicle/vehicle, #$p<0.05$ vs. paclitaxel/vehicle).

Figure 17:
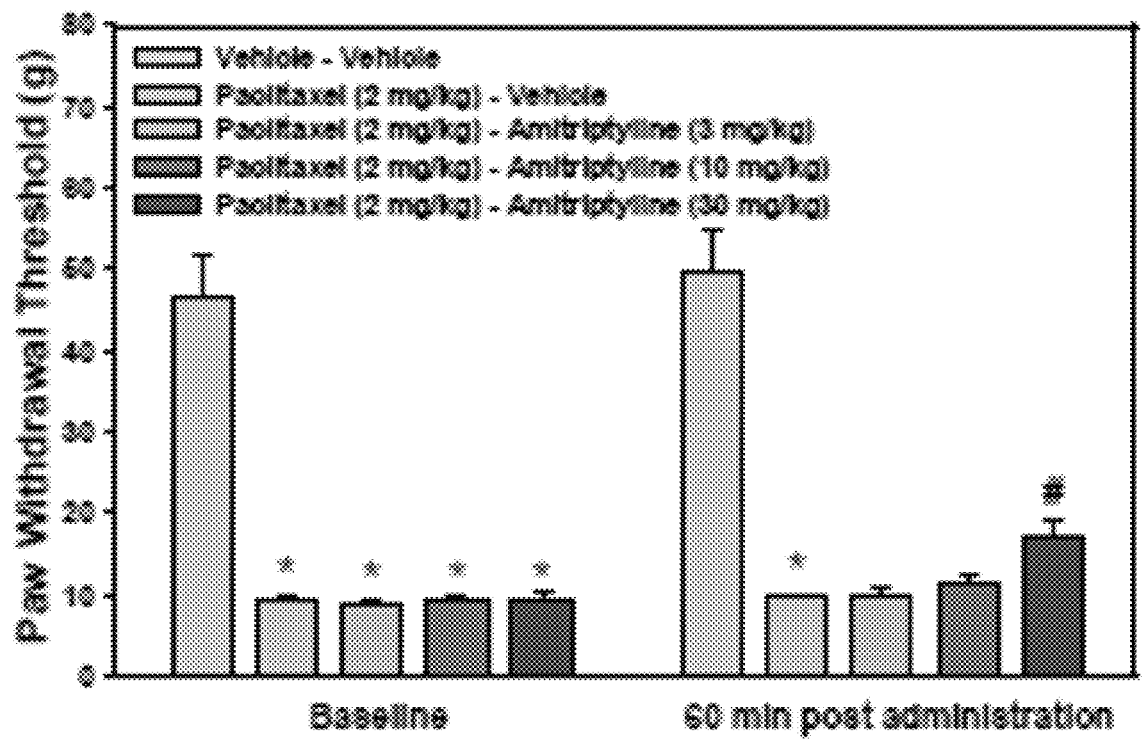
FIG. 17 is a series of bar graphs showing the effect of vehicle and various doses of amitriptyline on paw withdrawal thresholds (pre-treatment and 60 minutes post-treatment). (Data are presented as mean±s.e.m.) *p<0.05 compared to vehicle/vehicle. #p<0.05 compared to paclitaxel/vehicle.

It was shown that amitriptyline only partially reversed this neuropathy, but only at the highest dose tested, i.e., at 30 mg/kg (right-most columns in FIG. 17). Amitriptyline was not found to reverse paclitaxel-induced neuropathy in rats at doses of 3 mg/kg (middle columns in FIG. 17) and 10 mg/kg (second columns from right in FIG. 17).

The invention claimed is:

1. A method of treating or preventing chemotherapy-induced pain in a subject in need of treatment comprising administering to the subject a therapeutically effective amount of Compound I,

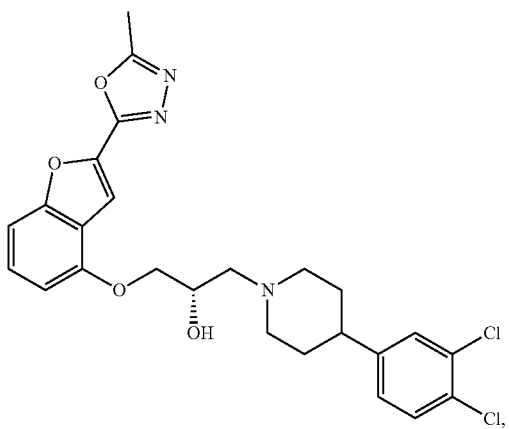 [SMILES: Cc1nnc(-c2cc3c(OC[C@@H](O)CN4CCC(c5ccc(Cl)c(Cl)c5)CC4)cccc3o2)o1]

or a pharmaceutically acceptable salt, solvate, or prodrug thereof.

2. The method of claim 1, wherein the therapeutically effective amount of Compound I is 1 mg to 1,000 mg.

3. The method of claim 1, wherein the therapeutically effective amount of Compound I is administered to the subject once a day, twice a day, three times a day, four times a day, once every two days, once every three days, once every four days, once every five days, once every six days, once a week, once every two weeks, once every three weeks, or once a month.

4. The method of claim 1, wherein Compound I, or a pharmaceutically acceptable salt, solvate, or prodrug thereof, is formulated as a pharmaceutical composition comprising one or more pharmaceutically acceptable excipients.

5. The method of claim 4, wherein the pharmaceutical composition further comprises an additional therapeutic agent for the treatment or prevention of chemotherapy-induced pain.

6. The method of claim 4, wherein the pharmaceutical composition is administered orally, parenterally, intravenously, intramuscularly, intrathecally, subcutaneously, topically, systemically, cutaneously, sublingually, buccally, rectally, vaginally, ocularly, otically, nasally, by inhalation, by nebulization, or transdermally.

7. The method of claim 6, wherein the pharmaceutical composition is administered to the subject orally and is formulated as a tablet, capsule, chew, gel, paste, multiparticulate, nanoparticulate, lozenge, pastille, granule, powder, solution, spray, emulsion, suspension, syrup, mouthwash, or drop.

8. The method of claim 1, further comprising administering an additional therapeutic agent to the subject for the treatment or prevention of chemotherapy-induced pain.

9. The method of claim 8, wherein the additional therapeutic agent and Compound I, or a pharmaceutically acceptable salt, solvate, or prodrug thereof, or a pharmaceutical composition comprising Compound I, or a pharmaceutically acceptable salt, solvate, or prodrug thereof, are administered in temporal proximity.

10. The method of claim 1, wherein the subject is a human.

11. The method of claim 1, wherein upon improvement in the subject's chemotherapy-induced pain, the subject is then administered a maintenance dose of Compound I and/or an additional therapeutic agent for the treatment or prevention of chemotherapy-induced pain.

12. The method of claim 11, wherein the maintenance dose of Compound I and/or the additional therapeutic agent is lower than the induction dose, administered less frequently than the induction dose, or lower than the induction dose and administered less frequently than the induction dose.

13. The method of claim 1, wherein Compound I is a hydrochloride salt.

14. The method of claim 1, wherein the chemotherapy-induced pain is chemotherapy-induced peripheral neuropathic pain.

15. The method of claim 1, wherein the chemotherapy is paclitaxel.

16. The method of claim 1, wherein the therapeutically effective amount of Compound I is 0.1 mg/kg to 100 mg/kg.

17. The method of claim 16, wherein the therapeutically effective amount of Compound I is about 10 mg/kg.

18. The method of claim 6, wherein the pharmaceutical composition is administered to the subject topically and is formulated as a cream, paste, lotion, gel, patch, or spray.

* * * * *